United States Patent
Thompson

(10) Patent No.: US 11,814,387 B2
(45) Date of Patent: Nov. 14, 2023

(54) CYCLIC AMIDE-CONTAINING PYRIDYL XANTHINES AS $A_{2B}$ ANTAGONISTS

(71) Applicant: Purnovate, Inc., Charlottesville, VA (US)

(72) Inventor: Robert D Thompson, Charlottesville, VA (US)

(73) Assignee: Adovate, LLC, Charlottesville, VA (US)

( * ) Notice: Subject to any disclaimer, the term of this patent is extended or adjusted under 35 U.S.C. 154(b) by 0 days.

(21) Appl. No.: 17/663,551

(22) Filed: May 16, 2022

(65) Prior Publication Data

US 2022/0402919 A1    Dec. 22, 2022

Related U.S. Application Data

(60) Provisional application No. 63/201,905, filed on May 18, 2021.

(51) Int. Cl.
| | | |
|---|---|---|
| *C07D 473/08* | (2006.01) | |
| *A61P 3/10* | (2006.01) | |
| *A61P 29/00* | (2006.01) | |
| *A61P 37/00* | (2006.01) | |
| *A61P 35/00* | (2006.01) | |
| *A61P 9/00* | (2006.01) | |
| *A61P 11/06* | (2006.01) | |

(52) U.S. Cl.
CPC .............. *C07D 473/08* (2013.01); *A61P 3/10* (2018.01); *A61P 9/00* (2018.01); *A61P 11/06* (2018.01); *A61P 29/00* (2018.01); *A61P 35/00* (2018.01); *A61P 37/00* (2018.01)

(58) Field of Classification Search
CPC .................................................... C07D 473/08
See application file for complete search history.

(56) References Cited

U.S. PATENT DOCUMENTS

| | | | |
|---|---|---|---|
| 7,342,006 B2 | 3/2008 | Wang et al. | |
| 7,579,348 B2 | 8/2009 | Wang et al. | |
| 7,605,143 B2 | 10/2009 | Rieger et al. | |
| 7,732,455 B2 | 6/2010 | Wang et al. | |
| 7,875,608 B2 | 1/2011 | Thompson et al. | |
| 7,884,100 B2 | 2/2011 | Wang et al. | |
| 8,058,259 B2 | 11/2011 | Thompson et al. | |
| 8,153,628 B2 | 4/2012 | Wang et al. | |
| 8,193,200 B2 | 6/2012 | Sitaraman et al. | |
| 8,252,797 B2 | 8/2012 | Palle et al. | |
| 9,221,821 B2 | 12/2015 | Diep et al. | |
| 2011/0082139 A1 | 4/2011 | Wang et al. | |
| 2012/0258974 A1 | 10/2012 | Belardinelli et al. | |
| 2014/0271606 A1 | 9/2014 | Sim | |

FOREIGN PATENT DOCUMENTS

| | | |
|---|---|---|
| WO | 2005/097140 A2 | 10/2005 |
| WO | 2011/005871 A1 | 1/2011 |
| WO | 2014/153424 A1 | 9/2014 |

OTHER PUBLICATIONS

PCT/US2022/072351 International Search Report dated Oct. 13, 2022.
PCT/US2022/072351 Written Opinion dated Oct. 13, 2022.
Pubchem, SID 319276977 2019, pp. 1-5 <https://pubchem.ncbi.nlm.nih.gov.substance/391276977>, downloaded on Sep. 17, 2022.
Abo-Salem et al., Antinociceptive Effects of Novel AZB Adenosine Receptor Antagonists, J. Pharma and Exp. Thera 2004, 308(1), 358-66.

*Primary Examiner* — Susanna Moore
(74) *Attorney, Agent, or Firm* — Vance Intellectual Property, PC

(57) ABSTRACT

Described herein are cyclic amide-containing pyridyl-xanthines of formula I and pharmaceutical compositions thereof that are useful as antagonists of A2B adenosine receptors.

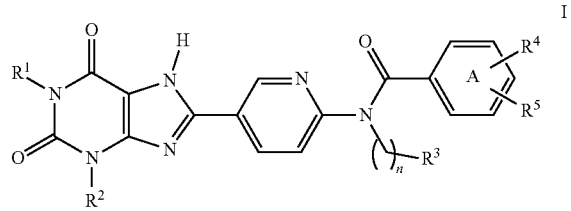

27 Claims, No Drawings

CYCLIC AMIDE-CONTAINING PYRIDYL XANTHINES AS $A_{2B}$ ANTAGONISTS

FIELD OF THE INVENTION

Described herein are cyclic amide-containing pyridyl-xanthines and pharmaceutical compositions thereof that are useful as antagonists of $A_{2B}$ adenosine receptors.

BACKGROUND OF THE INVENTION

Antagonists of $A_{2B}$ adenosine receptors are indicated for several different uses, including asthma and chronic obstructive pulmonary disorder (COPD). Efforts have yielded selective and potent $A_{2B}$ antagonists. However, $A_{2B}$ antagonists (e.g., the xanthine-based CVT-6883) typically are not very soluble and concomitantly suffer from low bioavailability and poor tissue penetration (see, for example, Bedford, S. T. et al., Bioorg. Med. Chem. Lett. 2009, 19, 5945-9 and Wang, G. et al., U.S. Pat. No. 7,601,732).

Therefore, it is important to continue to synthesize and test additional $A_{2B}$ receptor antagonists to develop new and improved therapeutic agents.

SUMMARY OF THE INVENTION

Accordingly, in an aspect, there are described novel cyclic amide-containing pyridyl-xanthines or pharmaceutically acceptable salts thereof that are $A_{2B}$ antagonists.

In another aspect, there are described novel pharmaceutical compositions, comprising: a pharmaceutically acceptable carrier and a therapeutically effective amount of at least one of the compounds described herein or a stereoisomer or pharmaceutically acceptable salt form thereof.

In another aspect, there are described novel methods of treating a pathological condition or symptom in a mammal for which the $A_{2B}$ receptor is implicated, and antagonism of the receptor provides therapeutic benefit by administering to a subject an effective amount of a compound described herein.

In another aspect, there are described novel methods of treating an adenosine $A_{2B}$ receptor-associated state in a subject by administering to the subject an effective amount of a compound described herein.

In another aspect, there are described compounds for use in medical therapy.

In another aspect, there is described the use of compounds described herein for the manufacture of a medicament for the treatment of a pathological condition or symptom in a mammal for which the $A_{2B}$ receptor is implicated, and antagonism of the receptor provides therapeutic benefit.

These and other objects, which will become apparent during the following detailed description, have been achieved by the inventors' discovery that the described compounds or stereoisomers or pharmaceutically acceptable salt forms thereof are $A_{2B}$ antagonists.

DETAILED DESCRIPTION OF THE INVENTION

All references cited herein are hereby incorporated in their entirety herein by reference.

In an aspect, there are described novel compounds of Formula I or a stereoisomer or pharmaceutically acceptable salt thereof:

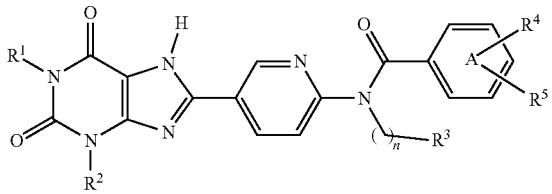

wherein:

n is selected from 1-10, wherein the $(CH_2)_n$ group is substituted with 0-1 groups selected from: $C_{1-6}$ alkyl, $C_{3-6}$ cycloalkyl, and —$C_{1-3}$ alkylene-$C_{3-6}$ cycloalkyl;

Ring A is selected from phenyl, naphthyl, and a 5-10 membered heteroaryl;

$R^1$ is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3$, and —$C_{1-6}$ alkylene-4-10 membered cyclic amide;

$R^2$ is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3$, and —$C_{1-6}$ alkylene-4-10 membered cyclic amide;

$R^3$ is a 4-10 membered cyclic amide;

$R^4$ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;

$R^5$ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;

$R^6$ is independently selected from: H, $C_{1-6}$ alkyl, $C_{3-6}$ cycloalkyl, and, —$C_{1-3}$ alkylene-$C_{3-6}$ cycloalkyl;

$R^7$ is independently selected from: H, $C_{1-6}$ alkyl, $C_{3-6}$ cycloalkyl, and, —$C_{1-3}$ alkylene-$C_{3-6}$ cycloalkyl; and, p is independently selected from: 0, 1, and 2;

alternatively, $R^4$ and $R^5$ are absent, and Ring A is replaced by a group selected from: $C_{1-6}$ alkyl, $CF_3$, $C_{3-6}$ cycloalkyl, —$CH_2$—$OCH_3$, —$(CH_2)_2$—$OCH_3$, —$CH_2$—O-phenyl, and —$CH_2$—O-pyridyl;

alternatively, —$(CH_2)_n$—$R^3$ is selected from: $C_{1-6}$ alkyl, —$C_{1-3}$ alkylene-$C_{3-6}$ cycloalkyl, —$(CH_2)_2$—$OCH_3$, —$(CH_2)_3$—$OCH_3$, and —$(CH_2)_4$—$OCH_3$, provided that at least one of $R^1$ and $R^2$ is an amide-containing group independently selected from: —$(CH_2)_2$—$NH(C(O)CH_3$ and —$C_{1-6}$ alkylene-4-10 membered cyclic amide.

In another aspect, there are described novel compounds of Formula I or a stereoisomer or pharmaceutically acceptable salt thereof, wherein:

n is selected from 2-10, wherein the $(CH_2)_n$ group is substituted with 0-1 groups selected from: $C_{1-2}$ alkyl, $C_{3-6}$ cycloalkyl, and —$C_{1-2}$ alkylene-$C_{3-6}$ cycloalkyl;

Ring A is selected from phenyl, naphthyl, and a 5-10 membered heteroaryl;

$R^1$ is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3$,

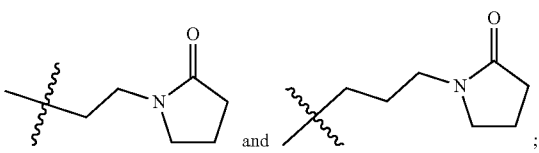 [SMILES: *CCN1CCCC1=O ; *CCCN1CCCC1=O]

R² is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3)$,

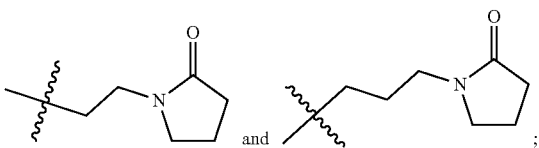

R³ is selected from:

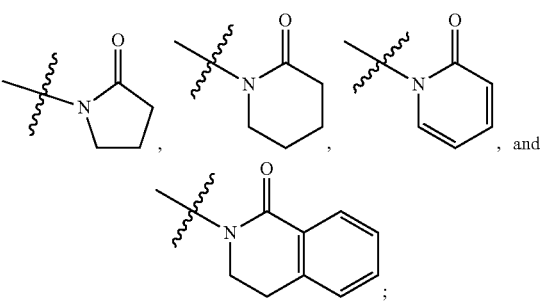

R⁴ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;

R⁵ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;

R⁶ is independently selected from: H, $C_{1-6}$ alkyl, $C_{3-6}$ cycloalkyl, and, —$C_{1-3}$ alkylene-$C_{3-6}$ cycloalkyl;

R⁷ is independently selected from: H, $C_{1-6}$ alkyl, $C_{3-6}$ cycloalkyl, and, —$C_{1-3}$ alkylene-$C_{3-6}$ cycloalkyl; and, p is independently selected from: 0, 1, and 2;

alternatively, —$(CH_2)_n$—R³ is selected from: $C_{1-6}$ alkyl, —$C_{1-3}$ alkylene-$C_{3-6}$ cycloalkyl, —$(CH_2)_2$—$OCH_3$, —$(CH_2)_3$—$OCH_3$, and —$(CH_2)_4$—$OCH_3$, provided that at least one of R¹ and R² is a group independently selected from: —$(CH_2)_2$—$NH(C(O)CH_3)$,

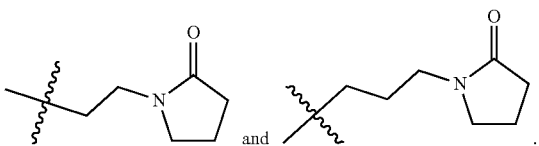 [SMILES: *CCN1CCCC1=O ; *CCCN1CCCC1=O]

In another aspect, there are described novel compounds of Formula I or a stereoisomer or pharmaceutically acceptable salt thereof, wherein:

n is selected from 2-4;

Ring A is selected from phenyl, pyridyl, and pyrimidyl;

R¹ is selected from: n-propyl, cyclopropyl, —$(CH_2)_2$—$OCH_3$, —$(CH_2)_3$—$OCH_3$, —$(CH_2)_4$—$OCH_3$, —$(CH_2)_2$—$NH(C(O)CH_3)$,

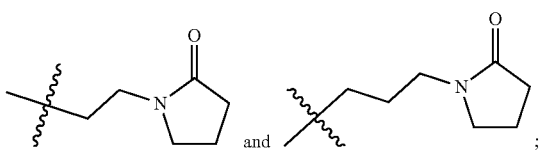 [SMILES: *CCN1CCCC1=O ; *CCCN1CCCC1=O]

R² is selected from: n-propyl, cyclopropyl, —$(CH_2)_2$—$OCH_3$, —$(CH_2)_3$—$OCH_3$, —$(CH_2)_4$—$OCH_3$, —$(CH_2)_2$—$NH(C(O)CH_3)$,

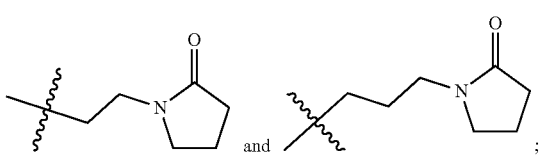 [SMILES: *CCN1CCCC1=O ; *CCCN1CCCC1=O]

R³ is selected from:

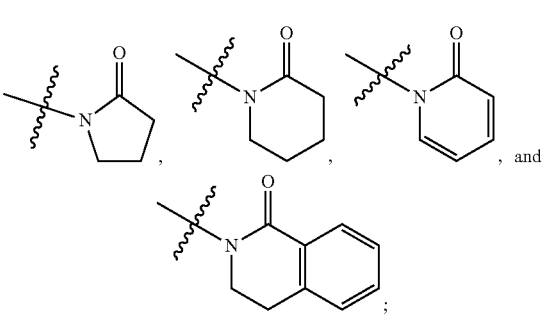

R⁴ is selected from: H, F, Cl, $C_{1-4}$ alkyl, $C_{3-6}$ cycloalkyl, —$CH_2$—$C_{3-6}$ cycloalkyl, $OR^6$, $NR^6R^7$, $CF_3$, and $OCF_3$;

R⁵ is selected from: H, F, Cl, $C_{1-4}$ alkyl, $C_{3-6}$ cycloalkyl, —$CH_2$—$C_{3-6}$ cycloalkyl, $OR^6$, $NR^6R^7$, $CF_3$, and $OCF_3$;

R⁶ is independently selected from: H, $C_{1-4}$ alkyl, $C_{3-6}$ cycloalkyl, and, —$CH_2$—$C_{3-6}$ cycloalkyl;

R⁷ is independently selected from: H, $C_{1-4}$ alkyl, $C_{3-6}$ cycloalkyl, and, —$CH_2$—$C_{3-6}$ cycloalkyl; alternatively, —$(CH_2)_n$—R³ is selected from: $C_{1-4}$ alkyl, —$CH_2$—$C_{3-6}$ cycloalkyl, —$(CH_2)_2$—$OCH_3$, —$(CH_2)_3$—$OCH_3$, and —$(CH_2)_4$—$OCH_3$, provided that at least one of R¹ and R² is a group independently selected from: —$(CH_2)_2$—$NH(C(O)CH_3)$,

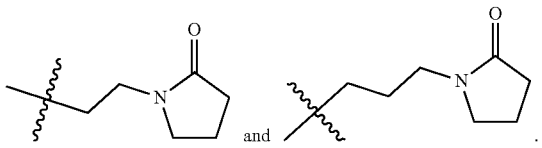 [SMILES: *CCN1CCCC1=O ; *CCCN1CCCC1=O]

In another aspect, there are described novel compounds of Formula I or a stereoisomer or pharmaceutically acceptable salt thereof, wherein:

n is selected from 2-4;

Ring A is selected from phenyl and pyridyl;

R¹ is selected from: n-propyl, cyclopropyl, —(CH₂)₂—OCH₃, —(CH₂)₃—OCH₃,

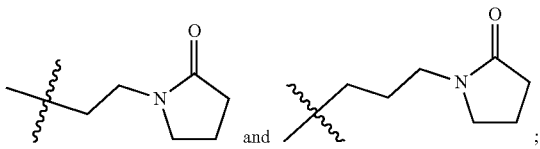 [SMILES: *CCN1CCCC1=O ; *CCCN1CCCC1=O]

;

R² is selected from: n-propyl, cyclopropyl, —(CH₂)₂—OCH₃, —(CH₂)₃—OCH₃,

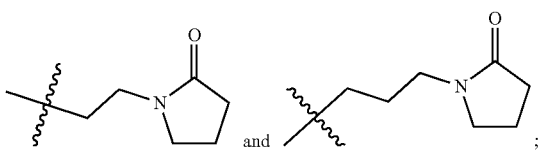

;

R³ is

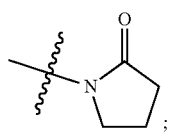 [SMILES: *N1CCCC1=O]

;

R⁴ is selected from: H, F, Cl, C₁₋₄ alkyl, C₃₋₆ cycloalkyl, —C₁ alkylene-C₃₋₆ cycloalkyl, and OR⁶;

R⁵ is selected from: H and F;

R⁶ is independently selected from: H and C₁₋₄ alkyl;

alternatively, —(CH₂)ₙ—R³ is selected from: —(CH₂)₂—OCH₃, and —(CH₂)₃—OCH₃, provided that at least one of R¹ and R² is a group independently selected from:

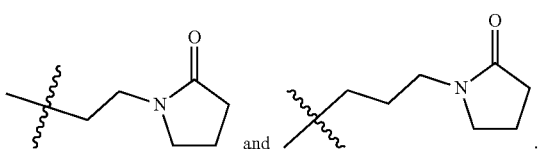 [SMILES: *CCN1CCCC1=O ; *CCCN1CCCC1=O]

.

In another aspect, there are described novel compounds of Formula I or a stereoisomer or pharmaceutically acceptable salt thereof, wherein:

n is selected from 2-3;

Ring A is selected from phenyl and pyridyl;

R¹ is selected from: n-propyl, cyclopropyl, —(CH₂)₂—OCH₃, —(CH₂)₃—OCH₃,

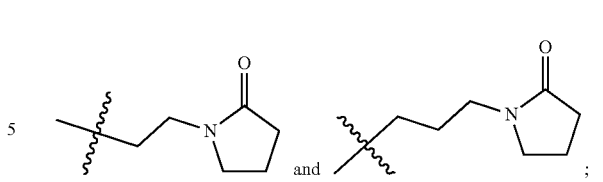

;

R² is selected from: n-propyl, cyclopropyl, —(CH₂)₂—OCH₃, and —(CH₂)₃—OCH₃;

R³ is

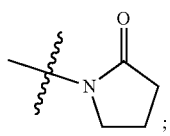 [SMILES: *N1CCCC1=O]

;

R⁴ is selected from: H, F, Cl, CH₃, cyclopropyl, and OR⁶;

R⁵ is selected from: H and F;

R⁶ is independently selected from: H and CH₃;

alternatively, —(CH₂)ₙ—R³ is selected from: —(CH₂)₂—OCH₃, and —(CH₂)₃—OCH₃, provided that R¹ is selected from:

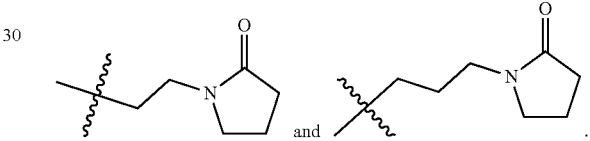

.

In another aspect, there are described novel compounds of Formula I or a stereoisomer or pharmaceutically acceptable salt thereof, wherein:

R³ is selected from:

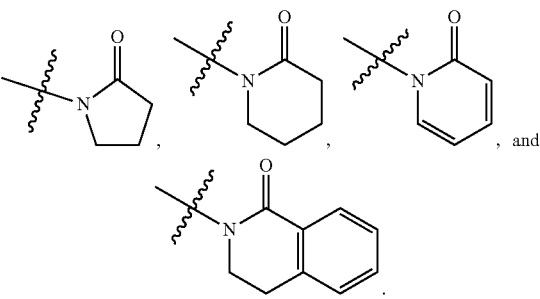

.

In another aspect, there are described novel compounds of Formula I or a stereoisomer or pharmaceutically acceptable salt thereof, wherein:

R³ is:

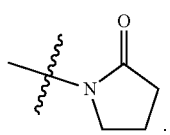

.

In another aspect, there are described novel compounds of Formula I or a stereoisomer or pharmaceutically acceptable salt thereof, wherein the compound is listed in Table 1 provided herein.

In another aspect, there are described novel compounds of Formula I or a stereoisomer or pharmaceutically acceptable salt thereof, wherein the compound is listed in Table 2 provided herein.

In another aspect, there are described novel compounds of Formula I or a stereoisomer or pharmaceutically acceptable salt thereof, wherein the compound is listed in Table 3.

TABLE 3

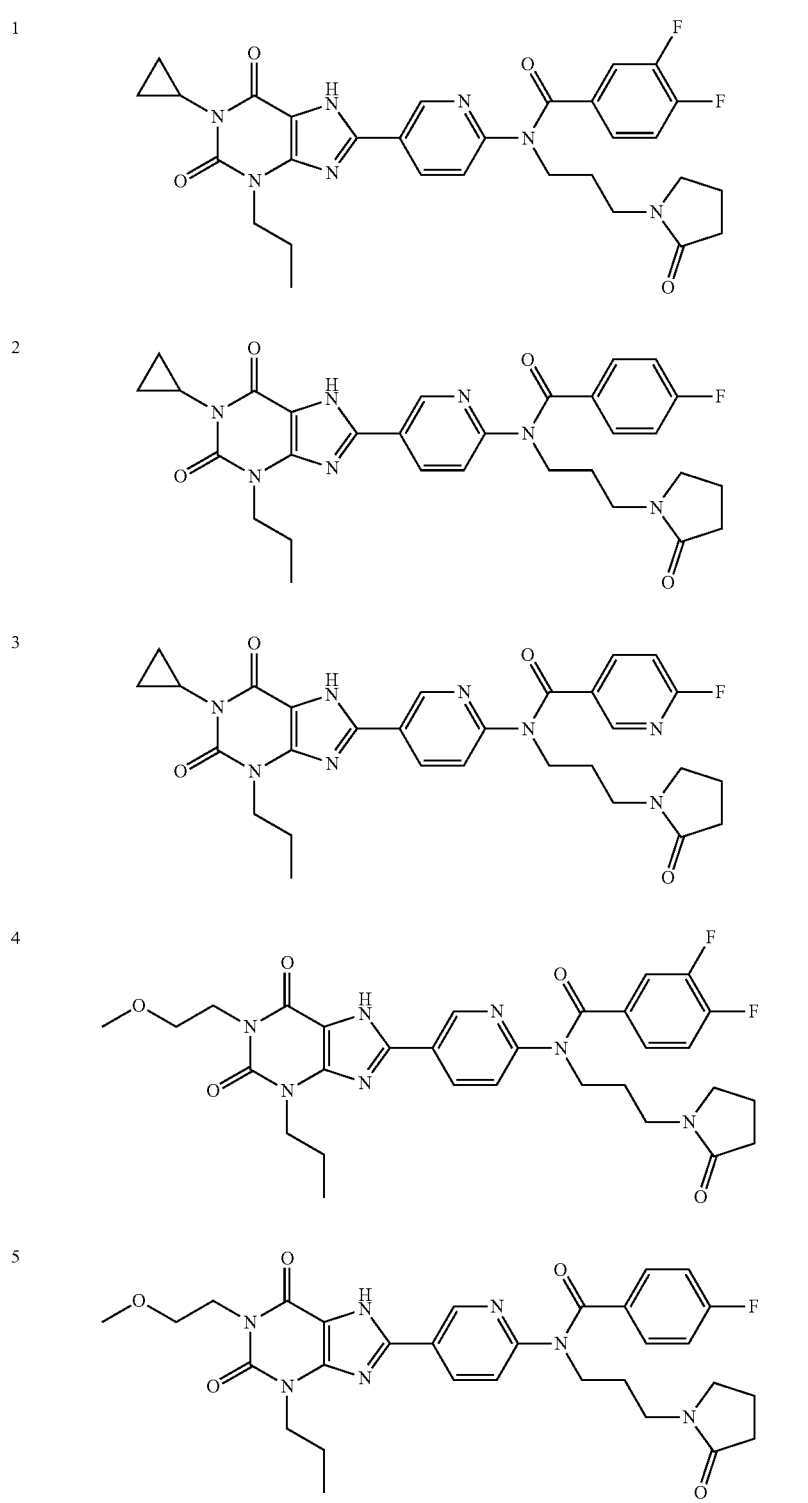

TABLE 3-continued
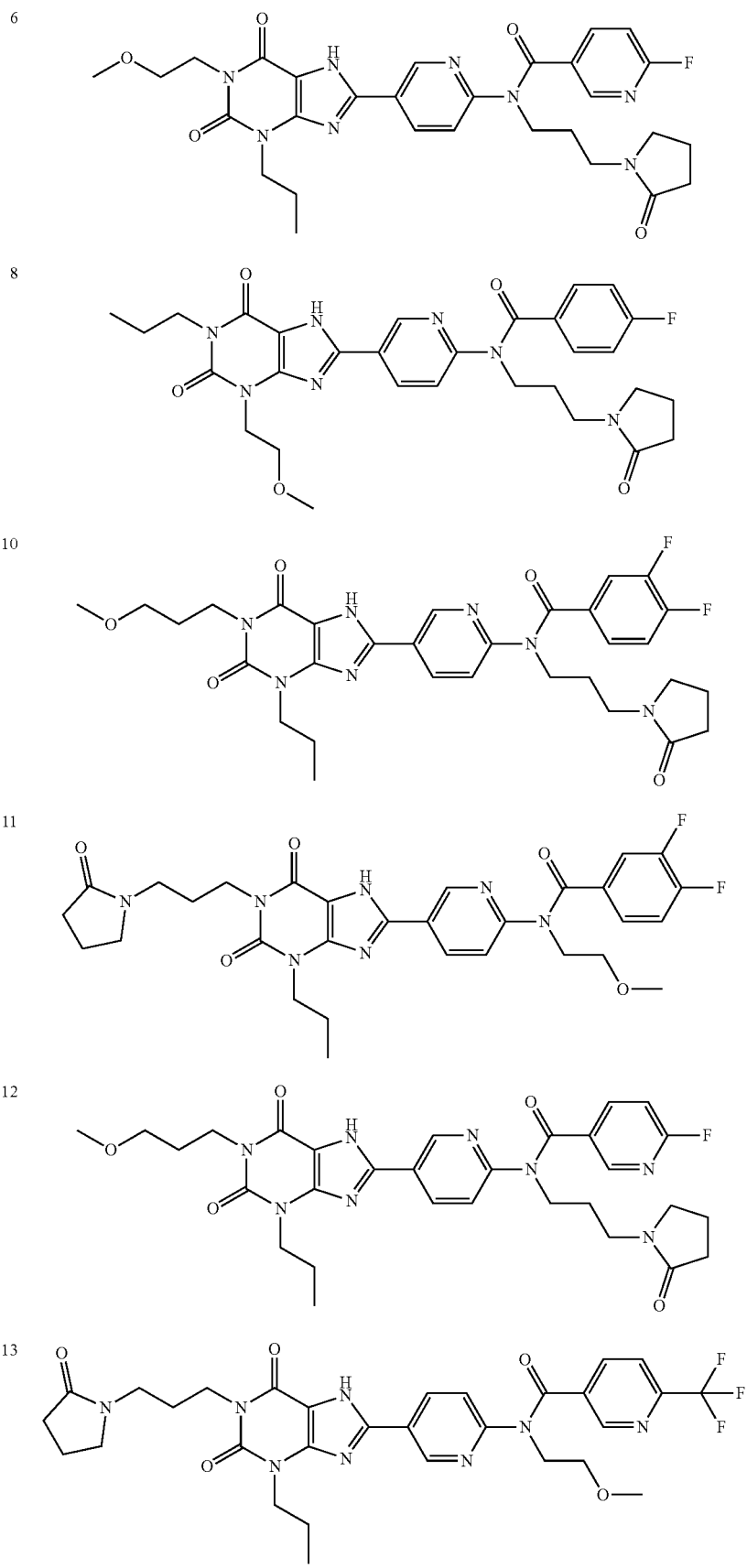

TABLE 3-continued
15
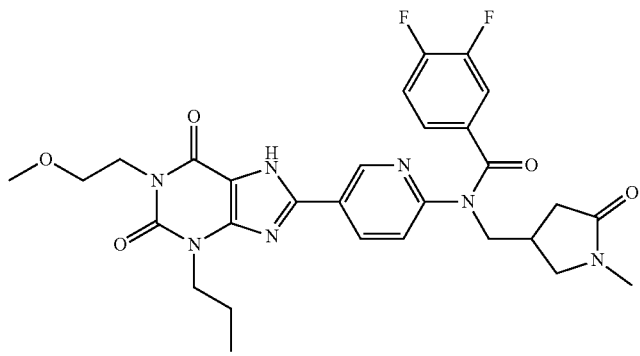 [SMILES: CCCn1c(=O)n(CCOC)c(=O)c2[nH]c(-c3ccc(N(CC4CC(=O)N(C)C4)C(=O)c4ccc(F)c(F)c4)nc3)nc21]
16
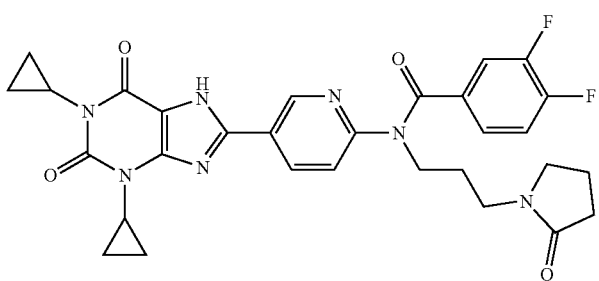 [SMILES: O=C1CCCN1CCCN(C(=O)c1ccc(F)c(F)c1)c1ccc(-c2nc3c([nH]2)c(=O)n(C2CC2)c(=O)n3C2CC2)cn1]
20
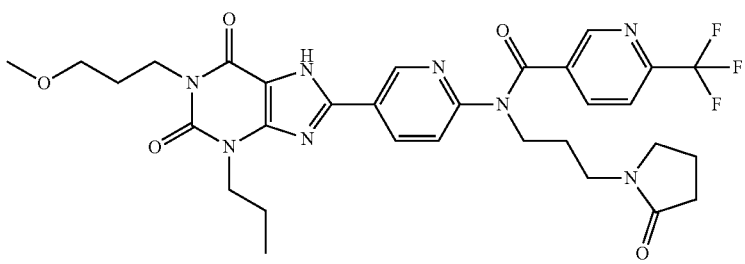 [SMILES: CCCn1c(=O)n(CCCOC)c(=O)c2[nH]c(-c3ccc(N(CCCN4CCCC4=O)C(=O)c4ccc(C(F)(F)F)nc4)nc3)nc21]
24
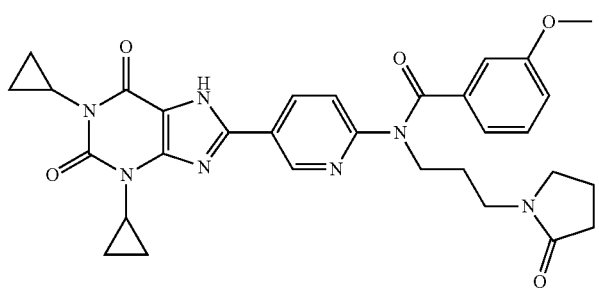 [SMILES: COc1cccc(C(=O)N(CCCN2CCCC2=O)c2ccc(-c3nc4c([nH]3)c(=O)n(C3CC3)c(=O)n4C3CC3)cn2)c1]
25
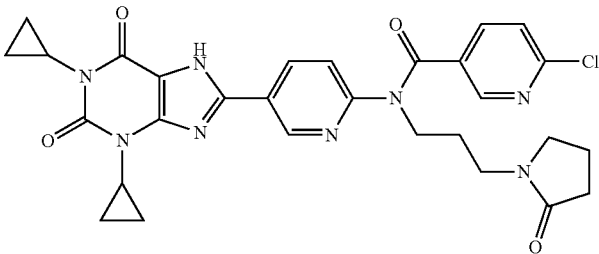 [SMILES: O=C1CCCN1CCCN(C(=O)c1ccc(Cl)nc1)c1ccc(-c2nc3c([nH]2)c(=O)n(C2CC2)c(=O)n3C2CC2)cn1]

TABLE 3-continued
26 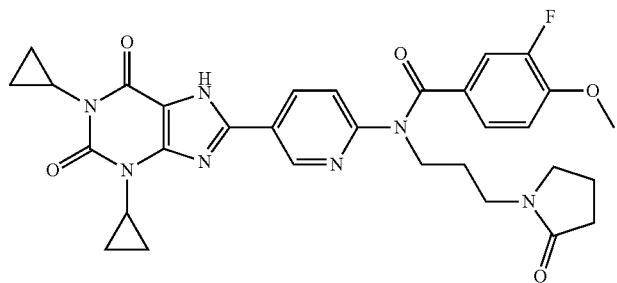 [SMILES: COc1ccc(C(=O)N(CCCN2CCCC2=O)c2ccc(-c3nc4c([nH]3)c(=O)n(C3CC3)c(=O)n4C3CC3)cn2)cc1F]
27 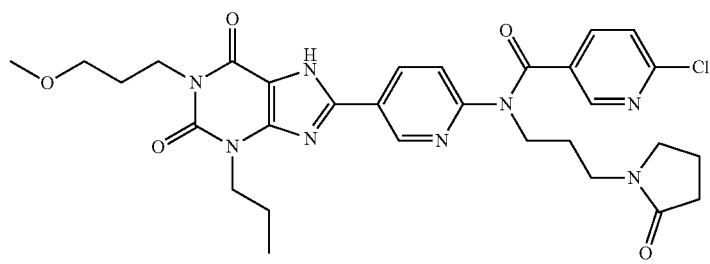 [SMILES: CCCn1c(=O)n(CCCOC)c(=O)c2[nH]c(-c3ccc(N(CCCN4CCCC4=O)C(=O)c4ccc(Cl)nc4)nc3)nc21]
28 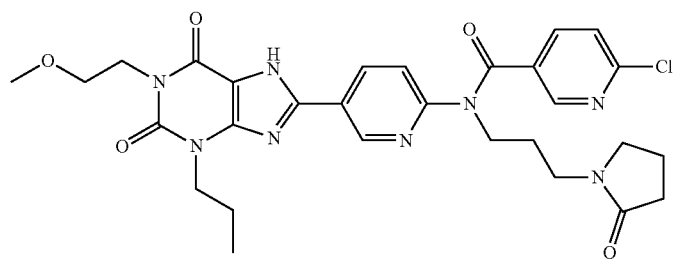 [SMILES: CCCn1c(=O)n(CCOC)c(=O)c2[nH]c(-c3ccc(N(CCCN4CCCC4=O)C(=O)c4ccc(Cl)nc4)nc3)nc21]
30 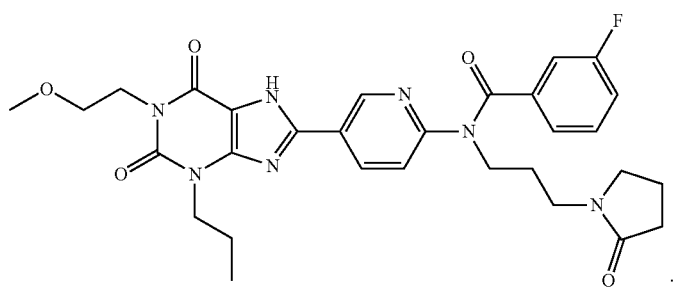 [SMILES: CCCn1c(=O)n(CCOC)c(=O)c2[nH]c(-c3ccc(N(CCCN4CCCC4=O)C(=O)c4cccc(F)c4)nc3)nc21]
In another aspect, there are described novel compounds of Formula I or a stereoisomer or pharmaceutically acceptable salt thereof, wherein the compound is listed in Table 4.
TABLE 4
1 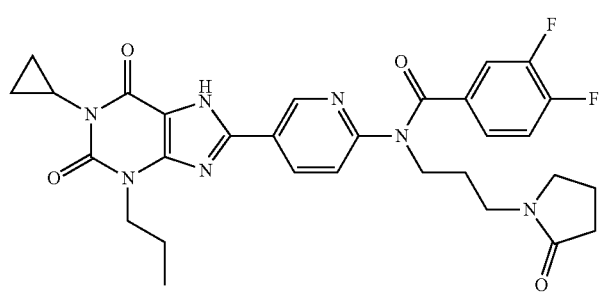 [SMILES: CCCn1c(=O)n(C2CC2)c(=O)c2[nH]c(-c3ccc(N(CCCN4CCCC4=O)C(=O)c4ccc(F)c(F)c4)nc3)nc21]

TABLE 4-continued
| 2 | 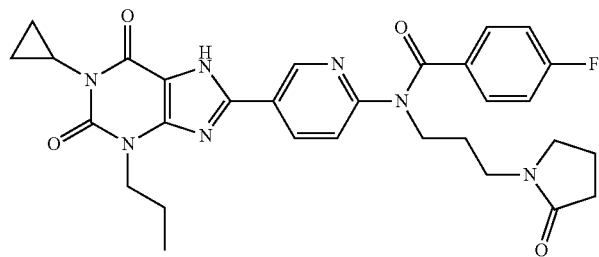 |
| --- | --- |
| 4 | 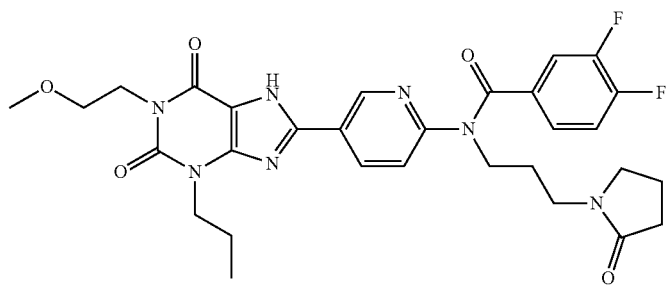 [SMILES: CCCn1c(=O)n(CCOC)c(=O)c2[nH]c(-c3ccc(N(CCCN4CCCC4=O)C(=O)c4ccc(F)c(F)c4)nc3)nc21] |
| 5 | 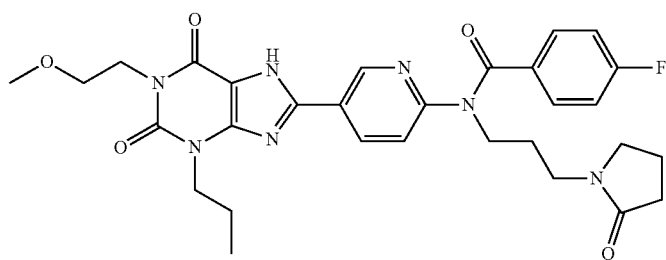 |
| 6 | 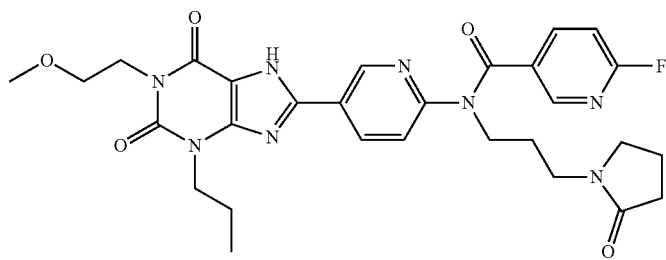 |
| 10 | 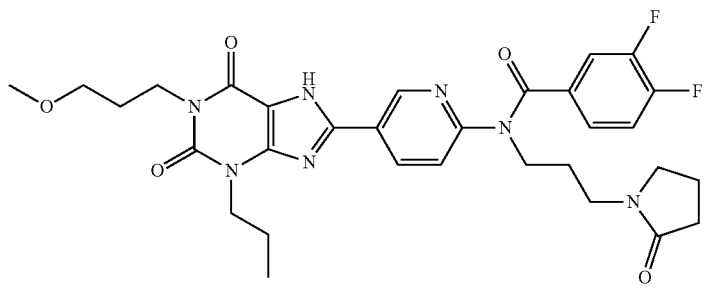 [SMILES: CCCn1c(=O)n(CCCOC)c(=O)c2[nH]c(-c3ccc(N(CCCN4CCCC4=O)C(=O)c4ccc(F)c(F)c4)nc3)nc21] |
| 12 | 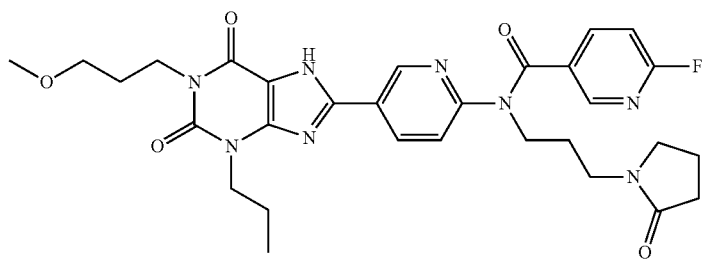 [SMILES: CCCn1c(=O)n(CCCOC)c(=O)c2[nH]c(-c3ccc(N(CCCN4CCCC4=O)C(=O)c4ccc(F)nc4)nc3)nc21] |

TABLE 4-continued
24
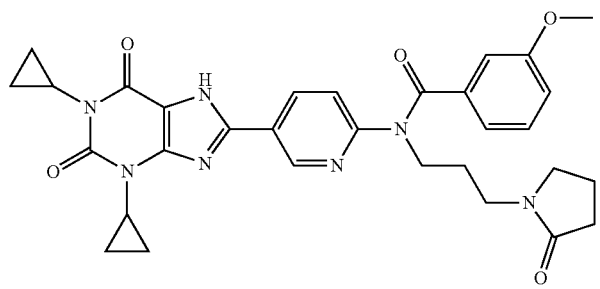 [SMILES: COc1cccc(C(=O)N(CCCN2CCCC2=O)c2ccc(-c3nc4c([nH]3)c(=O)n(C3CC3)c(=O)n4C3CC3)cn2)c1]
25
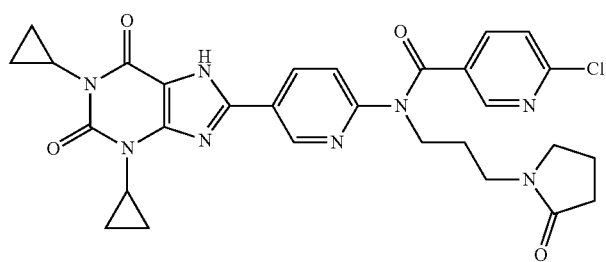 [SMILES: O=C1CCCN1CCCN(C(=O)c1ccc(Cl)nc1)c1ccc(-c2nc3c([nH]2)c(=O)n(C2CC2)c(=O)n3C2CC2)cn1]
26
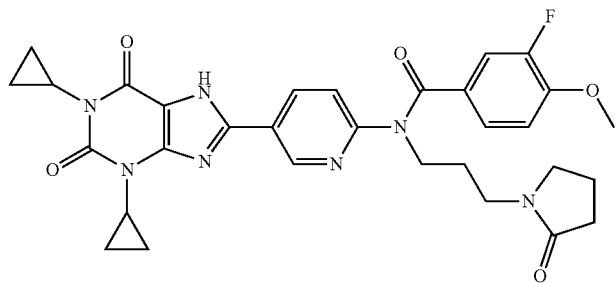 [SMILES: COc1ccc(C(=O)N(CCCN2CCCC2=O)c2ccc(-c3nc4c([nH]3)c(=O)n(C3CC3)c(=O)n4C3CC3)cn2)cc1F]
27
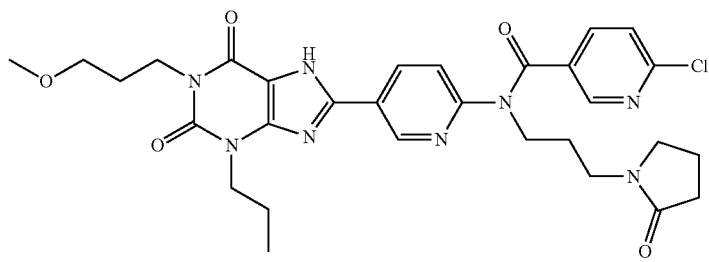 [SMILES: CCCn1c(=O)n(CCCOC)c(=O)c2[nH]c(-c3ccc(N(CCCN4CCCC4=O)C(=O)c4ccc(Cl)nc4)nc3)nc21]
28
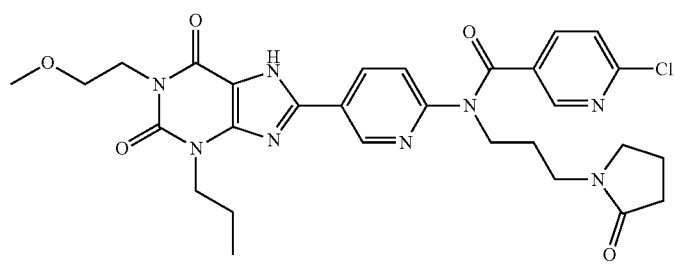 [SMILES: CCCn1c(=O)n(CCOC)c(=O)c2[nH]c(-c3ccc(N(CCCN4CCCC4=O)C(=O)c4ccc(Cl)nc4)nc3)nc21]

TABLE 4-continued

30

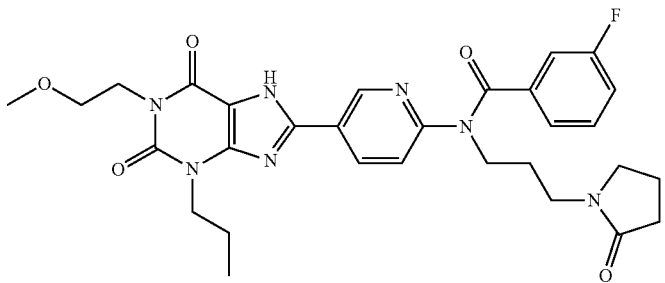 [SMILES: CCCn1c(=O)n(CCOC)c(=O)c2[nH]c(-c3ccc(N(CCCN4CCCC4=O)C(=O)c4cccc(F)c4)nc3)nc21]

In another aspect, there are described novel compounds of Formula I or a stereoisomer or pharmaceutically acceptable salt thereof, wherein the compound is deuterium-enriched (e.g., one or more H are replaced by D or the % of D present is higher than naturally occurring (e.g., 10, 20, 30, 40, 50, 60, 70, 80, 90 to 100% at a specific position, portion or the entire compound). For example, $R^1$ can be a deuterated propyl group (e.g., $-CD_2CD_2CD_3$). In addition, the groups recited in Ring A, $R^1$, $R^2$, $R^3$, $R^4$, $R^5$, $R^6$, and $R^7$ that contain a hydrogen (e.g., alkyl, cycloalkyl, alkylene, aryl, and heteroaryl) can be partially or fully replaced by D (e.g., $CD_3$, $CD_2CD_3$, $CD_2CD(CD_3)_2$, $d_5$-cyclopropyl, $d_7$-cyclobutyl, $d_9$-cyclopentyl, $d_5$-cyclopropyl-$CD_2$, $d_5$-phenyl, $d_4$-phenyl (one substituent is present), $d_3$-phenyl (two substituents are present), $d_4$-pyridyl, $d_3$-pyridyl (one substituent is present), and $d_2$-pyridyl (two substituent are present).

In another aspect, there are described novel compounds of Formula I wherein the compound is a deuterium-enriched compound of Formula $I_A$-$I_C$ or a stereoisomer or pharmaceutically acceptable salt thereof:

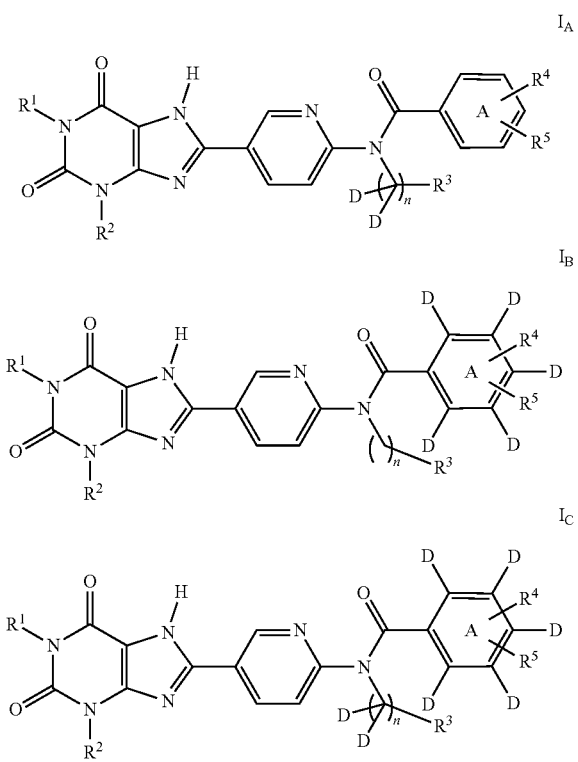

wherein the -D or C-D groups in Ring A are replaced by $R^4/R^5$ (if present, considered absent if H in formulae $I_{A-C}$) or by a N if ring A is a pyridyl ring.

Deuterium-enriched compounds described herein can be prepared by a number of known methods including deuterium exchange of acid labile hydrogens (e.g., contacting the compound with NaOD in $D_2O$) and using deuterated starting materials (e.g., deuterated iodo-adenosine-uronamide.

In another aspect, there is described a novel pharmaceutical composition, comprising: a therapeutically effective amount of a compound described herein or a stereoisomer or pharmaceutically acceptable salt thereof and a pharmaceutically acceptable carrier.

In another aspect, there is described a novel method for treating an adenosine $A_{2B}$ receptor associated state in a subject, comprising: administering to the subject therapeutically effective amount of a compound described herein or a stereoisomer or pharmaceutically acceptable salt thereof.

In another aspect, the adenosine $A_{2B}$ receptor associated state is selected from asthma, bronchoconstriction, chronic obstructive pulmonary disorder (COPD), angiogenesis, pulmonary fibrosis, emphysema, allergies, allergic diseases (e.g. allergic rhinitis (e.g., (perennial, seasonal, and occupational) and sinusitis), autoimmune diseases, inflammation, atherosclerosis, hypertension, congestive heart failure, retinopathy, diarrheal diseases, insulin resistance, Type 1 diabetes, Type 2 diabetes, obesity, fatty liver disease, pain (e.g., nociceptive pain), wound healing, inflammatory gastrointestinal tract disorders (e.g., inflammatory bowel disease), sickle cell disease, cancer (e.g., bladder (e.g., MB49 cell line) and breast (e.g., 4T1-12B cell line)), heart attack, diabetic retinopathy, hyperbaric oxygen-induced retinopathy, inhibition of angiogenesis in neoplastic tissues, gastrointestinal disorders, immunological disorders, hypersensitivity disorders, neurological disorders, and cardiovascular diseases due to both cellular hyperproliferation and apoptosis.

In another aspect, the state is an autoimmune disease selected from: Addison's disease, autoimmune hemolytic anemia, Crohn's disease, Goodpasture's syndrome, Graves' disease, Hashimoto's thyroiditis, idiopathic thrombocytopenic purpura, multiple sclerosis, myasthenia gravis, pemphigus vulgaris, pernicious anemia, poststreptococcal glomerulonephritis, psoriasis, rheumatoid arthritis, scleroderma, Sjogren's syndrome, spontaneous infertility, and systemic lupus erythematosus.

In another aspect, the adenosine $A_{2B}$ receptor associated state is selected from: asthma, insulin resistance, atherosclerosis, fatty liver disease, bladder cancer, and breast cancer.

In another aspect, the adenosine $A_{2B}$ receptor associated state is human cell line MDA-MB-231 breast cancer.

In another aspect, there is described a novel method a using an $A_{2B}$ antagonist as an analgesic adjuvant in a subject in need of analgesia, comprising: administering to the subject:
  a. a therapeutically effective amount of a compound described herein or a stereoisomer or pharmaceutically acceptable salt thereof; and,
  b. a therapeutically effective amount of an analgesic.

The benefit of this technique is that a lower dosage of the second analgesic (e.g., an opioid such as morphine) can be used. Examples of the analgesic include opioids and a non-steroidal anti-inflammatory drugs (NSAIDs). Examples of opioids include morphine, oxycodone, hydrocodone, dihydrocodone, codeine, fentanyl, hydromorphone, and methadone. Examples of NSAIDs include aspirin, ibuprofen, naproxen, nabumetone, and celecoxib.

In another aspect, there is described a novel compound for use in therapy.

In another aspect, there is described the use of novel compounds for the manufacture of a medicament for the treatment of an indication recited herein.

In another aspect, examples of the molecular weight of the compounds described herein include (a) less than about 500, 550, 600, 650, 700, 750, 800, 850, 900, 950, or 1000 grams per mole; (b) less than about 950 grams per mole; (c) less than about 850 grams per mole; and, (d) less than about 750 grams per mole.

In another aspect, examples of the solubility of the compounds described herein include greater than 50 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900 and 1000 μg/mL.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

A compound or compounds, includes, where appropriate, stereoisomers and/or pharmaceutically acceptable salts thereof.

"Adenosine $A_{2B}$ receptor antagonist" includes compounds that deactivate the adenosine $A_{2B}$ receptor with a $K_i$ of <1 μM as determined by a known binding assay. An adenosine $A_{2B}$ receptor antagonist may also be cross reactive with other adenosine receptor subtypes (e.g., $A_1$, $A_{2A}$, and $A_3$). In another aspect, the adenosine $A_{2B}$ receptor antagonist may be selective for $A_{2B}$ (e.g., at least 2, 10, 50, or 100/1 over another adenosine receptor subtype).

"Adenosine $A_{2B}$ receptor associated state" includes those diseases or disorders which are directly or indirectly implicated in the adenosine $A_{2B}$ receptor pathway. Without being bound by theory, it is thought that administration of an adenosine $A_{2B}$ antagonist blocks the biological activity of natural adenosine at the $A_{2B}$ receptor. Accordingly, an adenosine $A_{2B}$ receptor associated state includes those diseases and disorders directly associated with the activity of the adenosine $A_{2B}$ receptor or the activity of the biological pathway associated with the adenosine $A_{2B}$ receptor.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds described herein containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included herein. Specifically, cis and trans geometric isomers of the compounds described herein may also exist and may be isolated as a mixture of isomers or as separated isomeric forms. All processes used to prepare compounds described herein and intermediates made therein are considered to be part of the present invention. All tautomers of shown or described compounds are also considered to be part of the present invention.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

"Stable" means that the compound is suitable for pharmaceutical use.

Aspects described herein cover stable compounds and thus avoids, unless otherwise specified, the following bond types: heteroatom-halogen, N—S, O—S, O—O, and S—S.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

When an "ene" terminates a group it indicates the group is attached to two other groups. For example, methylene refers to a —CH$_2$-moiety.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Cyclic amide" refers to any stable 4, 5, 6, 7, 8, 9, or 10 membered monocyclic or bicyclic heterocyclic ring that contains a ring amide (N—C(O)) and is attached via the N of the ring amide. The cyclic amide consists of the amide (NC(O)) moiety, carbon atoms and 0, 1, or 2 additional heteroatoms independently selected from the group consisting of N, O, and S. One or two double bonds can be present in the ring containing the amide. If the cyclic amide is bicyclic then the non-amide containing ring can be aromatic (e.g., benzo, pyrimido, or other heteroaryl). An additional N group, if present, may be N, NH, or N-substituent, depending on the chosen ring and if substituents are recited. The nitrogen and sulfur heteroatoms may optionally be oxidized (e.g., S, S(O), S(O)$_2$, and N—O). The cyclic amides described herein may be substituted on carbon or on a nitrogen atom if the resulting compound is stable.

Alternatively, the cyclic amide is attached via a carbon atom, instead of the amide nitrogen. For these cyclic amides, the amide nitrogen is substituted with a $C_{1-6}$ alkyl group that is optionally substituted with a $C_{3-6}$ cycloalkyl or a $C_{1-3}$ alkylene-$C_{3-6}$ cycloalkyl group.

"Heteroaryl" refers to any stable 5, 6, 7, 8, 9, or 10 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Mammal" and "patient" cover warm blooded mammals that are typically under medical care (e.g., humans and domesticated animals). Examples include feline, canine, equine, bovine, non-human primate, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting its development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts described herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound described herein that is effective when administered alone or in combination to an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Formulations and Dosages

The compounds described herein can be formulated as pharmaceutical compositions and administered to a mammalian host, such as a human patient in a variety of forms adapted to the chosen route of administration, e.g., orally or parenterally, by intravenous (e.g., continuously or bolus), intrathecal, intramuscular, topical, intradermal, intraperitoneal, intraocular, inhalation or subcutaneous routes. Exemplary pharmaceutical compositions are disclosed in "*Rem-*

*ington: The Science and Practice of Pharmacy,"* A. Gennaro, ed., 20th edition, Lippincott, Williams & Wilkins, Philadelphia, Pa.

Thus, the present compounds may be systemically administered, e.g., orally, in combination with a pharmaceutically acceptable carrier/excipient such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The amount of the compound described herein or an active salt or derivative thereof, required for use in treatment will vary not only with the particular compound or salt selected but also with the route of administration, the nature of the condition being treated, and the age and condition of the patient, and will ultimately be at the discretion of the attendant physician or clinician. In general, however, a suitable dose will be in the range of (a) about 1.0-1000 mg/kg of body weight per day, (b) about 10-500 mg/kg of body weight per day, and (c) about 5-20 mg/kg of body weight per day.

For an eye drop, the composition will typically contain an active ingredient at a concentration of generally from 0.000001 to 10% (w/v), also from 0.00001 to 3% (w/v), 0.0001 to 1% (w/v), and 0.001 to 0.1% (w/v) may be instilled to an adult once to several times a day.

For oral administration, the compounds described herein may be administered to an adult once or divided into several times at a dose of generally from 0.001 to 5000 mg per day, also from 0.1 to 2500 mg per day, and from 1 to 1000 mg per day.

For a liquid composition (e.g., in a lotion), the concentration of compounds described herein can be from (a) about 0.1-25 wt % and (b) about 0.5-10 wt %. The concentration in a semi-solid or solid composition such as a gel or a powder can be (a) about 0.1-5 wt % and (b) about 0.5-2.5 wt %.

The compounds described herein can be conveniently administered in unit dosage form; e.g., tablets, caplets, etc., containing (a) about 4-400 mg, (b) about 10-200 mg, and (c) about 20-100 mg of active ingredient per unit dosage form.

The compounds described herein can be administered to achieve peak plasma concentrations of the active compound of (a) about 0.02-20 µM, (b) about 0.1-10 µM, and (c) about 0.5-5 µM. These concentrations may be achieved, for example, by the intravenous injection (e.g., continuously or bolus) of a 0.005-0.5% solution of the active ingredient, or orally administered as a bolus containing about 4-400 mg of the active ingredient.

When a compound described herein is administered in combination with another agent or agents (e.g., co-administered), then the compound described herein and other agent can be administered simultaneously or in any order. They can be administered as a single pharmaceutical composition or as separate compositions. The administration of the compound described herein can be prior to the other agent(s), within minutes thereof, or up to hours (e.g., 24 or 48) or even days after the administration of the other agent(s). For example, the administration of the compound described herein can be within about 24 hours or within about 12 hours.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds described herein may also be administered intravenously (e.g., continuously or bolus) or intraperitoneally by infusion or injection. Solutions of the compounds described herein or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds described herein may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Examples of useful dermatological compositions which can be used to deliver the compounds described herein to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949.

The compounds described herein can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, and atomizers are fully described in pharmaceutical reference books such as *Remington's Pharmaceutical Sciences* Volumes 16 (1980) or 18 (1990) Mack Publishing Co.

The desired dose of the compounds described herein may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Synthesis

The compounds described herein can be prepared in a number of ways known to one skilled in the art of organic synthesis. The compounds described herein can be synthesized using the methods described below, together with synthetic methods known in the art of synthetic organic chemistry, or by variations thereon as appreciated by those skilled in the art. Useful methods include, but are not limited to, those described below. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

One stereoisomer of a compound described herein may be a more potent $A_{2B}$ antagonist than its counterpart(s). Thus, stereoisomers are included herein. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound described herein may also be directly synthesized using a chiral catalyst or a chiral ligand, e.g., Jacobsen, E. *Acc. Chem. Res.* 2000, 33, 421-431 or using other enantio- and diastereoselective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

The following examples are representative of the procedures used to prepare the compounds described herein.

General Procedure:

The compounds described herein can be prepared by methods like those described in P. J. Scammells, et al., J. Med. Chem. 37, 2704-2712 (1994). For example, 1,3-disubstituted-8-(6-chloropyridin-3-yl)xanthine can be reacted with a cyclic amide, such as N-(3-Aminopropyl)-2-pyrrolidinone, to afford the desired intermediate. Reaction of the intermediate with an appropriate acid chloride can afford the desired final product.

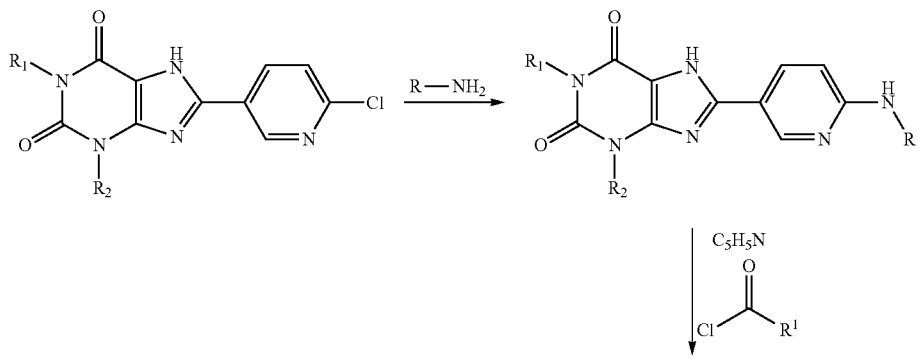

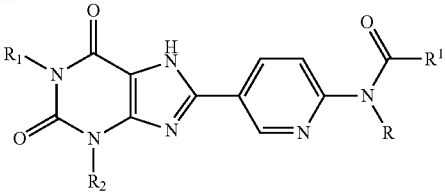

Preparative Example A

Synthesis of 3-(2-methoxyethyl)-8-(6-((3-(2-oxo-1-pyrrolidinyl)propyl)amino)-3-pyridyl)-1-propylxanthine 8-(6-Chloropyridin-3-yl)-3-(2-methoxyethyl)-1-propylxanthine (0.7000 g, 1.92 mmol) was combined with N-(3-aminopropyl)-2-pyrrolidinone (1.094 g, 7.70 mmol) in a pressure flask with or without a small volume of isopropanol. The isopropanol was boiled off, if present, and the solution heated and stirred at 145 to 165° C. until HPLC indicated a complete reaction (~47 hours). The solution was transferred to a flask with DCM (dichloromethane) and silica added. The solvents were removed with a rotary evaporator and the solid was dried under vacuum (<1 mm Hg). The dried compound on silica was dry-packed on a small column for column chromatography. The compound was purified on a chromatography column using a gradient of 0-4% MeOH in DCM. Yield: 0.7000 g, 1.49 mmol, 77.48% yield. HPLC-MS conditions: 40%-80% MeOH (0.1% formic acid)/H$_2$O (0.1% formic acid) 10 min. 5 min. hold, Rt=7.821, LRMS ESI m/z 470.20 (M+1).

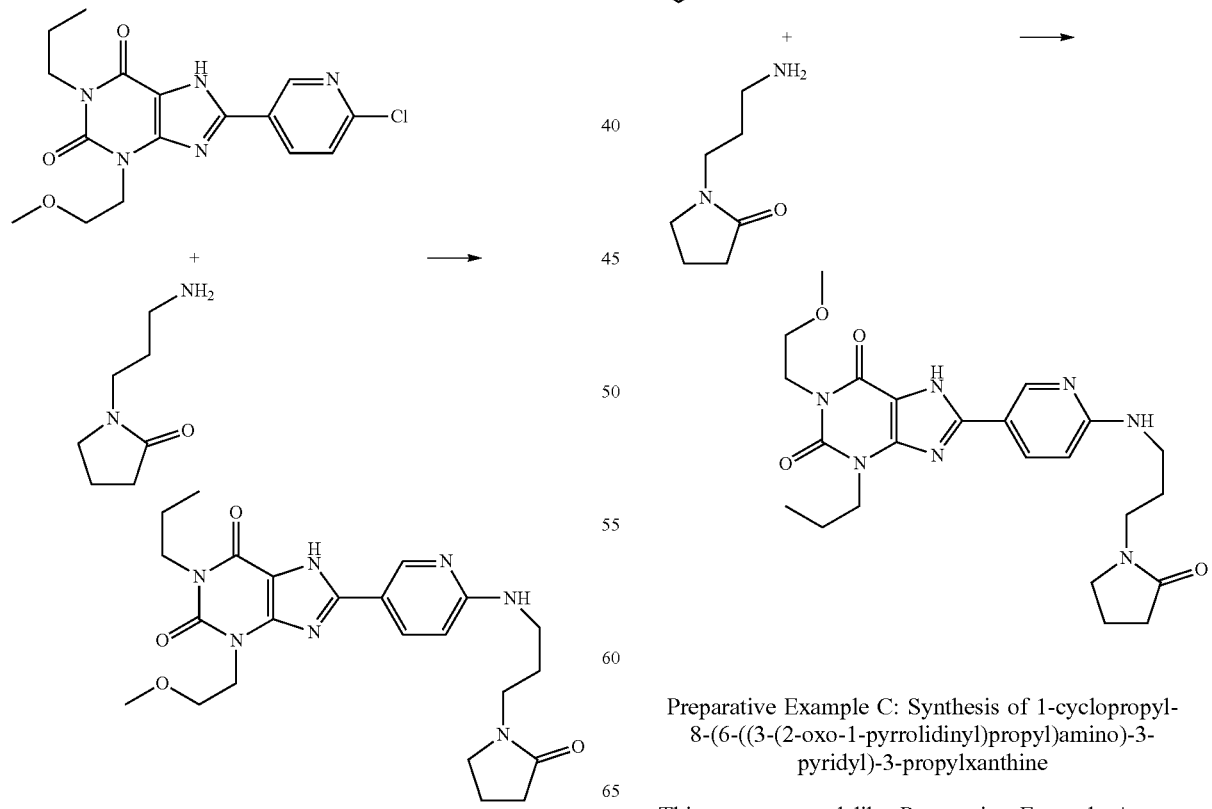

Preparative Example B

Synthesis of 1-(2-methoxyethyl)-8-(6-((3-(2-oxo-1-pyrrolidinyl)propyl)amino)-3-pyridyl)-3-propylxanthine This was prepared like Preparative Example A, except that 8-(6-chloropyridin-3-yl)-1-(2-methoxyethyl)-3-propylxanthine was used as the starting material. Yield: 0.7500 g, 1.60 mmol, 52.83% yield. HPLC-MS conditions: 40%-80% MeOH (0.1% formic acid)/H$_2$O (0.1% formic acid) 10 min. 5 min. hold, Rt=7.659, LRMS ESI m/z 470.20 (M+1).

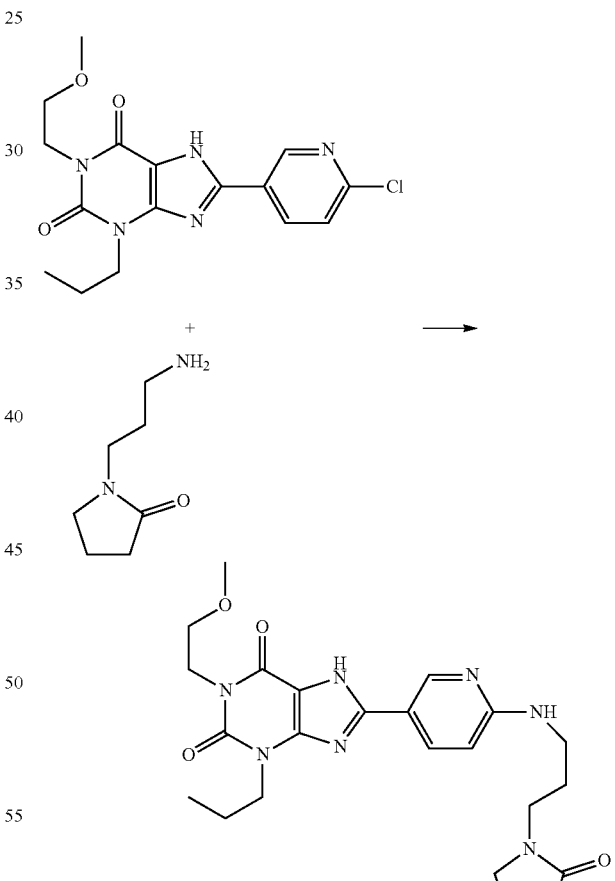

Preparative Example C: Synthesis of 1-cyclopropyl-8-(6-((3-(2-oxo-1-pyrrolidinyl)propyl)amino)-3-pyridyl)-3-propylxanthine This was prepared like Preparative Example A, except that 8-(6-chloropyridin-3-yl)-1-cyclopropyl-3-propylxanthine was used as the starting material. Yield: 0.6470 g, 1.4329 mmol, 33.03%. HPLC-MS conditions: 40%-80% MeOH (0.1% formic acid)/H$_2$O (0.1% formic acid) 10 min. 5 min. hold, Rt=8.292, LRMS ESI m/z 452.15 (M+1).

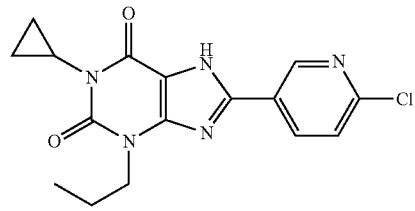

+

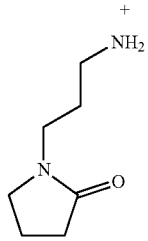

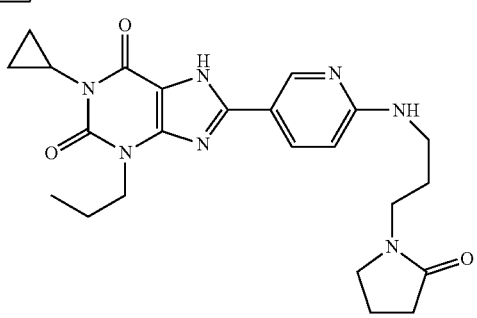

Preparative Example D: Synthesis of 1-(3-methoxypropyl)-8-(6-((3-(2-oxo-1-pyrrolidinyl)propyl)amino)-3-pyridyl)-3-propylxanthine This was prepared like Preparative Example A, except that 8-(6-chloropyridin-3-yl)-1-(3-methoxypropyl)-3-propylxanthine was used as the starting material. Yield: 5.5 g, 11.37 mmoles, 85.95%. HPLC-MS conditions: 40%-80% MeOH (0.1% formic acid)/H$_2$O (0.1% formic acid) 10 min. 5 min. hold, Rt=9.514, LRMS ESI m/z 484.35 (M+1).

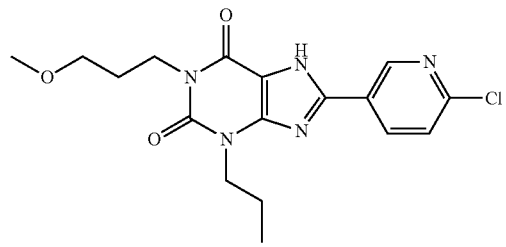

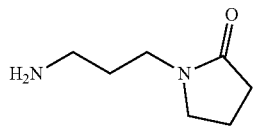

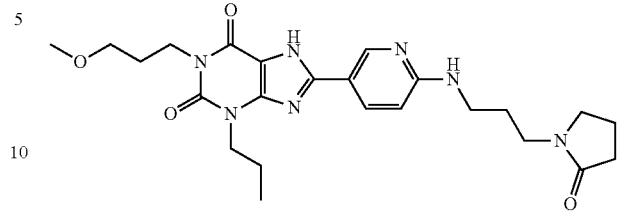

Preparative Example E: Synthesis of 8-(6-(N-(2-methoxyethyl)amino)-3-pyridyl)-1-((2-oxo-1-pyrrolidinyl)propyl)-3-propylxanthine This was prepared like Preparative Example A, except that 8-(6-chloropyridin-3-yl)-1-(2-oxo-1-pyrrolidinyl)propyl)-3-propylxanthine and 2-methoxyethylamine were used as the starting material. Yield: 0.8 g, 1.49 mmoles, 64.24%. HPLC-MS conditions: 40%-80% MeOH (0.1% formic acid)/H$_2$O (0.1% formic acid) 10 min. 5 min. hold, Rt=8.826, LRMS ESI m/z 470.25 (M+1).

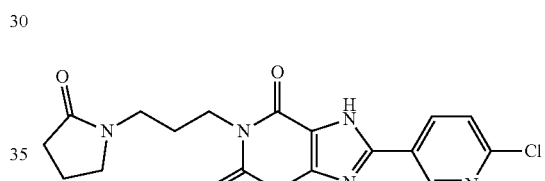

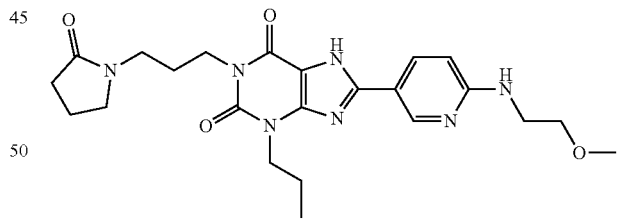

Preparative Example F: Synthesis of 8-(6-((1-Methyl-5-oxo-3-pyrrolidinyl)methylamino)-3-pyridyl)-1-(2-methoxyethyl)-3-propylxanthine This was prepared like Preparative Example A, except that 8-(6-chloropyridin-3-yl)-1-(2-methoxyethyl)-3-propylxanthine and 4-(aminomethyl)-1-methyl-2-pyrrolidinone were used as the starting material. Yield: 0.18 g, 0.40 mmoles, 28.93%. HPLC-MS conditions: 40%-80% MeOH (0.1% formic acid)/H$_2$O (0.1% formic acid) 10 min. 5 min. hold, Rt=8.701, LRMS ESI m/z 456.25 (M+1).

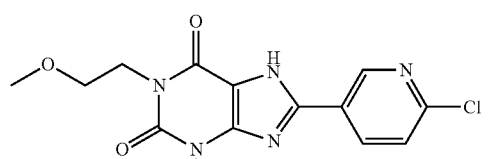

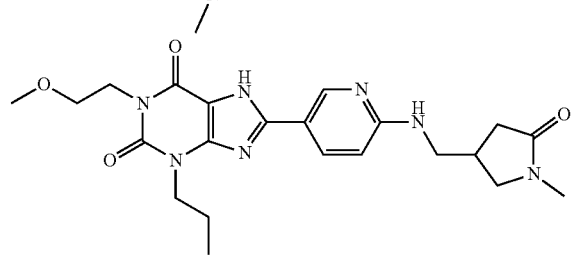

Preparative Example G: Synthesis of 1,3-dicyclopropyl-8-(6-((3-(2-oxo-1-pyrrolidinyl)propyl)amino)-3-pyridyl)xanthine This was prepared like Preparative Example A, except that 8-(6-chloropyridin-3-yl)-1-(3-methoxypropyl)-3-propylxanthine was used as the starting material. Yield: 1.16 g, 2.58 mmmoles, 88.81%. HPLC-MS conditions: 40%-80% MeOH (0.1% formic acid)/H₂O (0.1% formic acid) 10 min. 5 min. hold, Rt=6.804, LRMS ESI m/z 450.2 (M+1).

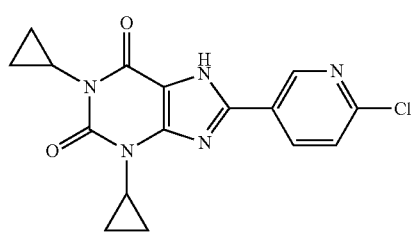

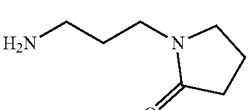

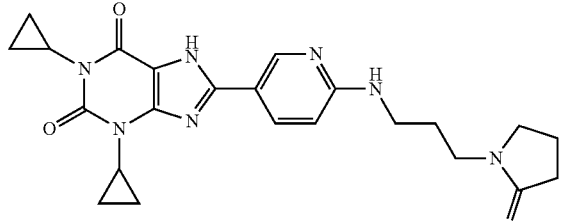

Preparative Example H: Synthesis of 3-(3-methoxypropyl)-8-(6-((3-(2-oxo-1-pyrrolidinyl)propyl)amino)-3-pyridyl)-1-propylxanthine This was prepared like Preparative Example A, except that 8-(6-chloropyridin-3-yl)-3-(3-methoxypropyl)-1-propylxanthine was used as the starting material. Yield: 0.3 g, 0.62 mmmoles, 10.56%. HPLC-MS conditions: 40%-80% MeOH (0.1% formic acid)/H₂O (0.1% formic acid) 10 min. 5 min. hold, Rt=9.378, LRMS ESI m/z 484.3 (M+1).

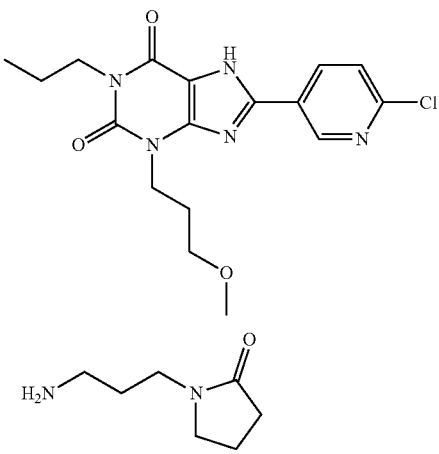

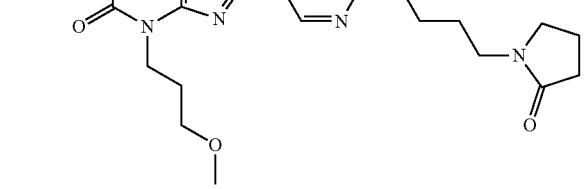

Preparative Example I: Synthesis of 1-(2-acetylaminoethyl)-8-(6-((3-(2-oxo-1-pyrrolidinyl)propyl)amino)-3-pyridyl)-3-propylxanthine This was prepared like Preparative Example A, except that 8-(6-chloropyridin-3-yl)-1-(2-acetylaminoethyl)-3-propylxanthine was used as the starting material. Yield: 0.2 g, 0.4 mmoles, 39.35%. HPLC-MS conditions: 40%-80% MeOH (0.1% formic acid)/H₂O (0.1% formic acid) 10 min. 5 min. hold, Rt=6.546, LRMS ESI m/z 497.35 (M+1).

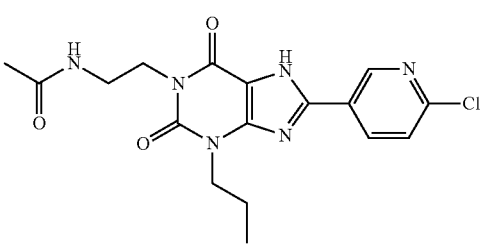

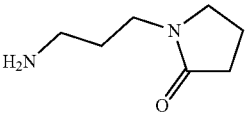

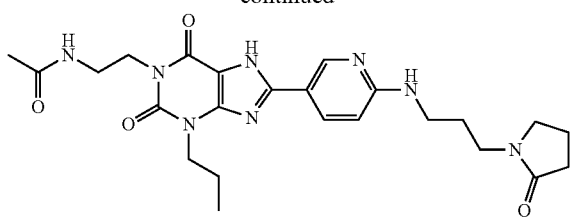

Preparative Example J: Synthesis of 8-(6-(N-ethyl-amino)-3-pyridyl)-1-((2-oxo-1-pyrrolidinyl)propyl)-3-propylxanthine This was prepared like Preparative Example A, except that 8-(6-chloropyridin-3-yl)-1-(2-oxo-1-pyrrolidinyl)propyl)-3-propylxanthine and ethylamine were used as the starting material. Yield: 0.500 g, 1.14 mmoles, 29.71% HPLC-MS conditions: 40%-80% MeOH (0.1% formic acid)/H$_2$O (0.1% formic acid) 10 min. 5 min. hold, Rt=8.875, LRMS ESI m/z 440.25 (M+1).

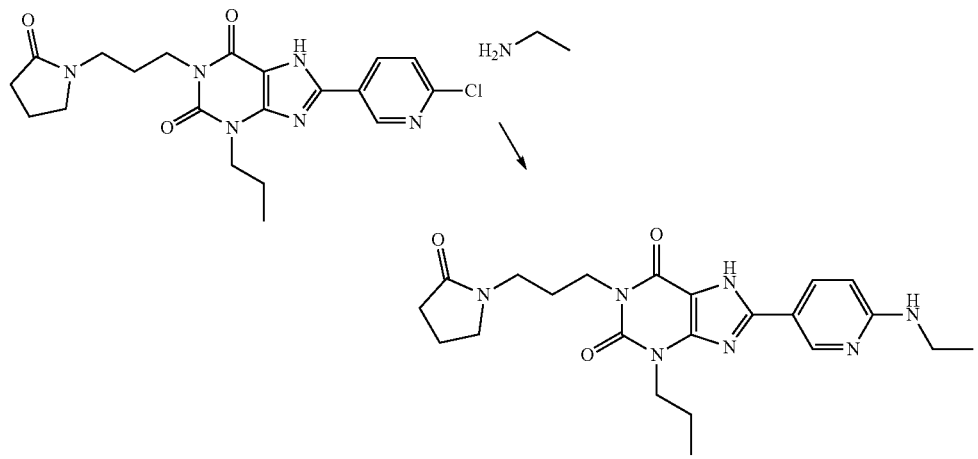

Preparative Example K: Synthesis of 1-(3-methoxypropyl)-8-(6-((1-Methyl-5-oxo-3-pyrrolidinyl)methylamino)-3-pyridyl)-3-propylxanthine This was prepared like Preparative Example A, except that 8-(6-chloropyridin-3-yl)-1-(3-methoxypropyl)-3-propylxanthine and 4-(aminomethyl)-1-methyl-2-pyrrolidinone were used as the starting material. Yield: 0.265 g, 0.56 mmoles, 42.65% HPLC-MS conditions: 40%-80% MeOH (0.1% formic acid)/H$_2$O (0.1% formic acid) 10 min. 5 min. hold, Rt=10.696, LRMS ESI m/z 470.20 (M+1).

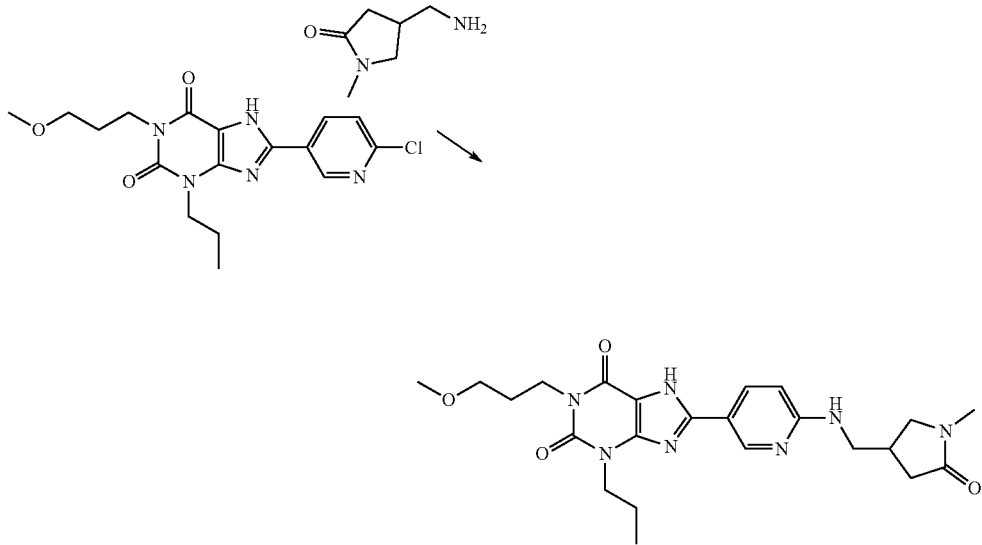

Preparative Example L: Synthesis of 1-cyclopropyl-8-(6-(((1-methyl-5-oxo-3-pyrrolidinyl)methyl-amino))-3-pyridyl)-3-propylxanthine This was prepared like Preparative Example A, except that 8-(6-chloropyridin-3-yl)-1-cyclopropyl-3-propylxanthine and 4-(aminomethyl)-1-methyl-2-pyrrolidinone were used as the starting material. Yield: 0.600 g, 1.37 mmoles, 94.84% HPLC-MS conditions: 40%-80% MeOH (0.1% formic acid)/H$_2$O (0.1% formic acid) 10 min. 5 min. hold, Rt=10.059, LRMS ESI m/z 438.15 (M+1).

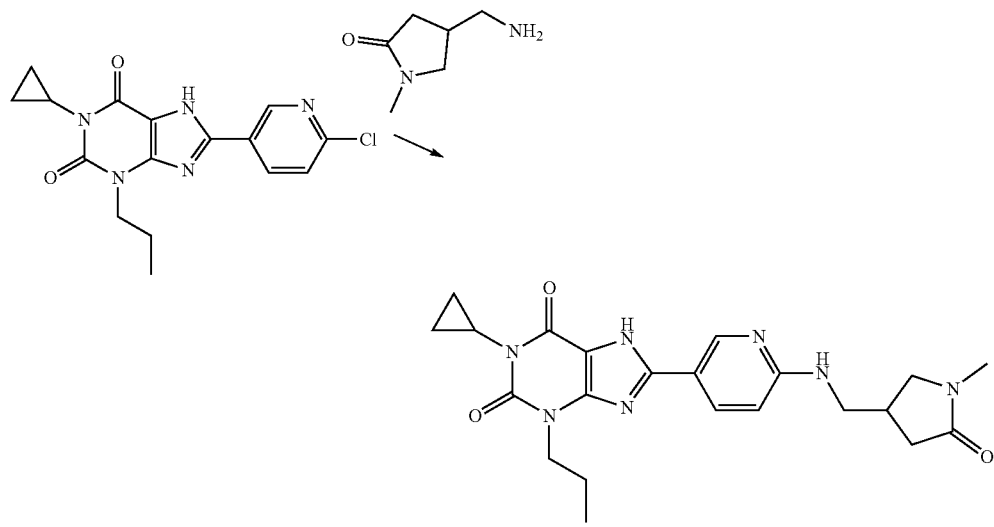

Preparative Example M: Synthesis of 1,3-dicyclopropyl-8-(6-(((1-methyl-5-oxo-3-pyrrolidinyl)methylamino))-3-pyridyl)xanthine This was prepared like Preparative Example A, except that 8-(6-chloropyridin-3-yl)-1-(3-methoxypropyl)-3-propylxanthine and 4-(aminomethyl)-1-methyl-2-pyrrolidinone were used as the starting material. Yield: 1.035 g, 2.38 mmoles, 90.78% HPLC-MS conditions: 40%-80% MeOH (0.1% formic acid)/H$_2$O (0.1% formic acid) 10 min. 5 min. hold, Rt=7.831, LRMS ESI m/z 436.20 (M+1).

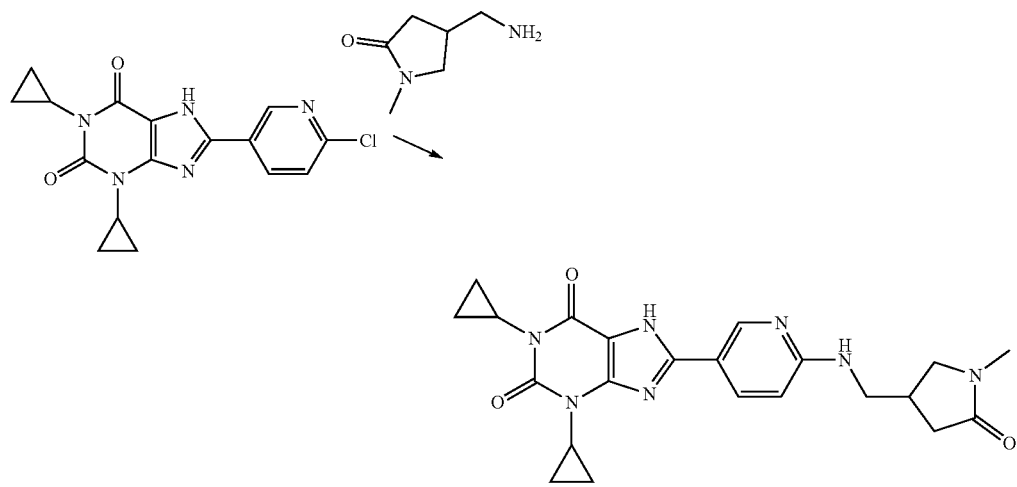

Example 1: 8-(6-{[3-(2-Oxo-1-pyrrolidinyl)propyl] (3,4-difluorophenyl)carbonylamino}-3-pyridyl)-1-cyclopropyl-3-propylxanthine In a 50 mL flask, Preparative Example C (0.1000 g, 0.22 mmol) was heated in dry pyridine (15 mL) at 40° C. until dissolved, approx. 5 minutes. To the solution, 3,4-difluorobenzoyl chloride (0.056 mL, 0.44 mmol) was added, and the reaction stirred at 40° C. for 48 hours. HPLC indicated that the reaction was complete. Water was added to quench the reaction, and the solvents was removed in vacuo. The resulting solid was dissolved in DCM/MeOH and bound to silica for column chromatography (26 g). The column was eluted with 0-7% MeOH in DCM and like fractions were collected and dried in vacuo. Yield: 0.0901 g, 0.15 mmol, 68.76% yield. HPLC-MS conditions: 40%-80% MeOH (0.1% formic acid)/$H_2O$ (0.1% formic acid) 10 min. 5 min. hold, Rt=12.570, LRMS ESI m/z 592.25 (M+1).

Example 2: 8-(6-{[3-(2-Oxo-1-pyrrolidinyl)propyl] (4-fluorophenyl)carbonylamino}-3-pyridyl)-1-cyclopropyl-3-propylxanthine In a 50 mL flask, Preparative Example C (0.1000 g, 0.22 mmol) was stirred in dry pyridine (15 mL) at 40° C. until dissolved, about 5 minutes. 4-Fluorobenzoyl chloride (0.05 mL, 0.44 mmol) was added, and the reaction was allowed to stir at 40° C. for four days. More acid chloride was added, and the reaction continued to stir overnight. Water was added to quench the reaction, and the solvent was removed in vacuo. The resulting solid was dissolved in DCM/MeOH and bound to silica for column chromatography. Yield: 0.0855 g, 0.14 mmol, 67.86% yield. HPLC-MS conditions: 40%-80% MeOH (0.1% formic acid)/$H_2O$ (0.1% formic acid) 10 min. 5 min. hold, Rt=12.113, LRMS ESI m/z 574.25 (M+1).

Example 3: 8-(6-{[3-(2-Oxo-1-pyrrolidinyl)propyl] (6-fluoro-3-pyridyl)carbonylamino}-3-pyridyl)-1-cyclopropyl-3-propylxanthine In a 50 mL flask, Preparative Example C (0.1000 g, 0.22 mmol) was heated in dry pyridine (15 mL) at 40° C. until dissolved, approx. 5 minutes. To the solution, 6-fluoronicotinoyl chloride (0.050 mL, 0.44 mmol) was added and the reaction stirred at 40° C. for 24 hours. HPLC indicated that the reaction was complete. Water was added to quench the reaction, and the solvents was removed in vacuo. The resulting solid was dissolved in DCM/MeOH and bound to silica for column chromatography (26 g). Yield: 0.0794 g, 0.14 mmol, 62.39% yield. HPLC-MS conditions: 40%-80% MeOH (0.1% formic acid)/$H_2O$ (0.1% formic acid) 10 min. 5 min. hold, Rt=10.790, LRMS ESI m/z 575.25 (M+1).

Example 4: 8-(6-{[3-(2-Oxo-1-pyrrolidinyl)propyl] (3,4-difluorophenyl)carbonylamino}-3-pyridyl)-1-(2-methoxyethyl)-3-propylxanthine In a 50 mL flask, Preparative Example B (0.100 g, 0.21 mmol) was combined with 3,4-difluorobenzoyl chloride (0.054 mL, 0.43 mmol) in dry pyridine (15 mL). The reaction stirred at 40° C. for 24 hours. HPLC indicated that the reaction was complete. Water (~2 mL) was added to quench the reaction. The water and pyridine were removed in vacuo, and the resulting oil was dissolved in DCM for purification by silica column chromatography (26 g). The column was eluted with 0-5% MeOH in DCM. Like fractions were collected and dried in vacuo. Yield: 0.128 g, 0.21 mmol, 98.58% yield. HPLC-MS conditions: 40%-80% MeOH (0.1% formic acid)/$H_2O$ (0.1% formic acid) 10 min. 5 min. hold, Rt=12.277, LRMS ESI m/z 610.20 (M+1).

Example 5: 8-(6-{[3-(2-Oxo-1-pyrrolidinyl)propyl] (4-fluorophenyl)carbonylamino}-3-pyridyl)-1-(2-methoxyethyl)-3-propylxanthine In a 50 mL flask, Preparative Example B (0.100 g, 0.21 mmol) was combined with 4-fluorobenzoyl chloride (0.049 mL, 0.43 mmol) in dry pyridine (15 mL). The reaction stirred at 40° C. for 24 hours. HPLC indicated that the reaction was complete. Water was added to quench the reaction and the solvent was removed in vacuo. The resulting solid was dissolved in DCM for column chromatography (26 g). The column was eluted with 0-5% MeOH in DCM. Like fractions were collected and dried. Yield: 0.0855 g, 0.14 mmol, 67.86% yield. HPLC-MS conditions: 40%-80% MeOH (0.1% formic acid)/$H_2O$ (0.1% formic acid) 10 min. 5 min. hold, Rt=11.815, LRMS ESI m/z 592.20 (M+1).

Example 6: 8-(6-{[3-(2-Oxo-1-pyrrolidinyl)propyl] (6-fluoro-3-pyridyl)carbonylamino}-3-pyridyl)-1-(2-methoxyethyl)-3-propylxanthine In a 50 mL flask, Preparative Example B (0.1000 g, 0.21 mmol) was dissolved in dry pyridine (15 mL). To the solution, 6-fluoronicotinoyl chloride (0.049 mL, 0.43 mmol) was added, and the reaction stirred at 40° C. for 24 hours. HPLC indicated that the reaction was complete. Water was added to quench the reaction, and the solvent was removed in vacuo. The resulting solid was dissolved in DCM/MeOH and bound to silica for purification. The chromatography column (26 g) was eluted with 0-5% MeOH in DCM, and like fractions were collected and dried in vacuo. Yield: 0.0829 g, 0.14 mmol, 65.68% yield. HPLC-MS conditions: 40%-80% MeOH (0.1% formic acid)/$H_2O$ (0.1% formic acid) 10 min. 5 min. hold, Rt=10.547, LRMS ESI m/z 593.25 (M+1).

Example 7: 8-(6-{[3-(2-Oxo-1-pyrrolidinyl)propyl] (3,4-difluorophenyl)carbonylamino}-3-pyridyl)-3-(2-methoxyethyl)-1-propylxanthine In a 50 mL flask, Preparative Example A (0.100 g, 0.21 mmol) was combined with 3,4-difluorobenzoyl chloride (0.054 mL, 0.43 mmol) in dry pyridine (15 mL). The reaction was stirred at 40° C. for 24 hours. Water (~2 mL) was added to quench the reaction. The water and pyridine were removed in vacuo, and the resulting oil was dissolved in DCM. The compound was purified on a 26 g silica chromatography column and eluted with 0-3% MeOH in DCM. Like fractions were collected. Yield: 0.129 g, 0.21 mmol, 99.36% yield. HPLC-MS conditions: 40%-80% MeOH (0.1% formic acid)/$H_2O$ (0.1% formic acid) 10 min. 5 min. hold, Rt=12.010, LRMS ESI m/z 610.25 (M+1).

Example 8: 8-(6-{[3-(2-Oxo-1-pyrrolidinyl)propyl] (4-fluorophenyl)carbonylamino}-3-pyridyl)-3-(2-methoxyethyl)-1-propylxanthine In a 50 mL flask, Preparative Example A (0.100 g, 0.21 mmol) was combined with 4-fluorobenzoyl chloride (0.049 mL, 0.43 mmol) in dry pyridine (15 mL). The reaction stirred at 40° C. for 24 hours. HPLC indicated that the reaction was not complete and more acid chloride was added, and the reaction stirred at 40° C. for an additional 24 hours. Water (2 mL) was added to quench the reaction, and the solution was dried in vacuo to a solid. Additional water was added and removed in vacuo. The resulting solid was dissolved in DCM and purified on a 26 g silica chromatography column, with a gradient of 0-4% MeOH in DCM. Like fractions were collected and dried. Yield: 0.077 g, 0.13 mmol, 61.11% yield. HPLC-MS conditions: 40%-80% MeOH (0.1% formic acid)/H$_2$O (0.1% formic acid) 10 min. 5 min. hold, Rt=11.483, LRMS ESI m/z 592.20 (M+1).

Example 9: 8-(6-{[3-(2-Oxo-1-pyrrolidinyl)propyl](6-fluoro-3-pyridyl)carbonylamino}-3-pyridyl)-3-(2-methoxyethyl)-1-propylxanthine In a 50 mL flask, Preparative Example A (0.100 g, 0.21 mmol) was combined with 6-fluoronicotinoyl chloride (0.049 mL, 0.43 mmol) in dry pyridine (15 mL). The reaction stirred at 40° C. for 24 hours. HPLC indicated that the reaction was not complete. More acid chloride was added, and the reaction continued stirring for 24 hours. Additional acid chloride was added, and the reaction stirred for 24 more hours. The reaction was quenched with water (2 mL), and the solvents were removed in vacuo. DCM was added and purified by column chromatography. The 26 g column was eluted with 0-3% MeOH in DCM. Like fractions were collected and dried. Yield: 0.055 g, 0.09 mmol, 43.58% yield. HPLC-MS conditions: 40%-80% MeOH (0.1% formic acid)/H$_2$O (0.1% formic acid) 10 min. 5 min. hold, Rt=9.802, LRMS ESI m/z 593.25 (M+1).

Example 10: 8-(6-{[3-(2-Oxo-1-pyrrolidinyl)propyl](3,4-difluorophenyl)carbonylamino}-3-pyridyl)-1-(3-methoxypropyl)-3-propylxanthine In a 50 mL flask, Preparative Example D (0.150 g, 0.32 mmol) was combined with 3,4-difluorobenzoyl chloride (0.080 mL, 0.64 mmol) in dry pyridine (10 mL) and dry DCM (1.58 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-5% MeOH in DCM. Like fractions were collected and dried in vacuo. Yield: 0.1728 g, 0.28 mmol, 86.73% yield. HPLC-MS conditions: 40%-85% MeOH (0.1% formic acid)/H$_2$O (0.1% formic acid) 10 min. 5 min. hold, Rt=12.994, LRMS ESI m/z 624.35 (M+1).

Example 11: 8-{6-[(2-Methoxyethyl)(3,4-difluorophenyl)carbonylamino]-3-pyridyl}-1-[3-(2-Oxo-1-pyrrolidinyl)propyl]-3-propylxanthine In a 50 mL flask, Preparative Example E (0.150 g, 0.32 mmol) was combined with 3,4-difluorobenzoyl chloride (0.080 mL, 0.64 mmol) in dry pyridine (10 mL) and dry DCM (1.58 mL). The reaction stirred at 40° C. for 24 hours. Water (~2 mL) was added to quench the reaction. The solvent was removed in vacuo, and the resulting oil was dissolved in DCM for purification by silica column chromatography. The column was eluted with 0-5% MeOH in DCM. Like fractions were collected and dried in vacuo. Yield: 0.105 g, 0.17 mmol, 53.92% yield. HPLC-MS conditions: 40%-85% MeOH (0.1% formic acid)/H$_2$O (0.1% formic acid) 10 min. 5 min. hold, Rt=12.632, LRMS ESI m/z 610.25 (M+1).

Example 12: 8-(6-{N-[3-(2-Oxo-1-pyrrolidinyl)propyl](6-fluoro-3-pyridyl)carbonylamino}-3-pyridyl)-1-(3-methoxypropyl)-3-propylxanthine In a 50 mL flask, Preparative Example D (0.1500 g, 0.31 mmol) was dissolved in dry pyridine (10 mL) and dry DCM (1.585 mL). To the solution, 6-fluoronicotinoyl chloride (0.049 mL, 0.43 mmol) was added, and the reaction stirred at 40 C for 24 hours. Water was added to quench the reaction, and the solvent was removed in vacuo. The resulting solid was dissolved in DCM/MeOH and bound to silica for column chromatography. The column was eluted with 0-5% MeOH in DCM. Like fractions were collected and dried in vacuo. Yield: 0.159 g, 0.26 mmol, 67.41% yield. HPLC-MS conditions: 40%-80% MeOH (0.1% formic acid)/H$_2$O (0.1% formic acid) 10 min. 5 min. hold, Rt=12.327, LRMS ESI m/z 607.3 (M+1).

Example 13: 8-{6-[N-(2-Methoxyethyl)[6-(trifluoromethyl)-3-pyridyl]carbonylamino]-3-pyridyl}-1-[3-(2-Oxo-1-pyrrolidinyl)propyl]-3-propylxanthine In a 50 mL flask, Preparative Example E (0.150 g, 0.32 mmol) was combined with 3,4-difluorobenzoyl chloride (0.080 mL, 0.64 mmol) in dry pyridine (10 mL) and dry DCM (1.58 mL). The reaction stirred at 40° C. for 24 hours. Water (~2 mL) was added to quench the reaction. The solvent was removed in vacuo, and the resulting oil was dissolved in DCM for purification by silica column chromatography. The column was eluted with 0-5% MeOH in DCM. Like fractions were collected and dried in vacuo. Yield: 0.114 g, 0.18 mmol, 55.53% yield. HPLC-MS conditions: 40%-80% MeOH (0.1% formic acid)/H$_2$O (0.1% formic acid) 10 min. 5 min. hold, Rt=13.061, LRMS ESI m/z 643.25 (M+1).

Example 14: 8-{6-[N-(2-Methoxyethyl)[6-fluoro-3-pyridyl]carbonylamino]-3-pyridyl}-1-[3-(2-Oxo-1-pyrrolidinyl)propyl]-3-propylxanthine In a 50 mL flask, Preparative Example E (0.200 g, 0.43 mmol) was combined with 6-fluoronicotinoyl chloride (0.194 mL, 1.7 mmol) in dry pyridine (10 mL) and dry DCM (1.58 mL). The reaction stirred at 40° C. for 24 hours. Water (~2 mL) was added to quench the reaction. The solvent was removed in vacuo, and the resulting oil was dissolved in DCM for purification by silica column chromatography. The column was eluted with 0-5% MeOH in DCM. Like fractions were collected and dried in vacuo. Yield: 0.130 g, 0.22 mmol, 51.50% yield. HPLC-MS conditions: 40%-80% MeOH (0.1% formic acid)/H$_2$O (0.1% formic acid) 10 min. 5 min. hold, Rt=11.996, LRMS ESI m/z 593.25 (M+1).

Example 15: 8-(6-{[(1-Methyl-5-oxo-3-pyrrolidinyl)methyl](3,4-difluorophenyl)carbonylamino}-3-pyridyl)-1-(2-methoxyethyl)-3-propylxanthine In a 50 mL flask, Preparative Example F (0.100 g, 0.21 mmol) was combined with 3,4-difluorobenzoyl chloride (0.054 mL, 0.43 mmol) in dry pyridine (15 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-5% MeOH in DCM. Like fractions were collected and dried in vacuo. Yield: 0.124 g, 0.21 mmol, 52.34% yield. HPLC-MS conditions: 40%-80%

MeOH (0.1% formic acid)/H$_2$O (0.1% formic acid) 10 min. 5 min. hold, Rt=13.310, LRMS ESI m/z 596.25 (M+1).

Example 16: 8-(6-{[3-(2-Oxo-1-pyrrolidinyl)propyl](3,4-difluorophenyl)carbonylamino}-3-pyridyl)-1,3-dicyclopropylxanthine In a 50 mL flask, Preparative Example G (0.150 g, 0.33 mmol) was combined with 3,4-difluorobenzoyl chloride (0.084 mL, 0.67 mmol) in dry pyridine (15 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-5% MeOH in DCM. Like fractions were collected and dried in vacuo. Yield: 0.0777 g, 0.13 mmol, 39.49% yield. HPLC-MS conditions: 40%-80% MeOH (0.1% formic acid)/H$_2$O (0.1% formic acid) 10 min. 5 min. hold, Rt=12.581, LRMS ESI m/z 590.20 (M+1).

Example 17: 8-(6-{[3-(2-Oxo-1-pyrrolidinyl)propyl](6-fluoro-3-pyridyl)carbonylamino}-3-pyridyl)-1,3-dicyclopropylxanthine In a 50 mL flask, Preparative Example G (0.150 g, 0.33 mmol) was combined with 6-fluoronicotinoyl chloride (0.076 mL, 0.67 mmol) in dry pyridine (15 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-7% MeOH in DCM. Like fractions were collected and dried in vacuo. Yield: 0.105 g, 0.18 mmol, 54.95% yield. HPLC-MS conditions: 40%-80% MeOH (0.1% formic acid)/H$_2$O (0.1% formic acid) 10 min. 5 min. hold, Rt=10.436, LRMS ESI m/z 573.30 (M+1).

Example 18: 8-(6-{[3-(2-Oxo-1-pyrrolidinyl)propyl](cyclopropyl)carbonylamino}-3-pyridyl)-1-(3-methoxypropyl)-3-propylxanthine In a 50 mL flask, Preparative Example D (0.150 g, 0.31 mmol) was combined with cyclopropanecarbonyl chloride (0.056 mL, 0.62 mmol) in dry pyridine (10 mL) and dry DCM (1.58 mL). The reaction stirred at 40° C. for 24 hours. Water (~2 mL) was added to quench the reaction. The solvent was removed in vacuo, and the resulting oil was dissolved in DCM for purification by silica column chromatography. The column was eluted with 0-5% MeOH in DCM. Like fractions were collected and dried in vacuo. Yield: 0.147 g, 0.27 mmol, 86.02% yield. HPLC-MS conditions: 40%-80% MeOH (0.1% formic acid)/H$_2$O (0.1% formic acid) 10 min. 5 min. hold, Rt=13.270, LRMS ESI m/z 552.4 (M+1).

Example 19: 8-(6-{[3-(2-Oxo-1-pyrrolidinyl)propyl](tert-butyl)carbonylamino}-3-pyridyl)-1-(3-methoxypropyl)-3-propylxanthine In a 50 mL flask, Preparative Example D (0.150 g, 0.31 mmol) was combined with trimethylacetyl chloride (0.076 mL, 0.62 mmol) in dry pyridine (10 mL) and dry DCM (1.58 mL). The reaction stirred at 40° C. for 24 hours. Water (~2 mL) was added to quench the reaction. The solvent was removed in vacuo, and the resulting oil was dissolved in DCM for purification by silica column chromatography. The column was eluted with 0-5% MeOH in DCM. Like fractions were collected and dried in vacuo. Yield: 0.1611 g, 0.28 mmol, 91.49% yield. HPLC-MS conditions: 40%-85% MeOH (0.1% formic acid)/H$_2$O (0.1% formic acid) 10 min. 5 min. hold, Rt=13.223, LRMS ESI m/z 568.30 (M+1).

Example 20: 8-(6-{N-[3-(2-Oxo-1-pyrrolidinyl)propyl](6-trifluoromethyl-3-pyridyl)carbonylamino}-3-pyridyl)-1-(3-methoxypropyl)-3-propylxanthine In a 50 mL flask, Preparative Example D (0.150 g, 0.31 mmol) was combined with 6-(trifluoromethyl)nicotinoyl chloride (0.045 mL, 0.62 mmol) in dry pyridine (10 mL) and dry DCM (1.58 mL). The reaction stirred at 40° C. for 24 hours. Water (~2 mL) was added to quench the reaction. The solvent was removed in vacuo, and the crude was bound to silica for column chromatography. The column was eluted with 0-5% MeOH in DCM. Like fractions were collected and dried in vacuo. Yield: 0.1291 g, 0.20 mmol, 63.38% yield. HPLC-MS conditions: 40%-80% MeOH (0.1% formic acid)/H$_2$O (0.1% formic acid) 10 min. 5 min. hold, Rt=13.828, LRMS ESI m/z 657.35 (M+1).

Example 21: 8-(6-{[3-(2-Oxo-1-pyrrolidinyl)propyl](cyclopentyl)carbonylamino}-3-pyridyl)-1-(3-methoxypropyl)-3-propylxanthine In a 50 mL flask, Preparative Example D (0.150 g, 0.31 mmol) was dissolved in dry pyridine (10 mL) and dry DCM (1.58 mL). Cyclopentanecarbonyl chloride (0.151 mL, 1.24 mmol) was added, and the reaction stirred at 40° C. for 24 hours. Water (~2 mL) was added to quench the reaction. The solvent was removed in vacuo, and the crude was bound to silica for column chromatography. The column was eluted with 0-5% MeOH in DCM. Like fractions were collected and dried in vacuo. Yield: 0.170 g, 0.29 mmol, 94.38% yield. HPLC-MS conditions: 40%-85% MeOH (0.1% formic acid)/H$_2$O (0.1% formic acid) 10 min. 5 min. hold, Rt=13.684, LRMS ESI m/z 580.35 (M+1).

Example 22: 8-(6-{N-[3-(2-Oxo-1-pyrrolidinyl)propyl](6-fluoro-3-pyridyl)carbonylamino}-3-pyridyl)-3-(3-methoxypropyl)-1-propylxanthine In a 50 mL flask, Preparative Example H (0.1500 g, 0.31 mmol) was dissolved in dry pyridine (10 mL) and dry DCM (1.585 mL). To the solution, 6-Fluoronicotinoyl Chloride (0.049 mL, 0.43 mmol) was added, and the reaction stirred at 40 C for 24 hours. Water was added to quench the reaction, and the solvent was removed in vacuo. The resulting solid was dissolved in DCM/MeOH and bound to silica for column chromatography. The column was eluted with 0-5% MeOH in DCM. Like fractions were collected and dried in vacuo. Yield: 0.159 g, 0.26 mmol, 84.49% yield. HPLC-MS conditions: 40%-80% MeOH (0.1% formic acid)/H$_2$O (0.1% formic acid) 10 min. 5 min. hold, Rt=12.255, LRMS ESI m/z 607.40 (M+1).

Example 23: 8-(6-{[3-(2-Oxo-1-pyrrolidinyl)propyl](6-fluoro-3-pyridyl)carbonylamino}-3-pyridyl)-1-(2-acetylaminoethyl)-3-propylxanthine In a 50 mL flask, Preparative Example I (0.1500 g, 0.31 mmol) was dissolved in dry pyridine (10 mL) and dry DCM (1.585 mL). To the solution, 6-Fluoronicotinoyl Chloride (0.049 mL, 0.43 mmol) was added, and the reaction stirred at 40 C for 24 hours. Water was added to quench the reaction, and the solvent was removed in vacuo. The resulting solid was dissolved in DCM/MeOH and bound to silica for column chromatography. The column was eluted with 0-5% MeOH in DCM. Like fractions were collected and dried in vacuo. Yield: 0.107 g, 0.17 mmol, 85.75% yield. HPLC-MS conditions: 40%-80% MeOH (0.1% formic acid)/$H_2O$ (0.1% formic acid) 10 min. 5 min. hold, Rt=10.192, LRMS ESI m/z 620.40 (M+1).

Example 24: 8-(6-{[3-(2-Oxo-1-pyrrolidinyl)propyl] (3-methoxyphenyl)carbonylamino}-3-pyridyl)-1,3-dicyclopropylxanthine In a 50 mL flask, Preparative Example G (0.150 g, 0.33 mmol) was combined with 3-Methoxybenzoyl chloride (0.114 g, 0.67 mmol) in dry pyridine (15 mL). The reaction stirred at 40° C. for 24 hours. Water (~2 mL) was added to quench the reaction. The water and pyridine were removed in vacuo, and the resulting solid was dissolved in DCM/MeOH and bound to silica for column chromatography. The column was eluted with 0-5% MeOH in DCM. Like fractions were collected and dried in vacuo. Yield: HPLC-MS conditions: 40%-80% MeOH (0.1% formic acid)/$H_2O$ (0.1% formic acid) 10 min. 5 min. hold, Rt=11.741, LRMS ESI m/z 584.25 (M+1).

Example 25: 8-(6-{[3-(2-Oxo-1-pyrrolidinyl)propyl] (6-chloro-3-pyridyl)carbonylamino}-3-pyridyl)-1,3-dicyclopropylxanthine In a 50 mL flask, Preparative Example G (0.150 g, 0.33 mmol) was combined with 6-Chloronicotinoyl chloride (0.114 g, 0.67 mmol) in dry pyridine (15 mL). The reaction stirred at 40° C. for 24 hours. Water (~2 mL) was added to quench the reaction. The water and pyridine were removed in vacuo. The resulting solid was dissolved in DCM/MeOH and bound to silica for column chromatography. The column was eluted with 0-5% MeOH in DCM. Like fractions were collected and dried in vacuo. Yield: 0.114 g, 0.19 mmol, 58.09% yield. HPLC-MS conditions: 40%-80% MeOH (0.1% formic acid)/$H_2O$ (0.1% formic acid) 10 min. 5 min. hold, Rt=11.123, LRMS ESI m/z 589.25 (M+1).

Example 26: 8-(6-{[3-(2-Oxo-1-pyrrolidinyl)propyl] (3-fluoro-4-methoxyphenyl)carbonylamino}-3-pyridyl)-1,3-dicyclopropylxanthine In a 50 mL flask, Preparative Example G (0.150 g, 0.33 mmol) was combined with 6-Fluoronicotinoyl Chloride (0.076 mL, 0.67 mmol) in dry pyridine (15 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-7% MeOH in DCM. Like fractions were collected and dried in vacuo. Yield: 0.105 g, 0.18 mmol, 54.95% yield. HPLC-MS conditions: 40%-80% MeOH (0.1% formic acid)/$H_2O$ (0.1% formic acid) 10 min. 5 min. hold, Rt=11.711, LRMS ESI m/z 602.30 (M+1).

Example 27: 8-(6-{N-[3-(2-Oxo-1-pyrrolidinyl) propyl](6-chloro-3-pyridyl)carbonylamino}-3-pyridyl)-1-(3-methoxypropyl)-3-propylxanthine In a 50 mL flask, Preparative Example D (0.150 g, 0.31 mmol) was combined with dry pyridine (10 mL), 6-chloronicotinyl chloride (0.114 g, 0.33 mmol) and dry DCM (2 mL). The reaction stirred at 40° C. for 24 hours. The pyridine was removed in vacuo, remaining residue was placed on high vacuum to remove traces of pyridine. The crude solid was dissolved in DCM/MeOH and adhered to silica for column chromatography. Then it was purified on a column of silica (26 g). The column was eluted with 0-8% MeOH in DCM. Like fractions were collected and dried in vacuo. Yield: 0.154 g, 0.25 mmol, 79.68% yield. HPLC-MS conditions: 40%-80% MeOH (0.1% formic acid)/$H_2O$ (0.1% formic acid) 10 min. 5 min. hold, Rt=12.974, LRMS ESI m/z 623.30 (M+1).

Example 28: 8-(6-{N-[3-(2-Oxo-1-pyrrolidinyl) propyl](6-chloro-3-pyridyl)carbonylamino}-3-pyridyl)-1-(2-methoxyethyl)-3-propylxanthine In a 50 mL flask, Preparative Example B (0.150 g, 0.32 mmol) was combined with 6-Chloronicotinoyl Chloride (0.112 g, 0.64 mmol) in dry pyridine (15 mL). The reaction stirred at 40° C. for 24 hours. Water (~2 ml) was added to quench the reaction, and the solvent was removed in vacuo. The resulting solid was dissolved in DCM for column chromatography. The column was eluted with 0-5% MeOH in DCM. Like fractions were collected and dried. Yield: 0.120 g, 0.20 mmol, 63.49% yield. HPLC-MS conditions: 40%-80% MeOH (0.1% formic acid)/$H_2O$ (0.1% formic acid) 10 min. 5 min. hold, Rt=12.290, LRMS ESI m/z 609.20 (M+1).

Example 29: 8-(6-{[3-(2-Oxo-1-pyrrolidinyl)propyl] (3-fluorophenyl)carbonylamino}-3-pyridyl)-1,3-dicyclopropylxanthine In a 50 mL flask, Preparative Example G (0.150 g, 0.33 mmol) was combined with 3-Fluorobenzoyl Chloride (0.081 mL, 0.67 mmol) in dry pyridine (15 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-7% MeOH in DCM. Like fractions were collected and dried in vacuo. Yield: 0.105 g. HPLC-MS conditions: 40%-80% MeOH (0.1% formic acid)/$H_2O$ (0.1% formic acid) 10 min. 5 min. hold, Rt=12.622, LRMS ESI m/z 572.25 (M+1).

Example 30: 8-(6-{[3-(2-Oxo-1-pyrrolidinyl)propyl] (3-fluorophenyl)carbonylamino}-3-pyridyl)-1-(2-methoxyethyl)-3-propylxanthine In a 50 mL flask, Preparative Example B (0.150 g, 0.33 mmol) was combined with 3-Fluorobenzoyl Chloride (0.076 mL, 0.67 mmol) in dry pyridine (15 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-7% MeOH in DCM. Like fractions were collected and dried in vacuo. Yield: HPLC-MS conditions: 40%-80% MeOH (0.1% formic acid)/$H_2O$ (0.1% formic acid) 10 min. 5 min. hold, Rt=13.928, LRMS ESI m/z 592.25 (M+1).

Example 31: 8-{6-[N-(ethyl)[6-fluoro-3-pyridyl]carbonylamino]-3-pyridyl}-1-[3-(2-oxo-1-pyrrolidinyl)propyl]-3-propylxanthine In a 50 mL flask, Preparative Example J (0.240 g, 0.43 mmol) was combined with 6-Fluoronicotinoyl chloride (0.194 mL, 1.7 mmol) in dry pyridine (10 mL) and dry DCM (1.58 mL). The reaction stirred at 40° C. for 24 hours. The reaction was checked via HPLC for completion, and more acid chloride was added. The reaction stirred for 8 hours at 45° C. The reaction was checked via HPLC for completion, and more acid chloride was added. The reaction stirred for 72 hours at 45° C. The reaction was checked via HPLC for completion, and more acid chloride was added. The reaction stirred for 8 hours at 45° C. When the reaction was complete via HPLC, the solvent was removed in vacuo and the crude was adhered to silica for column chromatography. The column was eluted with 0-7% MeOH in DCM, and like fractions were collected and dried in vacuo. Yield: 0.240 g, 0.40 mmol, 79.23%. HPLC-MS conditions: 40%-80% MeOH (0.1% formic acid)/$H_2O$ (0.1% formic acid) 10 min. 5 min. hold, Rt=13.157, LRMS ESI m/z 563.30 (M+1).

Example 32: 8-{6-[N-(ethyl)[4-fluorophenyl]carbonylamino]-3-pyridyl}-1-[3-(2-Oxo-1-pyrrolidinyl)propyl]-3-propylxanthine In a 50 mL flask, Preparative Example J (0.240 g, 0.51 mmol) was combined with 4-Fluorobenzoyl chloride (0.243 mL, 2.04 mmol) in dry pyridine (10 mL) and dry DCM (1.58 mL). The reaction stirred at 40° C. for 24 hours. The reaction was checked via HPLC for completion, and more acid chloride was added. The reaction stirred for 24 hours at 45° C. The reaction was checked via HPLC for completion, and more acid chloride was added. The reaction stirred for 24 hours at 45° C. Water (~2 mL) was added to quench the reaction. The solvent was removed in vacuo, and the resulting crude material was adhered to silica with DCM/EtOH for column chromatography. The column was eluted with 0-7% MeOH in DCM. Like fractions were collected and dried in vacuo. Yield: 0.243 g, 0.41 mmol, 80.22% HPLC-MS conditions: 40%-80% MeOH (0.1% formic acid)/$H_2O$ (0.1% formic acid) 10 min. 5 min. hold, Rt=14.481, LRMS ESI m/z 562.30 (M+1).

Example 33: 8-(6-{[(1-Methyl-5-oxo-3-pyrrolidinyl)methyl](4-fluorophenyl)carbonylamino}-3-pyridyl)-1-(3-methoxypropyl)-3-propylxanthine In a 50 mL flask, Preparative Example K (0.150 g, 0.32 mmol) was combined with 4-Fluorobenzoyl chloride (0.151 mL, 1.28 mmol) in dry pyridine (10 mL) and dry DCM (1.585 mL). The reaction stirred at 40° C. for 24 hours. The reaction was checked via HPLC for completion, and more acid chloride was added. The reaction stirred for 24 hours at 45° C. The reaction was checked via HPLC for completion, and more acid chloride was added. The reaction stirred for 24 hours at 45° C. Water (~2 mL) was added to quench the reaction. The solvent was removed in vacuo, and the resulting crude material was adhered to silica with DCM/EtOH for column chromatography. The column was eluted with 0-7% MeOH in DCM. Like fractions were collected and dried in vacuo. Yield: 0.145 g, 0.24 mmol, 76.59%. HPLC-MS conditions: 40%-80% MeOH (0.1% formic acid)/$H_2O$ (0.1% formic acid) 10 min. 5 min. hold, Rt=13.918, LRMS ESI m/z 592.25 (M+1).

Example 34: 8-(6-{[(1-Methyl-5-oxo-3-pyrrolidinyl)methyl](4-fluorophenyl)carbonylamino}-3-pyridyl)-1-cyclopropyl-3-propylxanthine In a 50 mL flask, Preparative Example L (0.150 g, 0.34 mmol) was combined with 4-Fluorobenzoyl chloride (0.175 mL, 1.37 mmol) in dry pyridine (15 mL). The reaction stirred at 40° C. for 24 hours. Water (~2 mL) was added to quench the reaction. The water and pyridine were removed in vacuo, and the resulting oil was dissolved in DCM for purification by silica column chromatography. The column was eluted with 0-5% MeOH in DCM, and like fractions were collected and dried in vacuo. Yield: 0.1533 g, 0.27 mmol, 79.90% HPLC-MS conditions: 40%-80% MeOH (0.1% formic acid)/$H_2O$ (0.1% formic acid) 10 min. 5 min. hold, Rt=13.558, LRMS ESI m/z 560.30 (M+1).

Example 35: 8-(6-{[(1-Methyl-5-oxo-3-pyrrolidinyl)methyl](4-fluorophenyl)carbonylamino}-3-pyridyl)-1,3-dicyclopropylxanthine In a 50 mL flask, Preparative Example M (0.150 g, 0.43 mmol) was combined with 4-Fluorobenzoyl chloride (0.194 mL, 1.7 mmol) in dry pyridine (10 mL) and dry DCM (1.585 mL). The reaction stirred at 40° C. for 24 hours. The reaction was checked via HPLC for completion, and more acid chloride was added. The reaction stirred for 24 hours at 45° C. The reaction was checked via HPLC for completion, and more acid chloride was added. The reaction stirred for 24 hours at 45° C. Water (~2 mL) was added to quench the reaction. The solvent was removed in vacuo, and the resulting crude material was adhered to silica with DCM/EtOH for column chromatography. The column was eluted with 0-7% MeOH in DCM. Like fractions were collected and dried in vacuo. Yield: 0.095 g, 0.16 mmol, 46.54%. HPLC-MS conditions: 40%-80% MeOH (0.1% formic acid)/$H_2O$ (0.1% formic acid) 10 min. 5 min. hold, Rt=12.124, LRMS ESI m/z 558.25 (M+1).

Representative compounds described herein have been tested for their activity as $A_{2B}$ antagonists and shown to be active. Test compounds were tested for $A_{2B}$ antagonism according to: Cooper J, Hill S J, Alexander S P. An endogenous A2B adenosine receptor coupled to cyclic AMP generation in human embryonic kidney (HEK 293) cells. Br J Pharmacol. 1997 October; 122(3):546-50. doi: 10.1038/sj.bjp.0701401. PMID: 9351513; PMCID: PMC1564960.

TABLE 1

Percent Inhibition of NECA (5'-N-ethylcarboxamidoadenosine) of Representative Compounds At 100 nM or 111 nM

| Ex # | Structure | % Inhibition |
|---|---|---|
| 1 | 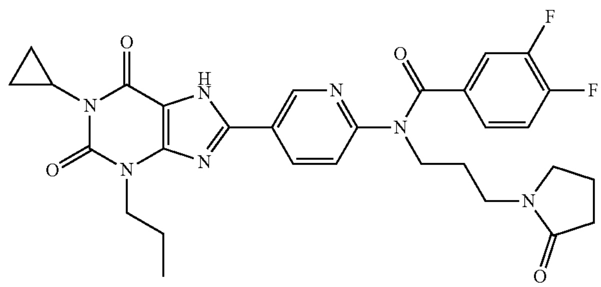 [SMILES: CCCn1c(=O)n(C2CC2)c(=O)c2[nH]c(-c3ccc(N(CCCN4CCCC4=O)C(=O)c4ccc(F)c(F)c4)nc3)nc21] | +++ |
| 2 | 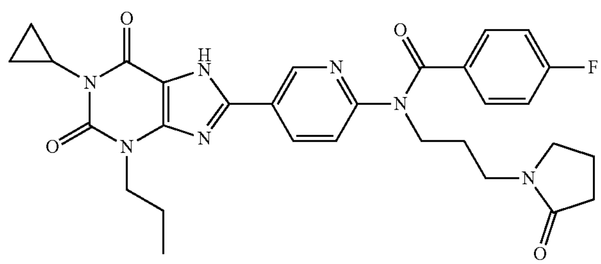 | Not Tested |
| 3 | 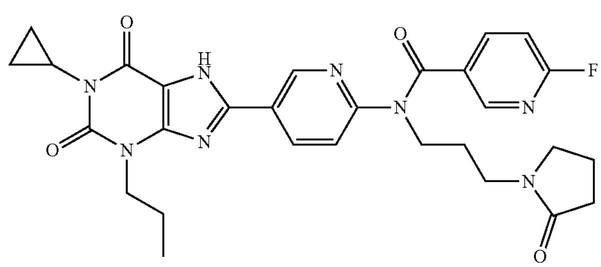 [SMILES: CCCn1c(=O)n(C2CC2)c(=O)c2[nH]c(-c3ccc(N(CCCN4CCCC4=O)C(=O)c4ccc(F)nc4)nc3)nc21] | ++ |
| 4 | 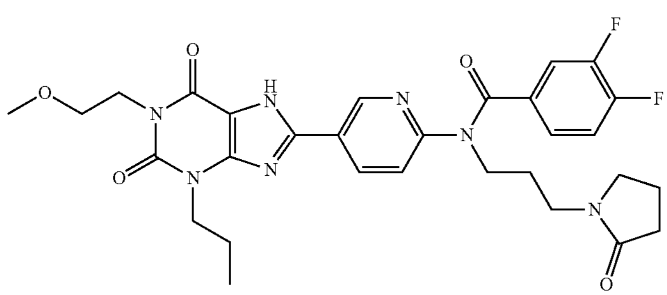 [SMILES: CCCn1c(=O)n(CCOC)c(=O)c2[nH]c(-c3ccc(N(CCCN4CCCC4=O)C(=O)c4ccc(F)c(F)c4)nc3)nc21] | +++ |
| 5 | 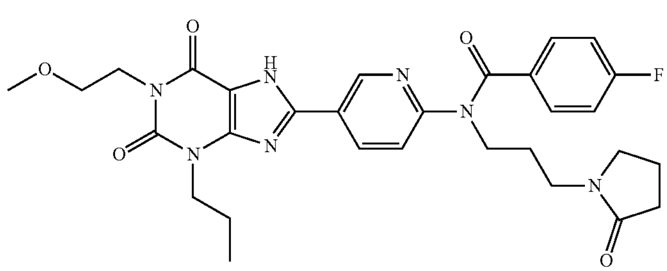 | +++ |

TABLE 1-continued

Percent Inhibition of NECA (5'-N-ethylcarboxamidoadenosine) of Representative Compounds At 100 nM or 111 nM

| Ex # | Structure | % Inhibition |
|---|---|---|
| 6 | 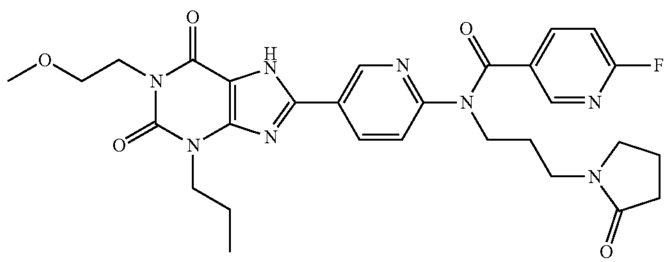 | +++ |
| 7 | 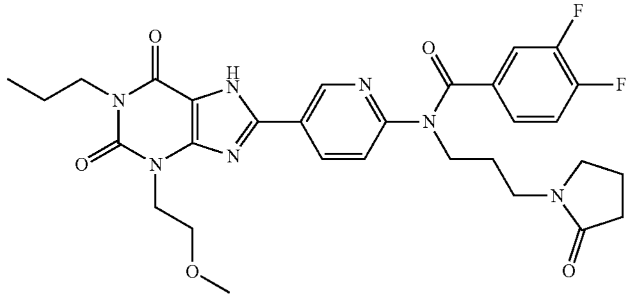 [SMILES: CCCn1c(=O)c2[nH]c(-c3ccc(N(CCCN4CCCC4=O)C(=O)c4ccc(F)c(F)c4)nc3)nc2n(CCOC)c1=O] | + |
| 8 | 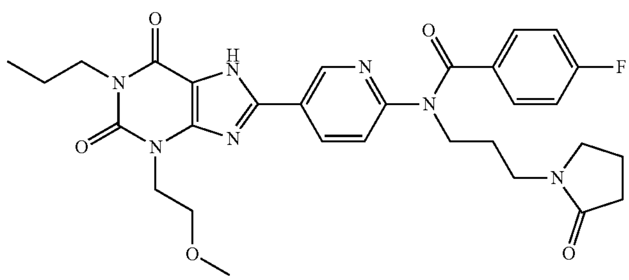 [SMILES: CCCn1c(=O)c2[nH]c(-c3ccc(N(CCCN4CCCC4=O)C(=O)c4ccc(F)cc4)nc3)nc2n(CCOC)c1=O] | ++ |
| 9 | 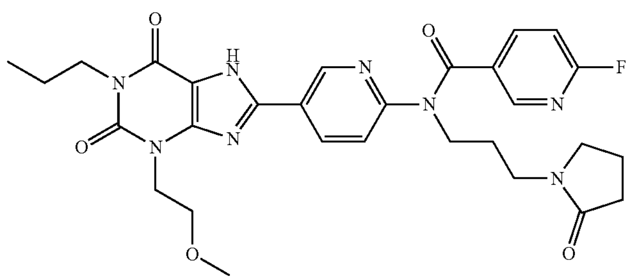 | + |
| 10 | 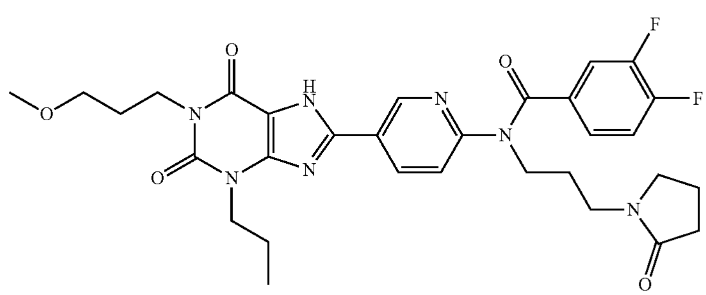 [SMILES: CCCn1c(=O)n(CCCOC)c(=O)c2[nH]c(-c3ccc(N(CCCN4CCCC4=O)C(=O)c4ccc(F)c(F)c4)nc3)nc21] | +++ |

TABLE 1-continued

Percent Inhibition of NECA (5'-N-ethylcarboxamidoadenosine) of Representative Compounds At 100 nM or 111 nM

| Ex # | Structure | % Inhibition |
|------|-----------|--------------|
| 11 | 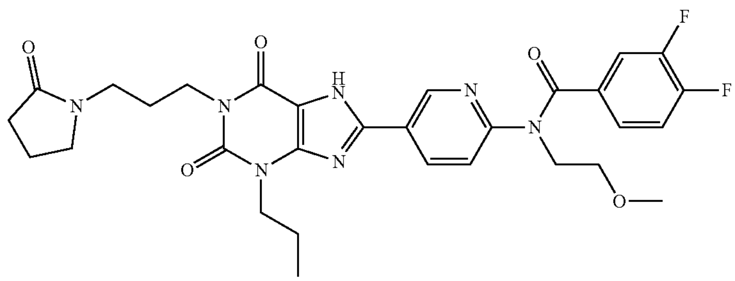 [SMILES: CCCn1c(=O)n(CCCN2CCCC2=O)c(=O)c2[nH]c(-c3ccc(N(CCOC)C(=O)c4ccc(F)c(F)c4)nc3)nc21] | ++ |
| 12 | 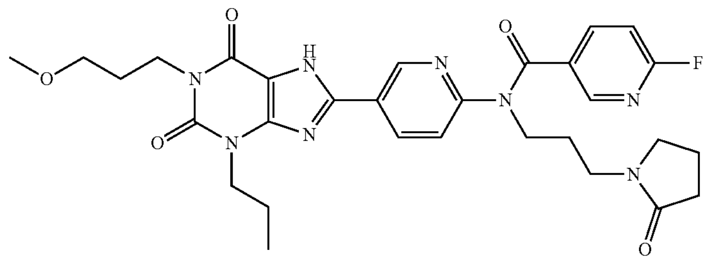 | +++ |
| 13 | 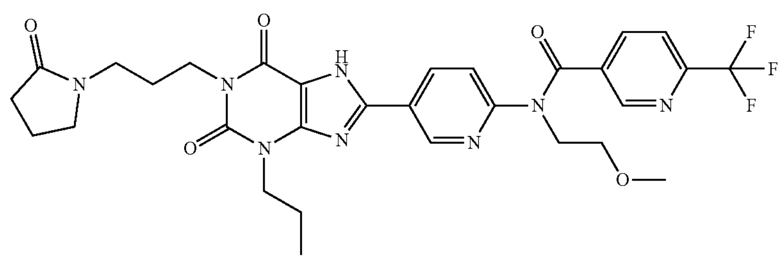 [SMILES: CCCn1c(=O)n(CCCN2CCCC2=O)c(=O)c2[nH]c(-c3ccc(N(CCOC)C(=O)c4ccc(C(F)(F)F)nc4)nc3)nc21] | ++ |
| 14 | 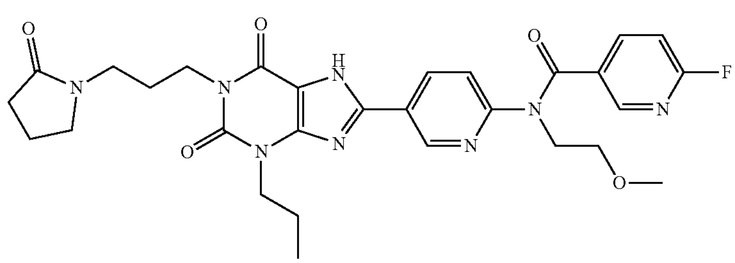 [SMILES: CCCn1c(=O)n(CCCN2CCCC2=O)c(=O)c2[nH]c(-c3ccc(N(CCOC)C(=O)c4ccc(F)nc4)nc3)nc21] | + |
| 15 | 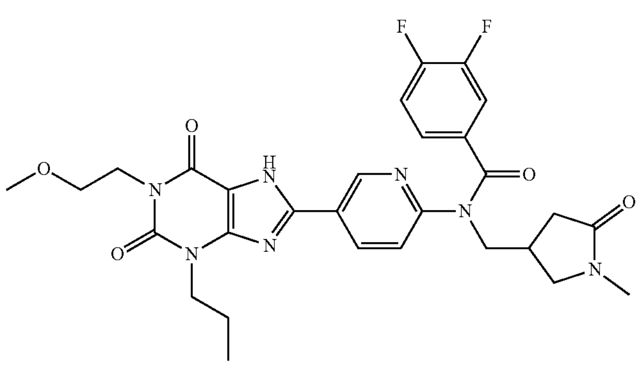 [SMILES: CCCn1c(=O)n(CCOC)c(=O)c2[nH]c(-c3ccc(N(CC4CC(=O)N(C)C4)C(=O)c4ccc(F)c(F)c4)nc3)nc21] | ++ |

TABLE 1-continued
Percent Inhibition of NECA (5'-N-ethylcarboxamidoadenosine) of Representative Compounds At 100 nM or 111 nM
| Ex # | Structure | % Inhibition |
|---|---|---|
| 16 | 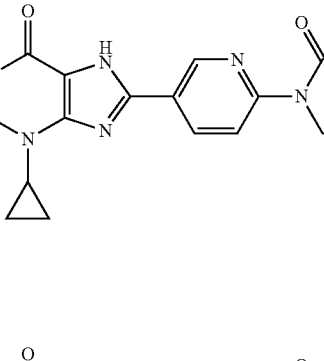 | ++ |
| 17 | 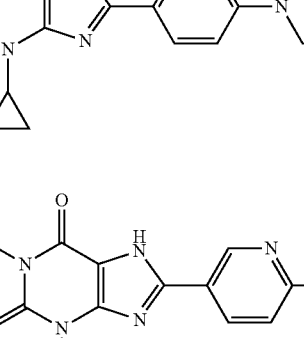 | + |
| 18 | 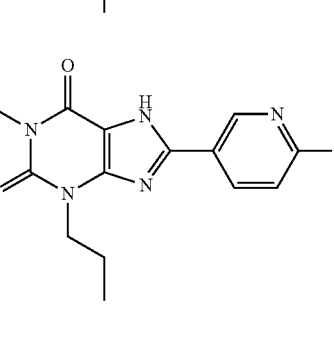 | + |
| 19 | 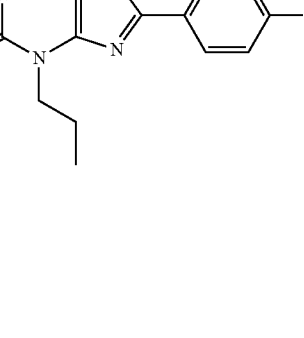 | + |
| 20 | 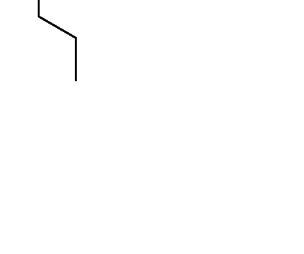 | ++ |

TABLE 1-continued

Percent Inhibition of NECA (5'-N-ethylcarboxamidoadenosine) of Representative Compounds At 100 nM or 111 nM

| Ex # | Structure | % Inhibition |
|---|---|---|
| 21 | 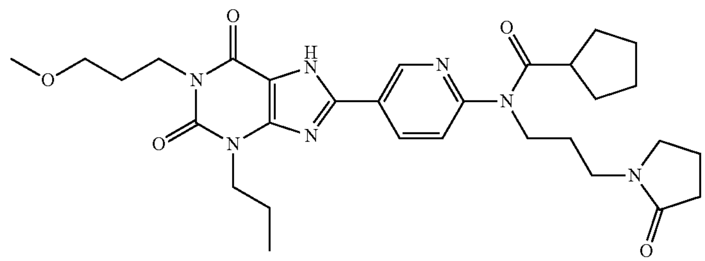 [SMILES: CCCn1c(=O)n(CCCOC)c(=O)c2[nH]c(-c3ccc(N(CCCN4CCCC4=O)C(=O)C4CCCC4)nc3)nc21] | + |
| 22 | 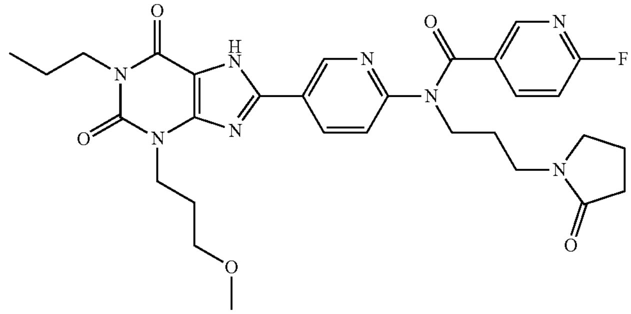 [SMILES: CCCn1c(=O)c2[nH]c(-c3ccc(N(CCCN4CCCC4=O)C(=O)c4ccc(F)nc4)nc3)nc2n(CCCOC)c1=O] | + |
| 23 | 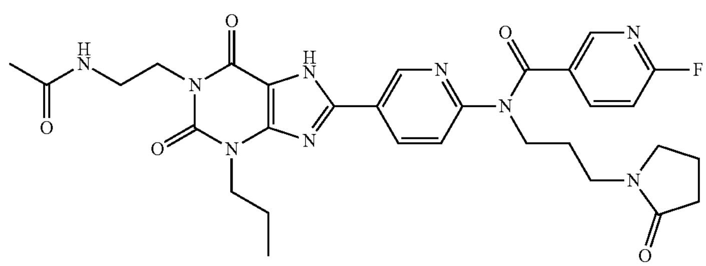 [SMILES: CCCn1c(=O)n(CCNC(C)=O)c(=O)c2[nH]c(-c3ccc(N(CCCN4CCCC4=O)C(=O)c4ccc(F)nc4)nc3)nc21] | + |
| 24 | 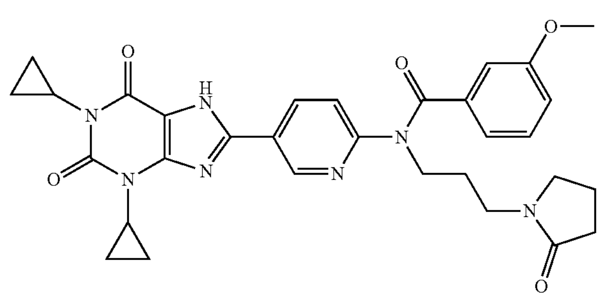 [SMILES: COc1cccc(C(=O)N(CCCN2CCCC2=O)c2ccc(-c3nc4c([nH]3)c(=O)n(C3CC3)c(=O)n4C3CC3)cn2)c1] | +++ |
| 25 | 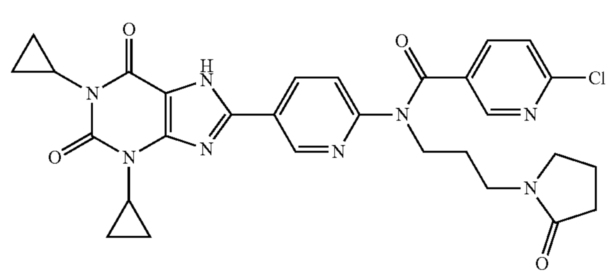 [SMILES: O=C1CCCN1CCCN(C(=O)c1ccc(Cl)nc1)c1ccc(-c2nc3c([nH]2)c(=O)n(C2CC2)c(=O)n3C2CC2)cn1] | +++ |

TABLE 1-continued

Percent Inhibition of NECA (5'-N-ethylcarboxamidoadenosine) of Representative Compounds At 100 nM or 111 nM

| Ex # | Structure | % Inhibition |
|---|---|---|
| 26 | 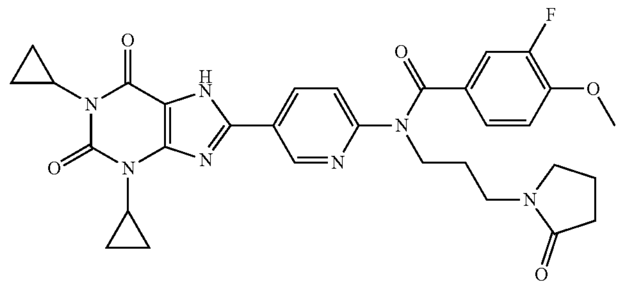 [SMILES: COc1ccc(C(=O)N(CCCN2CCCC2=O)c2ccc(-c3nc4c([nH]3)c(=O)n(C3CC3)c(=O)n4C3CC3)cn2)cc1F] | +++ |
| 27 | 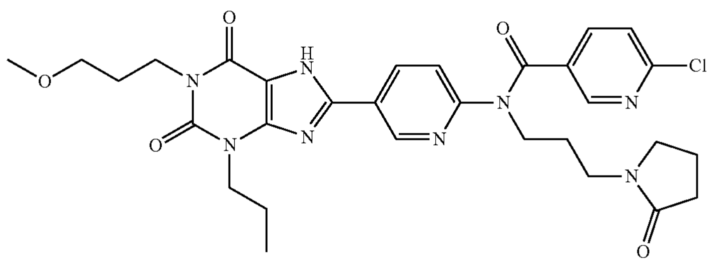 [SMILES: CCCn1c(=O)n(CCCOC)c(=O)c2[nH]c(-c3ccc(N(CCCN4CCCC4=O)C(=O)c4ccc(Cl)nc4)nc3)nc21] | +++ |
| 28 | 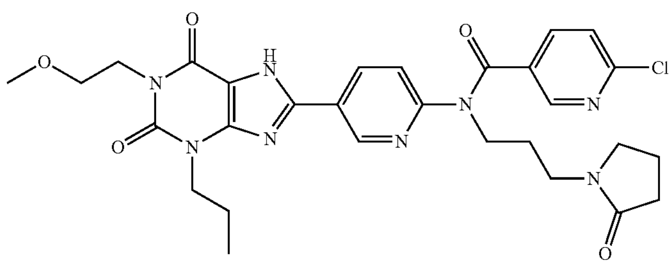 [SMILES: CCCn1c(=O)n(CCOC)c(=O)c2[nH]c(-c3ccc(N(CCCN4CCCC4=O)C(=O)c4ccc(Cl)nc4)nc3)nc21] | +++ |
| 29 | 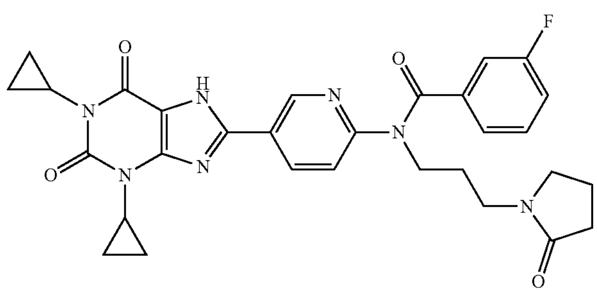 [SMILES: O=C1CCCN1CCCN(C(=O)c1cccc(F)c1)c1ccc(-c2nc3c([nH]2)c(=O)n(C2CC2)c(=O)n3C2CC2)cn1] | + |
| 30 | 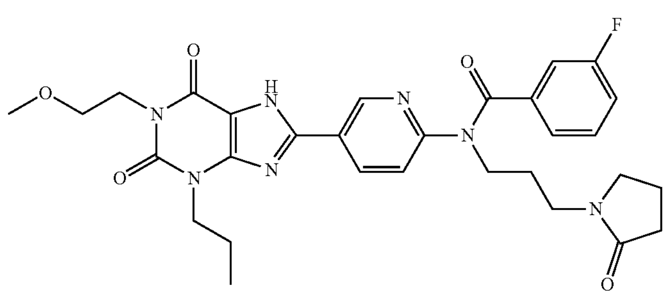 [SMILES: CCCn1c(=O)n(CCOC)c(=O)c2[nH]c(-c3ccc(N(CCCN4CCCC4=O)C(=O)c4cccc(F)c4)nc3)nc21] | +++ |

TABLE 1-continued

Percent Inhibition of NECA (5'-N-ethylcarboxamidoadenosine) of Representative Compounds At 100 nM or 111 nM

| Ex # | Structure | % Inhibition |
|---|---|---|
| 31 | 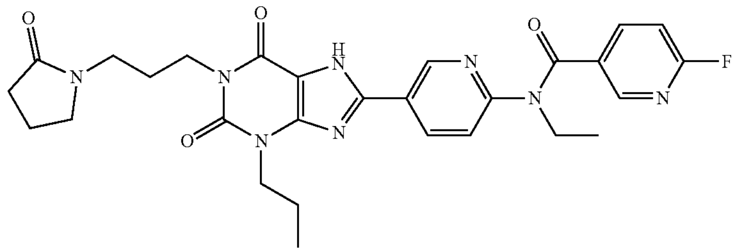 | + |
| 32 | 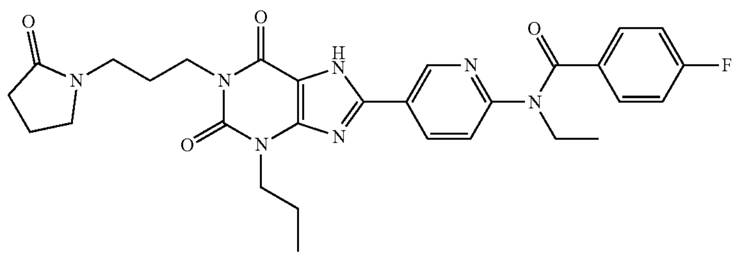 | + |
| 33 | 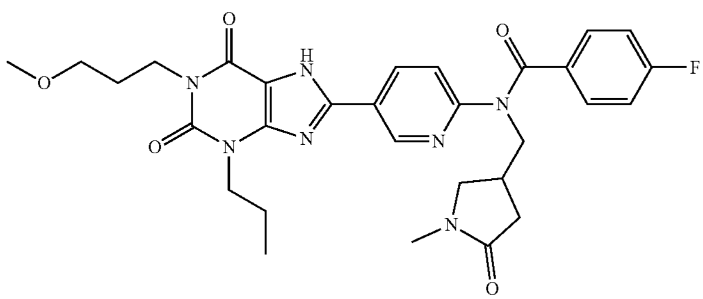 [SMILES: CCCn1c(=O)n(CCCOC)c(=O)c2[nH]c(-c3ccc(N(CC4CC(=O)N(C)C4)C(=O)c4ccc(F)cc4)nc3)nc21] | + |
| 34 | 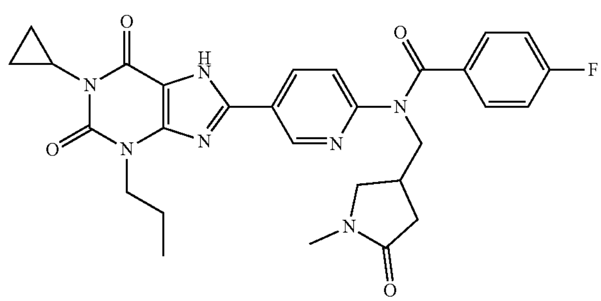 [SMILES: CCCn1c(=O)n(C2CC2)c(=O)c2[nH]c(-c3ccc(N(CC4CC(=O)N(C)C4)C(=O)c4ccc(F)cc4)nc3)nc21] | + |
| 35 | 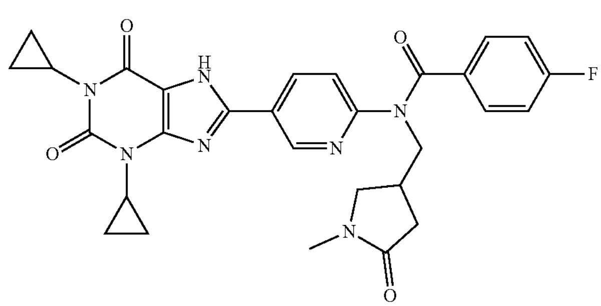 | + |

67% to 100% = +++
33% to 67% = ++
1% to 33% = +

Additional compounds described herein are shown in Table 2 below. These compounds can be prepared like Compounds 1-35 described above.

TABLE 2

| Ex. # | Structure |
| --- | --- |
| 1 | 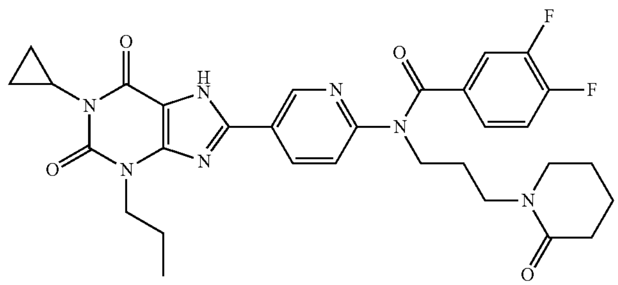 [SMILES: CCCn1c(=O)n(C2CC2)c(=O)c2[nH]c(-c3ccc(N(CCCN4CCCCC4=O)C(=O)c4ccc(F)c(F)c4)nc3)nc21] |
| 2 | 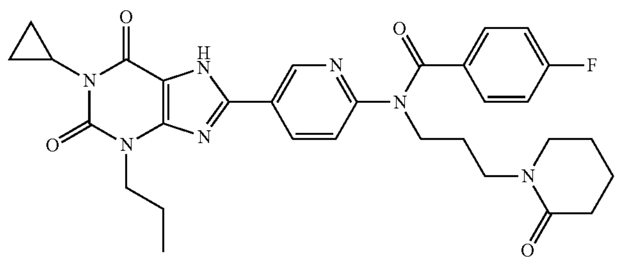 [SMILES: CCCn1c(=O)n(C2CC2)c(=O)c2[nH]c(-c3ccc(N(CCCN4CCCCC4=O)C(=O)c4ccc(F)cc4)nc3)nc21] |
| 3 | 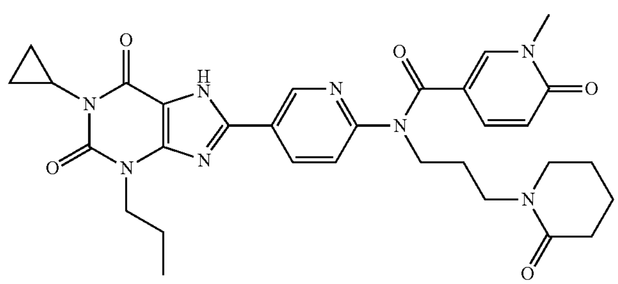 [SMILES: CCCn1c(=O)n(C2CC2)c(=O)c2[nH]c(-c3ccc(N(CCCN4CCCCC4=O)C(=O)c4ccc(=O)n(C)c4)nc3)nc21] |
| 4 | 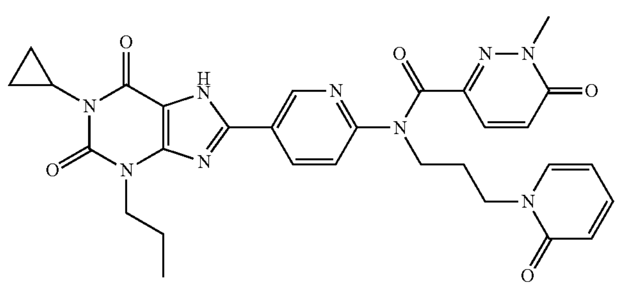 [SMILES: CCCn1c(=O)n(C2CC2)c(=O)c2[nH]c(-c3ccc(N(CCCn4ccccc4=O)C(=O)c4ccc(=O)n(C)n4)nc3)nc21] |
| 5 | 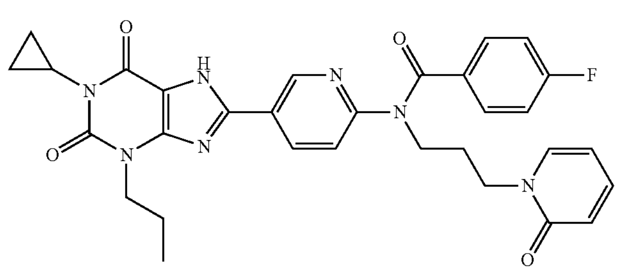 |

TABLE 2-continued

| Ex. # | Structure |
|---|---|
| 6 | 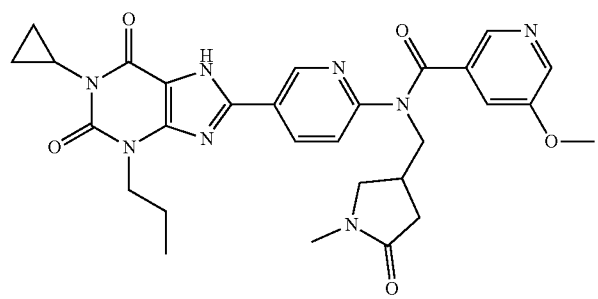 [SMILES: CCCn1c(=O)n(C2CC2)c(=O)c2[nH]c(-c3ccc(N(CC4CC(=O)N(C)C4)C(=O)c4cncc(OC)c4)nc3)nc21] |
| 7 | 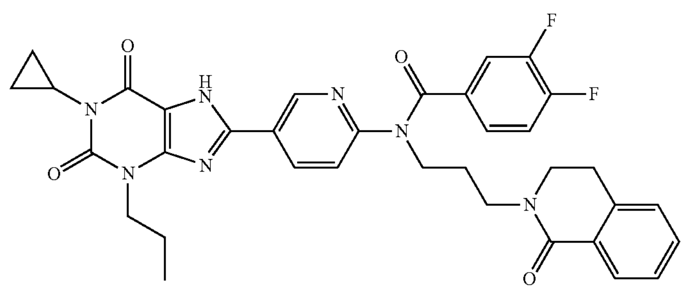 [SMILES: CCCn1c(=O)n(C2CC2)c(=O)c2[nH]c(-c3ccc(N(CCCN4CCc5ccccc5C4=O)C(=O)c4ccc(F)c(F)c4)nc3)nc21] |
| 8 | 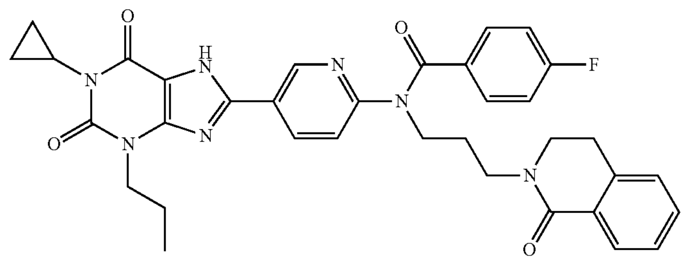 [SMILES: CCCn1c(=O)n(C2CC2)c(=O)c2[nH]c(-c3ccc(N(CCCN4CCc5ccccc5C4=O)C(=O)c4ccc(F)cc4)nc3)nc21] |
| 9 | 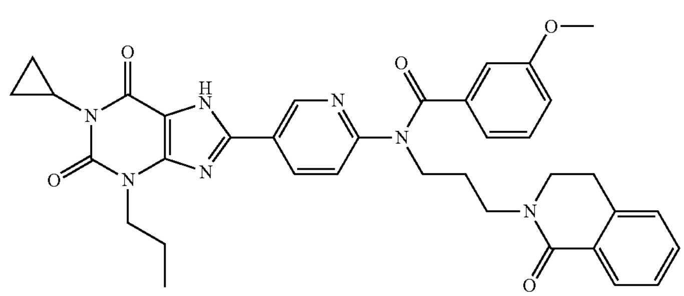 [SMILES: CCCn1c(=O)n(C2CC2)c(=O)c2[nH]c(-c3ccc(N(CCCN4CCc5ccccc5C4=O)C(=O)c4cccc(OC)c4)nc3)nc21] |
| 10 | 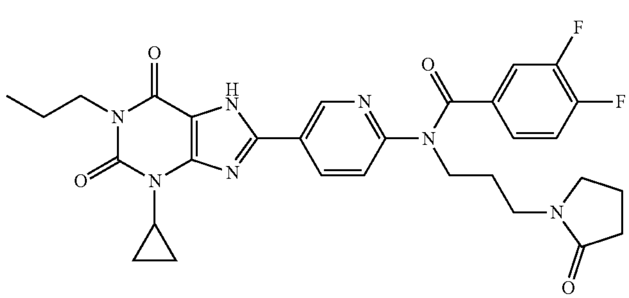 [SMILES: CCCn1c(=O)c2[nH]c(-c3ccc(N(CCCN4CCCC4=O)C(=O)c4ccc(F)c(F)c4)nc3)nc2n(C2CC2)c1=O] |

TABLE 2-continued

| Ex. # | Structure |
|---|---|
| 11 | 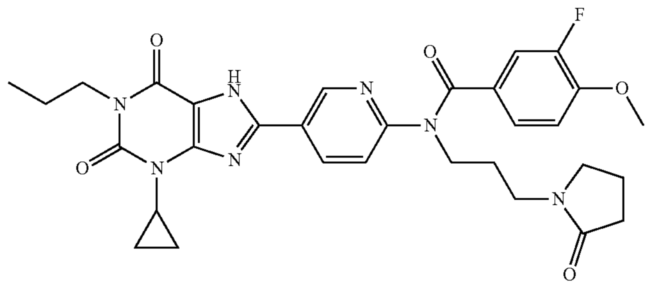 [SMILES: CCCn1c(=O)c2[nH]c(-c3ccc(N(CCCN4CCCC4=O)C(=O)c4ccc(OC)c(F)c4)nc3)nc2n(C2CC2)c1=O] |
| 12 | 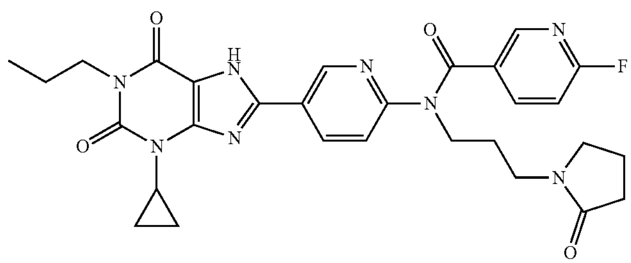 [SMILES: CCCn1c(=O)c2[nH]c(-c3ccc(N(CCCN4CCCC4=O)C(=O)c4ccc(F)nc4)nc3)nc2n(C2CC2)c1=O] |
| 13 | 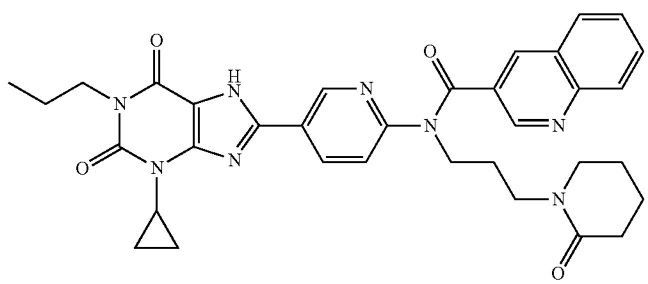 [SMILES: CCCn1c(=O)c2[nH]c(-c3ccc(N(CCCN4CCCCC4=O)C(=O)c4cnc5ccccc5c4)nc3)nc2n(C2CC2)c1=O] |
| 14 | 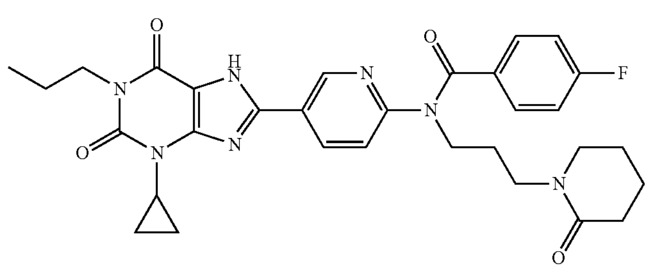 [SMILES: CCCn1c(=O)c2[nH]c(-c3ccc(N(CCCN4CCCCC4=O)C(=O)c4ccc(F)cc4)nc3)nc2n(C2CC2)c1=O] |
| 15 | 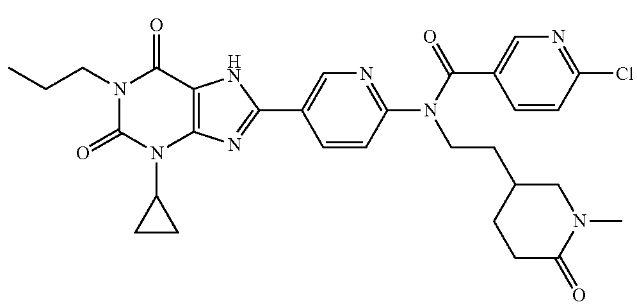 [SMILES: CCCn1c(=O)c2[nH]c(-c3ccc(N(CCC4CCC(=O)N(C)C4)C(=O)c4ccc(Cl)nc4)nc3)nc2n(C2CC2)c1=O] |

TABLE 2-continued

| Ex. # | Structure |
|---|---|
| 16 | 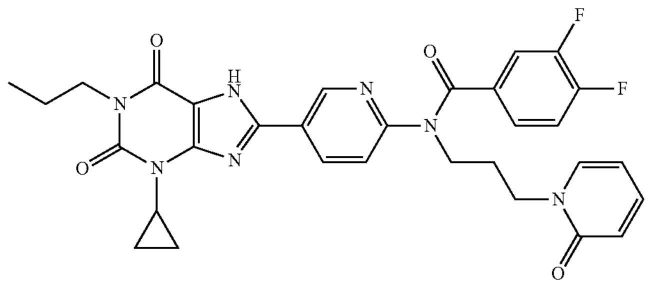 [SMILES: CCCn1c(=O)c2[nH]c(-c3ccc(N(CCCn4ccccc4=O)C(=O)c4ccc(F)c(F)c4)nc3)nc2n(C2CC2)c1=O] |
| 17 | 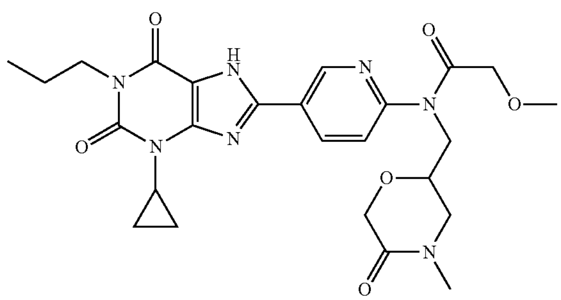 [SMILES: CCCn1c(=O)c2[nH]c(-c3ccc(N(CC4CN(C)C(=O)CO4)C(=O)COC)nc3)nc2n(C2CC2)c1=O] |
| 18 | 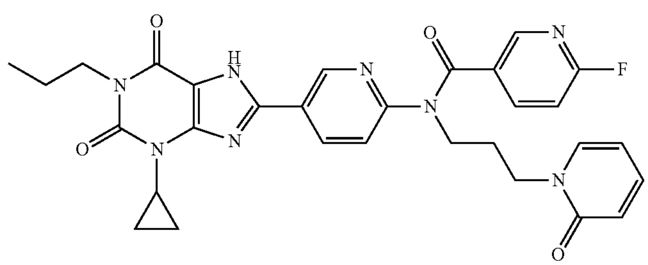 [SMILES: CCCn1c(=O)c2[nH]c(-c3ccc(N(CCCn4ccccc4=O)C(=O)c4ccc(F)nc4)nc3)nc2n(C2CC2)c1=O] |
| 19 | 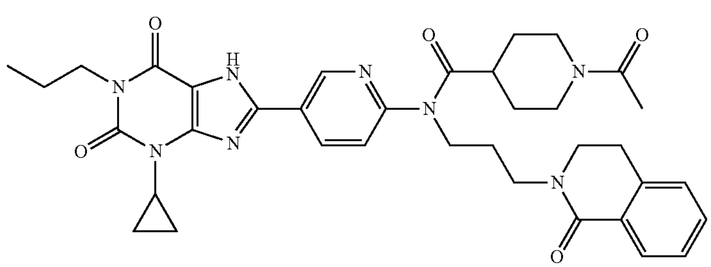 [SMILES: CCCn1c(=O)c2[nH]c(-c3ccc(N(CCCN4CCc5ccccc5C4=O)C(=O)C4CCN(C(C)=O)CC4)nc3)nc2n(C2CC2)c1=O] |
| 20 | 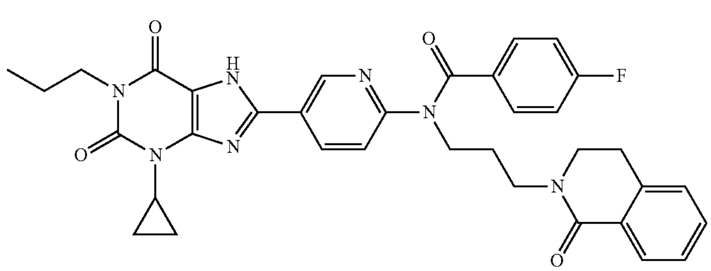 [SMILES: CCCn1c(=O)c2[nH]c(-c3ccc(N(CCCN4CCc5ccccc5C4=O)C(=O)c4ccc(F)cc4)nc3)nc2n(C2CC2)c1=O] |

TABLE 2-continued

| Ex. # | Structure |
| --- | --- |
| 21 | 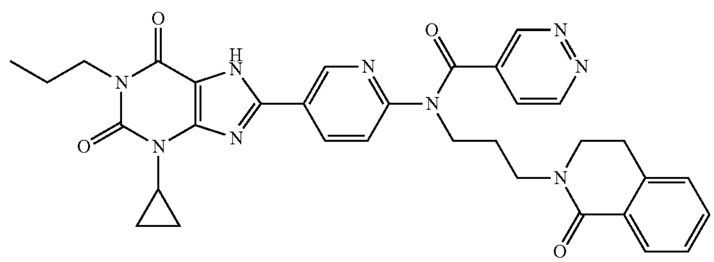 [SMILES: CCCn1c(=O)c2[nH]c(-c3ccc(N(CCCN4CCc5ccccc5C4=O)C(=O)c4ccnnc4)nc3)nc2n(C2CC2)c1=O] |
| 22 | 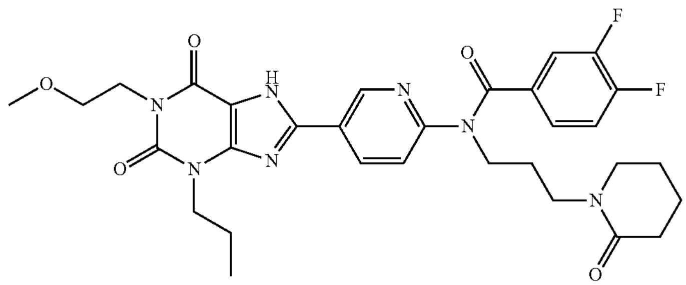 [SMILES: CCCn1c(=O)n(CCOC)c(=O)c2[nH]c(-c3ccc(N(CCCN4CCCCC4=O)C(=O)c4ccc(F)c(F)c4)nc3)nc21] |
| 23 | 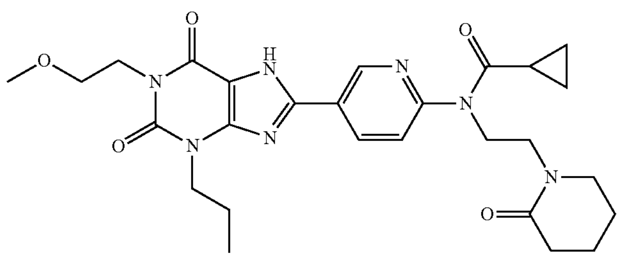 [SMILES: CCCn1c(=O)n(CCOC)c(=O)c2[nH]c(-c3ccc(N(CCN4CCCCC4=O)C(=O)C4CC4)nc3)nc21] |
| 24 | 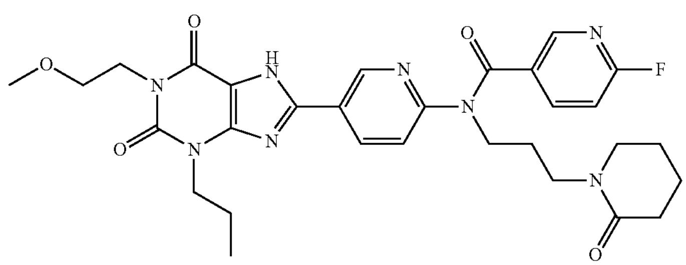 [SMILES: CCCn1c(=O)n(CCOC)c(=O)c2[nH]c(-c3ccc(N(CCCN4CCCCC4=O)C(=O)c4ccc(F)nc4)nc3)nc21] |
| 25 | 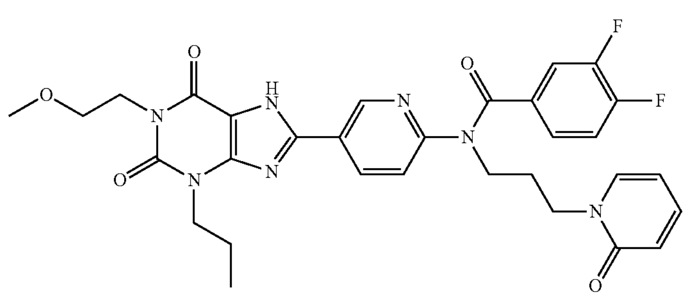 [SMILES: CCCn1c(=O)n(CCOC)c(=O)c2[nH]c(-c3ccc(N(CCCn4ccccc4=O)C(=O)c4ccc(F)c(F)c4)nc3)nc21] |

TABLE 2-continued

| Ex. # | Structure |
|---|---|
| 26 | 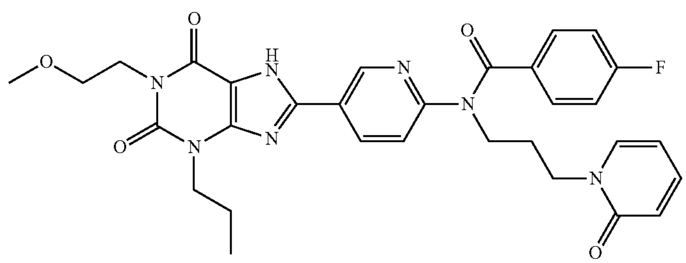 [SMILES: CCCn1c(=O)n(CCOC)c(=O)c2[nH]c(-c3ccc(N(CCCn4ccccc4=O)C(=O)c4ccc(F)cc4)nc3)nc21] |
| 27 | 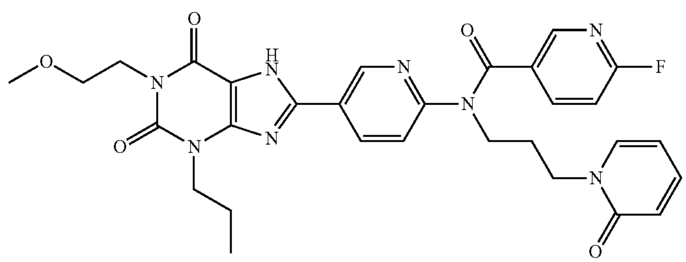 [SMILES: CCCn1c(=O)n(CCOC)c(=O)c2[nH]c(-c3ccc(N(CCCn4ccccc4=O)C(=O)c4ccc(F)nc4)nc3)nc21] |
| 28 | 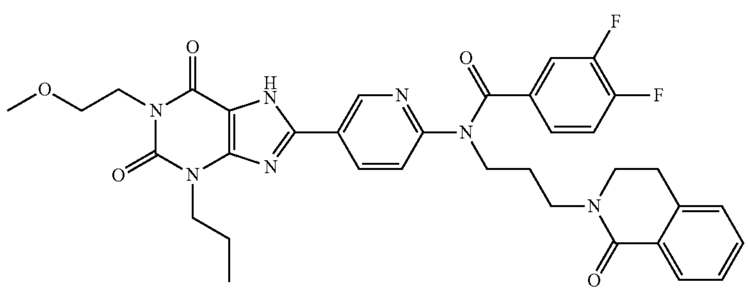 [SMILES: CCCn1c(=O)n(CCOC)c(=O)c2[nH]c(-c3ccc(N(CCCN4CCc5ccccc5C4=O)C(=O)c4ccc(F)c(F)c4)nc3)nc21] |
| 29 | 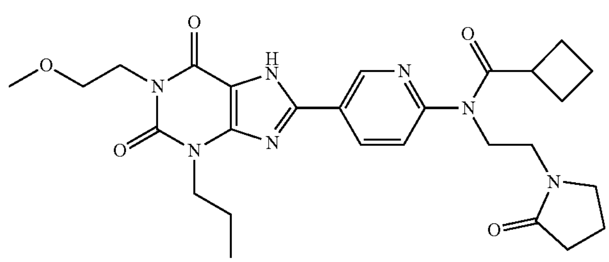 [SMILES: CCCn1c(=O)n(CCOC)c(=O)c2[nH]c(-c3ccc(N(CCN4CCCC4=O)C(=O)C4CCC4)nc3)nc21] |
| 30 | 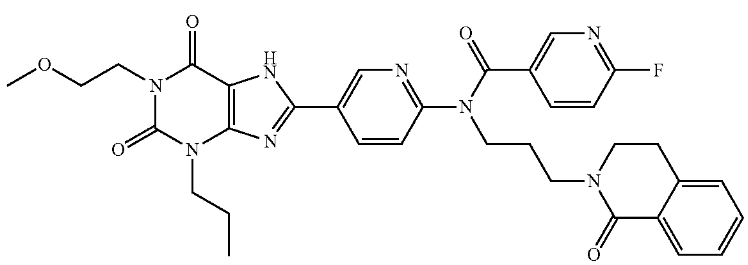 [SMILES: CCCn1c(=O)n(CCOC)c(=O)c2[nH]c(-c3ccc(N(CCCN4CCc5ccccc5C4=O)C(=O)c4ccc(F)nc4)nc3)nc21] |

TABLE 2-continued
| Ex. # | Structure |
|---|---|
| 31 | 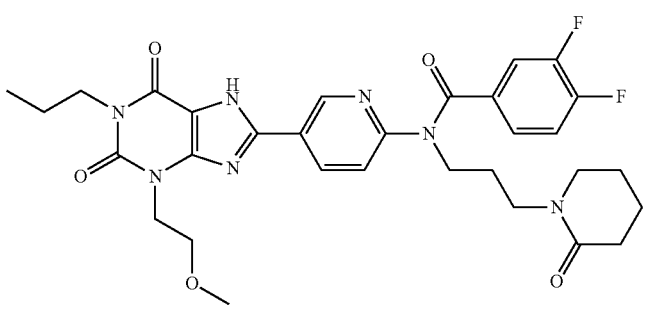 |
| 32 | 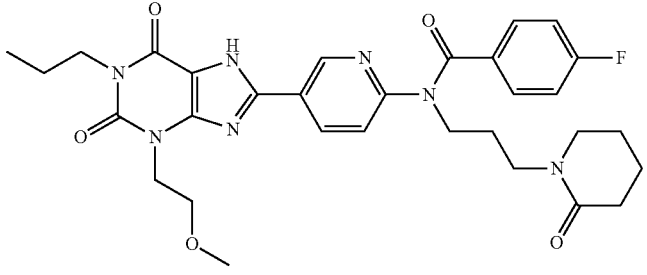 [SMILES: CCCn1c(=O)c2[nH]c(-c3ccc(N(CCCN4CCCCC4=O)C(=O)c4ccc(F)cc4)nc3)nc2n(CCOC)c1=O] |
| 33 | 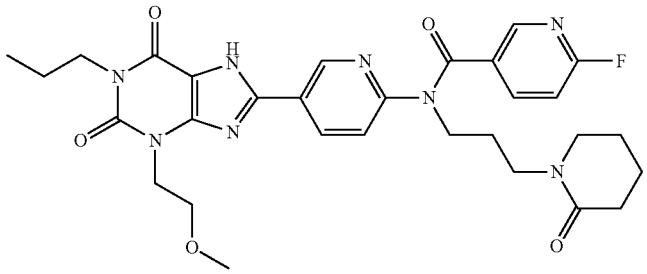 [SMILES: CCCn1c(=O)c2[nH]c(-c3ccc(N(CCCN4CCCCC4=O)C(=O)c4ccc(F)nc4)nc3)nc2n(CCOC)c1=O] |
| 34 | 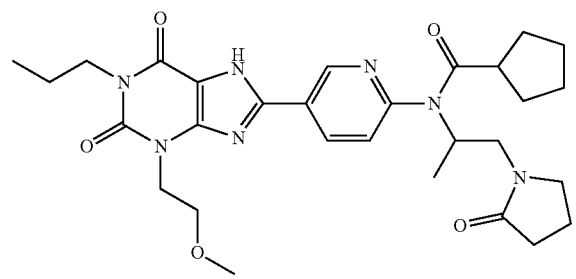 [SMILES: CCCn1c(=O)c2[nH]c(-c3ccc(N(C(=O)C4CCCC4)C(C)CN4CCCC4=O)nc3)nc2n(CCOC)c1=O] |
| 35 | 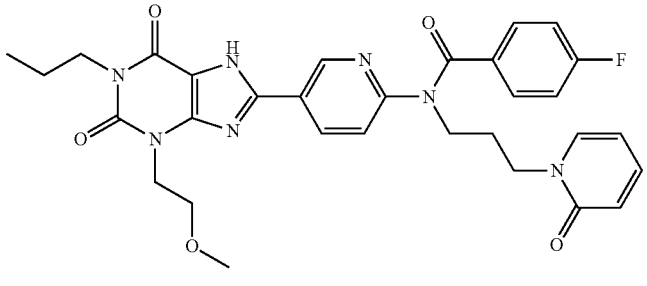 [SMILES: CCCn1c(=O)c2[nH]c(-c3ccc(N(CCCn4ccccc4=O)C(=O)c4ccc(F)cc4)nc3)nc2n(CCOC)c1=O] |

TABLE 2-continued

| Ex. # | Structure |
| --- | --- |
| 36 | 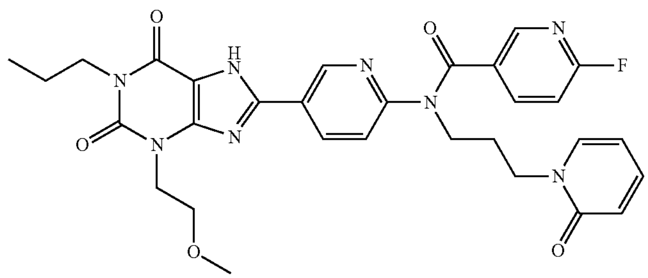 [SMILES: CCCn1c(=O)c2[nH]c(-c3ccc(N(CCCn4ccccc4=O)C(=O)c4ccc(F)nc4)nc3)nc2n(CCOC)c1=O] |
| 37 | 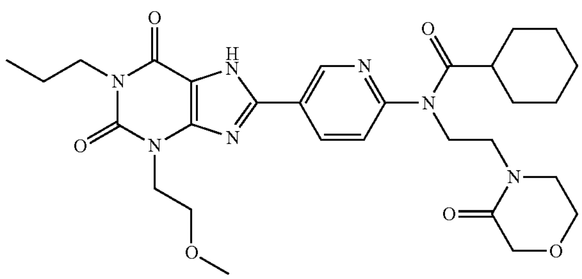 [SMILES: CCCn1c(=O)c2[nH]c(-c3ccc(N(CCN4CCOCC4=O)C(=O)C4CCCCC4)nc3)nc2n(CCOC)c1=O] |
| 38 | 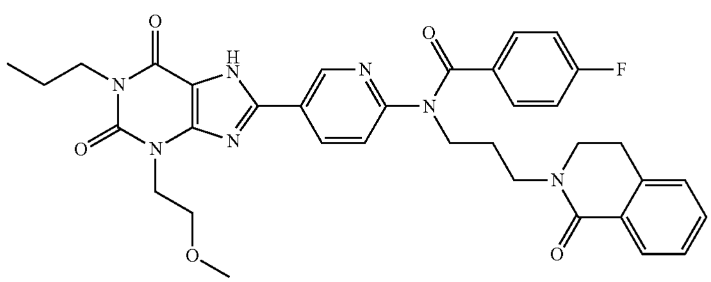 [SMILES: CCCn1c(=O)c2[nH]c(-c3ccc(N(CCCN4CCc5ccccc5C4=O)C(=O)c4ccc(F)cc4)nc3)nc2n(CCOC)c1=O] |
| 39 | 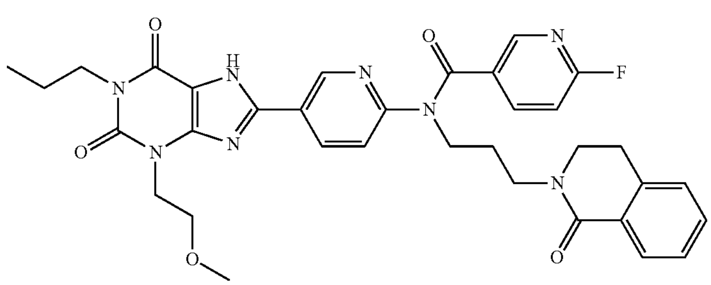 [SMILES: CCCn1c(=O)c2[nH]c(-c3ccc(N(CCCN4CCc5ccccc5C4=O)C(=O)c4ccc(F)nc4)nc3)nc2n(CCOC)c1=O] |
| 40 | 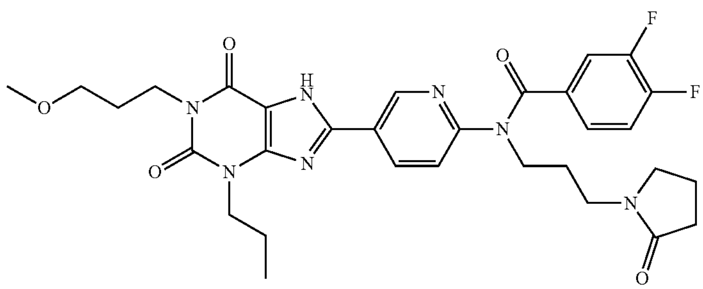 [SMILES: CCCn1c(=O)n(CCCOC)c(=O)c2[nH]c(-c3ccc(N(CCCN4CCCC4=O)C(=O)c4ccc(F)c(F)c4)nc3)nc21] |

TABLE 2-continued
| Ex. # | Structure |
|---|---|
| 41 | 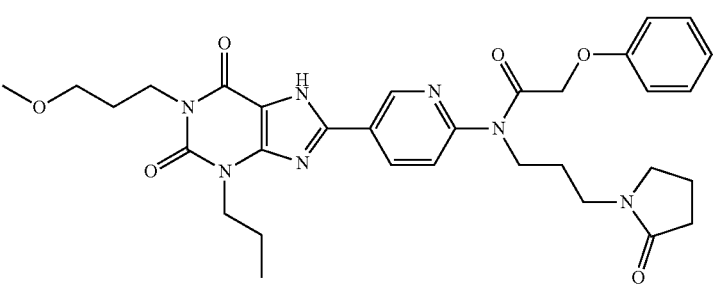 [SMILES: CCCn1c(=O)n(CCCOC)c(=O)c2[nH]c(-c3ccc(N(CCCN4CCCC4=O)C(=O)COc4ccccc4)nc3)nc21] |
| 42 | 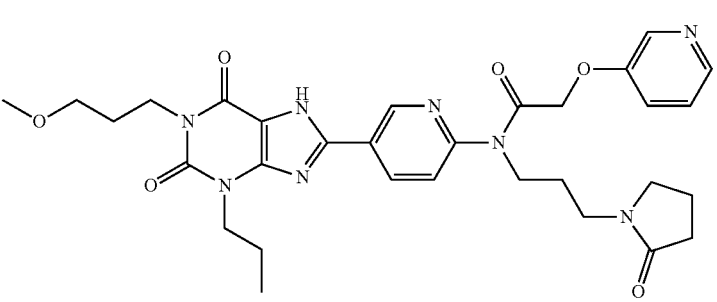 [SMILES: CCCn1c(=O)n(CCCOC)c(=O)c2[nH]c(-c3ccc(N(CCCN4CCCC4=O)C(=O)COc4cccnc4)nc3)nc21] |
| 43 | 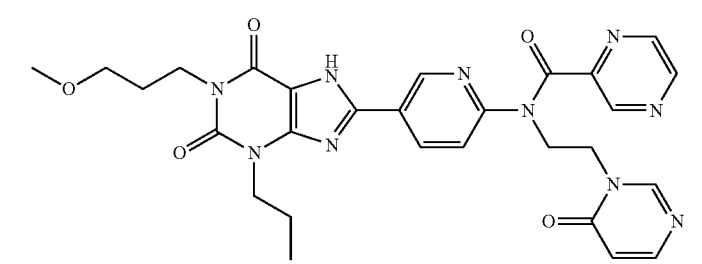 [SMILES: CCCn1c(=O)n(CCCOC)c(=O)c2[nH]c(-c3ccc(N(CCn4cnccc4=O)C(=O)c4cnccn4)nc3)nc21] |
| 44 | 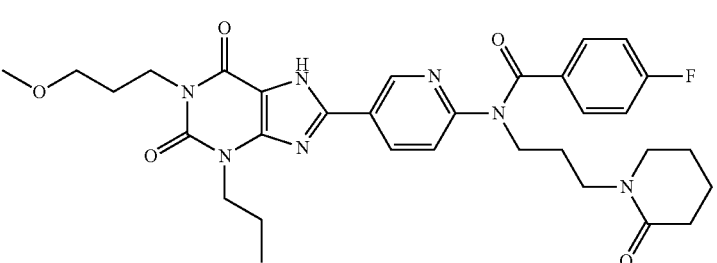 |
| 45 | 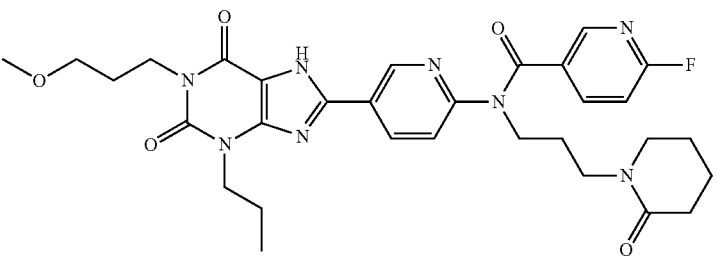 [SMILES: CCCn1c(=O)n(CCCOC)c(=O)c2[nH]c(-c3ccc(N(CCCN4CCCCC4=O)C(=O)c4ccc(F)nc4)nc3)nc21] |

TABLE 2-continued

| Ex. # | Structure |
|---|---|
| 46 | 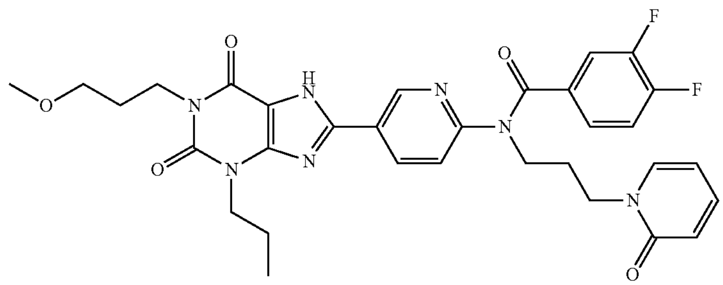 [SMILES: CCCn1c(=O)n(CCCOC)c(=O)c2[nH]c(-c3ccc(N(CCCn4ccccc4=O)C(=O)c4ccc(F)c(F)c4)nc3)nc21] |
| 47 | 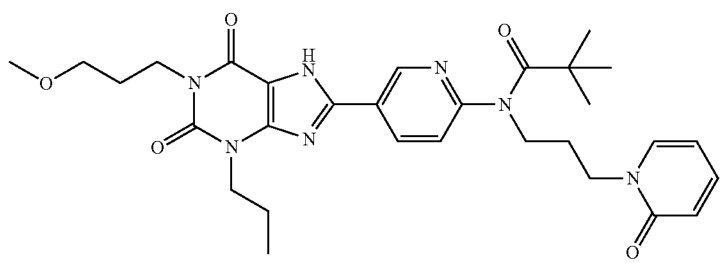 [SMILES: CCCn1c(=O)n(CCCOC)c(=O)c2[nH]c(-c3ccc(N(CCCn4ccccc4=O)C(=O)C(C)(C)C)nc3)nc21] |
| 48 | 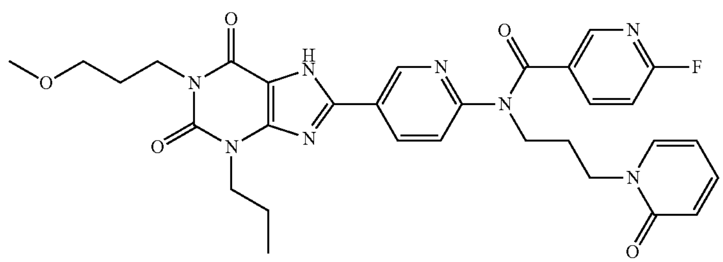 [SMILES: CCCn1c(=O)n(CCCOC)c(=O)c2[nH]c(-c3ccc(N(CCCn4ccccc4=O)C(=O)c4ccc(F)nc4)nc3)nc21] |
| 49 | 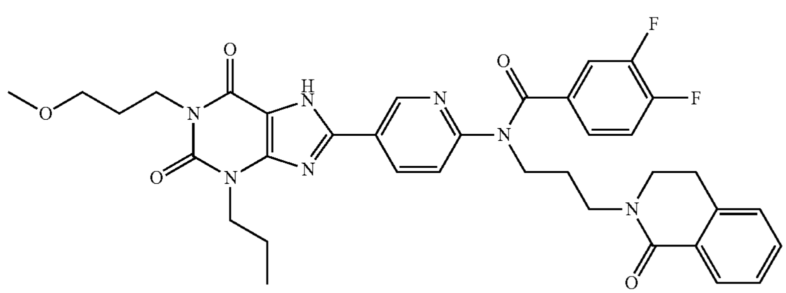 [SMILES: CCCn1c(=O)n(CCCOC)c(=O)c2[nH]c(-c3ccc(N(CCCN4CCc5ccccc5C4=O)C(=O)c4ccc(F)c(F)c4)nc3)nc21] |
| 50 | 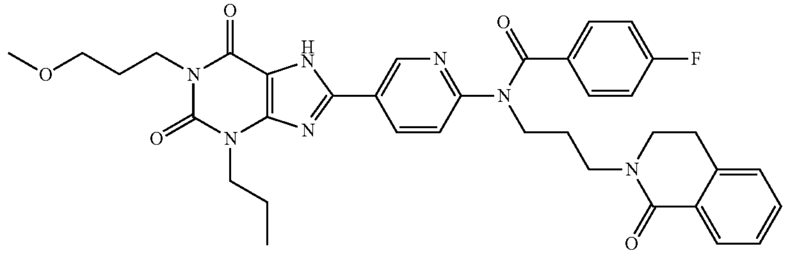 [SMILES: CCCn1c(=O)n(CCCOC)c(=O)c2[nH]c(-c3ccc(N(CCCN4CCc5ccccc5C4=O)C(=O)c4ccc(F)cc4)nc3)nc21] |

TABLE 2-continued

| Ex. # | Structure |
|---|---|
| 51 | 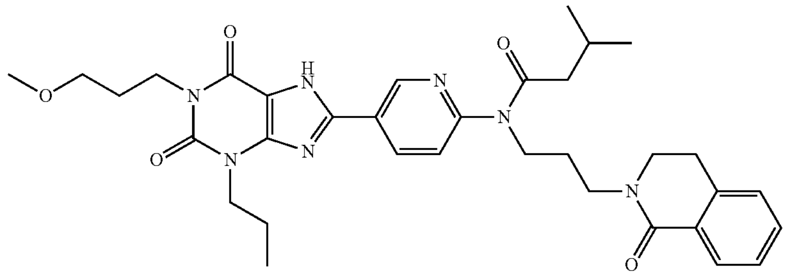 [SMILES: CCCn1c(=O)n(CCCOC)c(=O)c2[nH]c(-c3ccc(N(CCCN4CCc5ccccc5C4=O)C(=O)CC(C)C)nc3)nc21] |
| 52 | 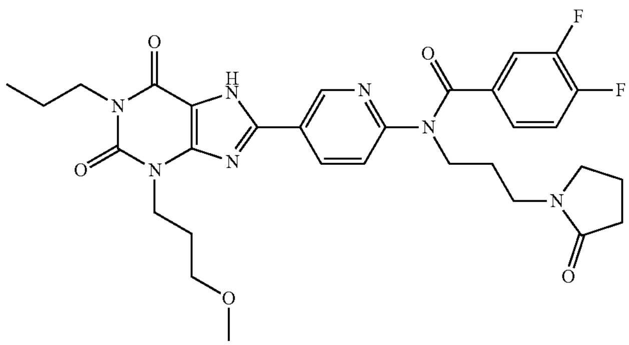 [SMILES: CCCn1c(=O)c2[nH]c(-c3ccc(N(CCCN4CCCC4=O)C(=O)c4ccc(F)c(F)c4)nc3)nc2n(CCCOC)c1=O] |
| 53 | 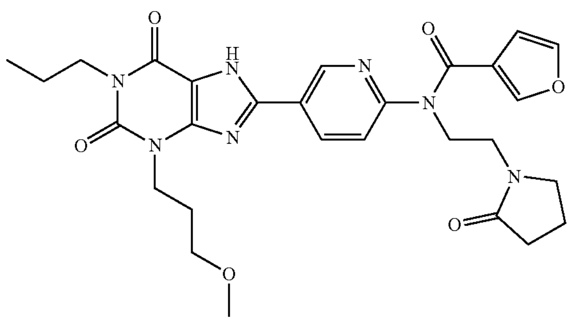 [SMILES: CCCn1c(=O)c2[nH]c(-c3ccc(N(CCN4CCCC4=O)C(=O)c4ccoc4)nc3)nc2n(CCCOC)c1=O] |
| 54 | 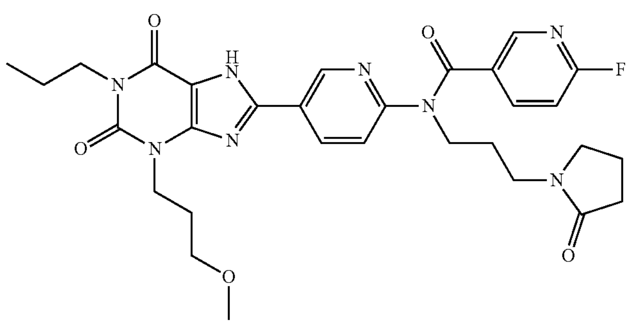 [SMILES: CCCn1c(=O)c2[nH]c(-c3ccc(N(CCCN4CCCC4=O)C(=O)c4ccc(F)nc4)nc3)nc2n(CCCOC)c1=O] |
| 55 | 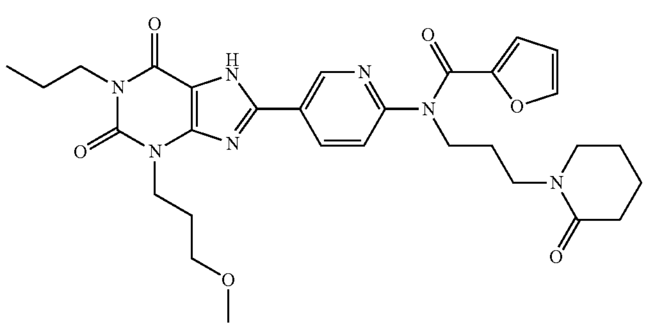 [SMILES: CCCn1c(=O)c2[nH]c(-c3ccc(N(CCCN4CCCCC4=O)C(=O)c4ccco4)nc3)nc2n(CCCOC)c1=O] |

TABLE 2-continued

| Ex. # | Structure |
|---|---|
| 56 | 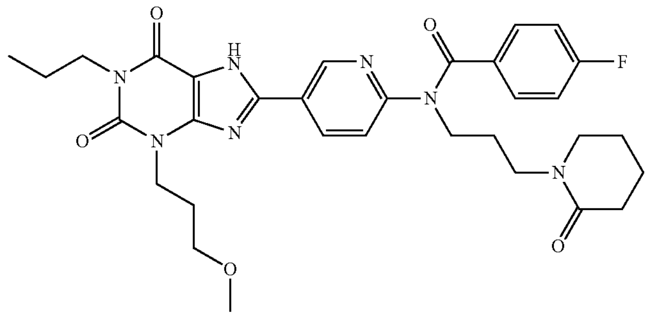 |
| 57 | 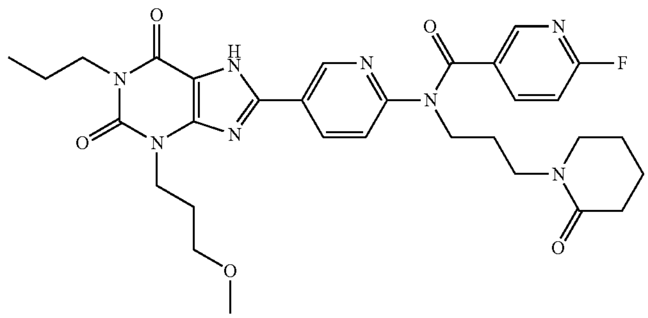 [SMILES: CCCn1c(=O)c2[nH]c(-c3ccc(N(CCCN4CCCCC4=O)C(=O)c4ccc(F)nc4)nc3)nc2n(CCCOC)c1=O] |
| 58 | 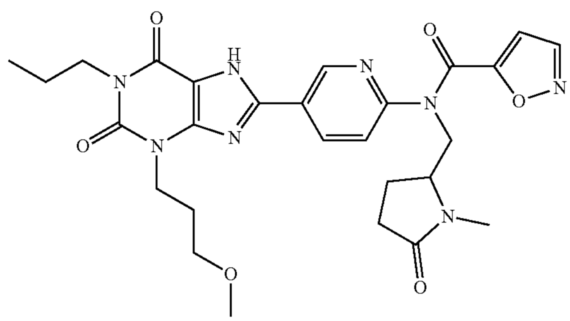 [SMILES: CCCn1c(=O)c2[nH]c(-c3ccc(N(CC4CCC(=O)N4C)C(=O)c4ccno4)nc3)nc2n(CCCOC)c1=O] |
| 59 | 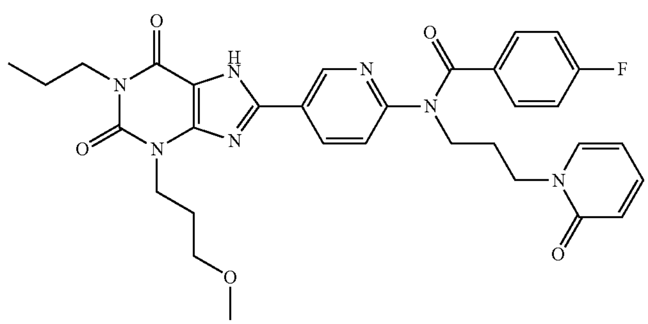 [SMILES: CCCn1c(=O)c2[nH]c(-c3ccc(N(CCCn4ccccc4=O)C(=O)c4ccc(F)cc4)nc3)nc2n(CCCOC)c1=O] |
| 60 | 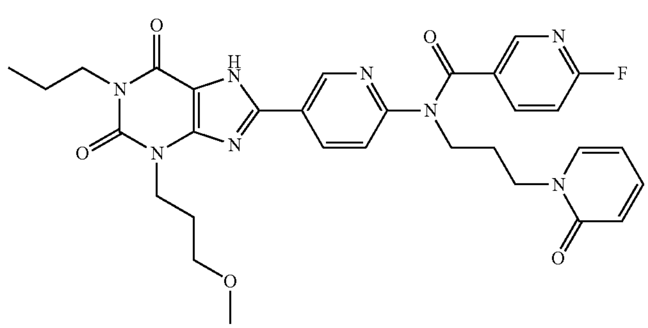 [SMILES: CCCn1c(=O)c2[nH]c(-c3ccc(N(CCCn4ccccc4=O)C(=O)c4ccc(F)nc4)nc3)nc2n(CCCOC)c1=O] |

TABLE 2-continued
| Ex. # | Structure |
|---|---|
| 61 | 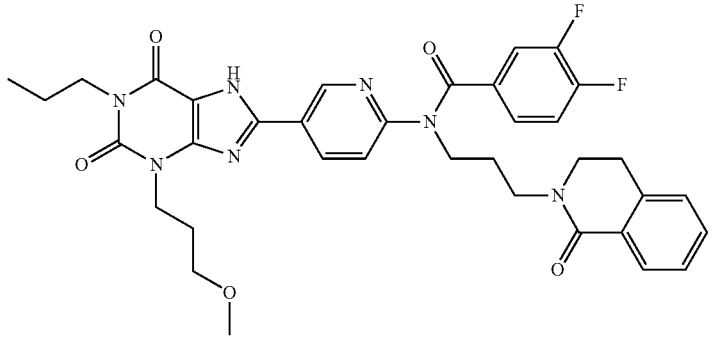 [SMILES: CCCn1c(=O)c2[nH]c(-c3ccc(N(CCCN4CCc5ccccc5C4=O)C(=O)c4ccc(F)c(F)c4)nc3)nc2n(CCCOC)c1=O] |
| 62 | 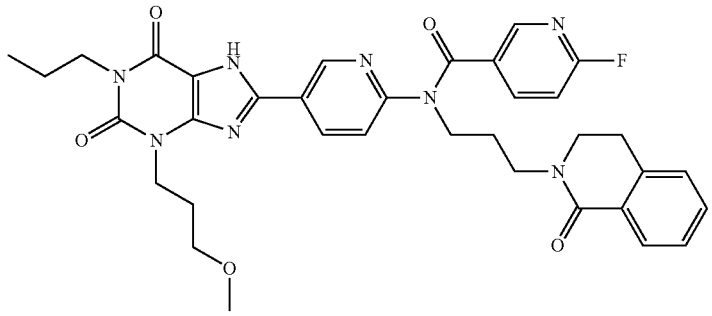 [SMILES: CCCn1c(=O)c2[nH]c(-c3ccc(N(CCCN4CCc5ccccc5C4=O)C(=O)c4ccc(F)nc4)nc3)nc2n(CCCOC)c1=O] |
| 63 | 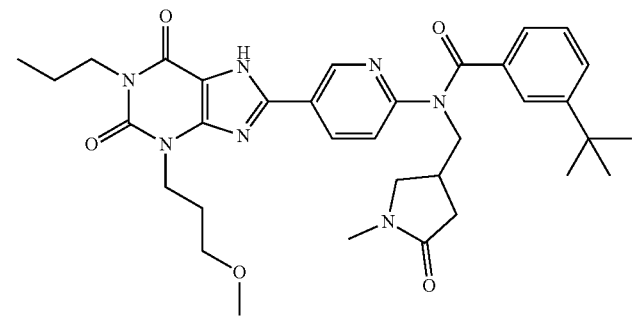 [SMILES: CCCn1c(=O)c2[nH]c(-c3ccc(N(CC4CC(=O)N(C)C4)C(=O)c4cccc(C(C)(C)C)c4)nc3)nc2n(CCCOC)c1=O] |
| 64 | 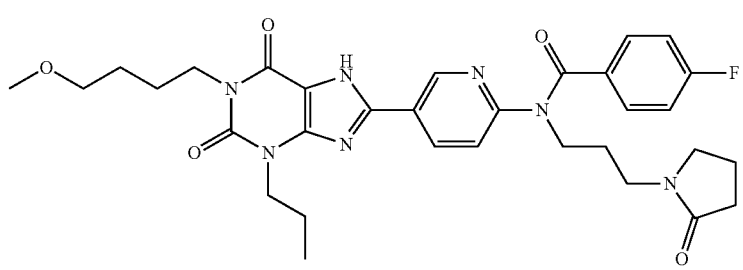 [SMILES: CCCn1c(=O)n(CCCCOC)c(=O)c2[nH]c(-c3ccc(N(CCCN4CCCC4=O)C(=O)c4ccc(F)cc4)nc3)nc21] |
| 65 | 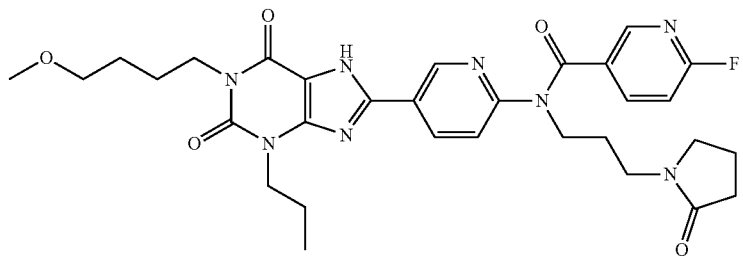 |

TABLE 2-continued
| Ex. # | Structure |
|---|---|
| 66 | 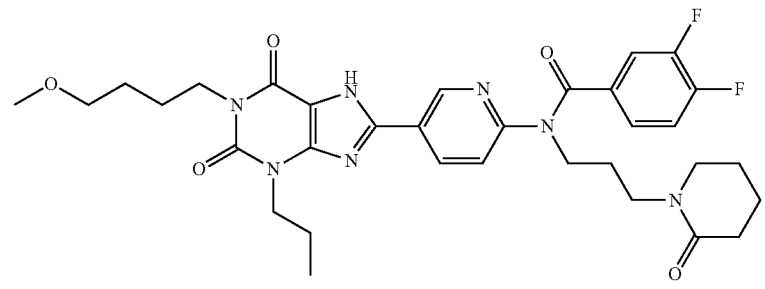 [SMILES: CCCn1c(=O)n(CCCCOC)c(=O)c2[nH]c(-c3ccc(N(CCCN4CCCCC4=O)C(=O)c4ccc(F)c(F)c4)nc3)nc21] |
| 67 | 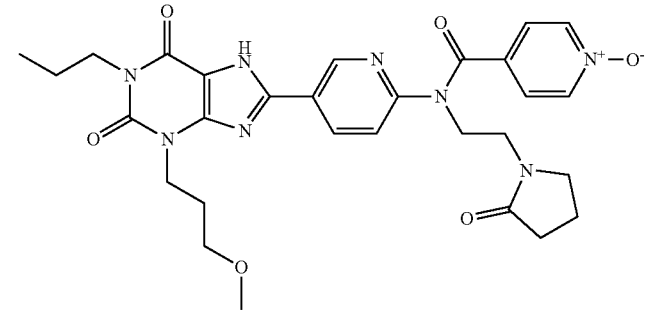 [SMILES: CCCn1c(=O)c2[nH]c(-c3ccc(N(CCN4CCCC4=O)C(=O)c4cc[n+]([O-])cc4)nc3)nc2n(CCCOC)c1=O] |
| 68 | 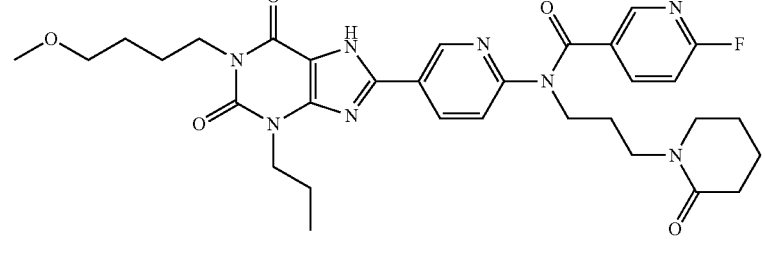 |
| 69 | 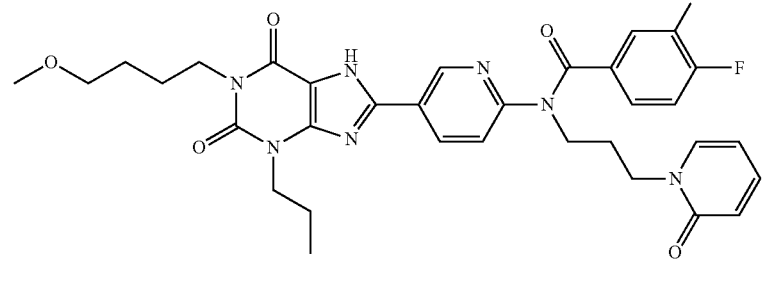 |
| 70 | 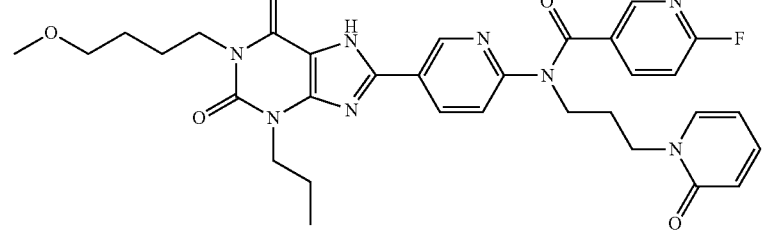 |

TABLE 2-continued
| Ex. # | Structure |
|---|---|
| 71 | 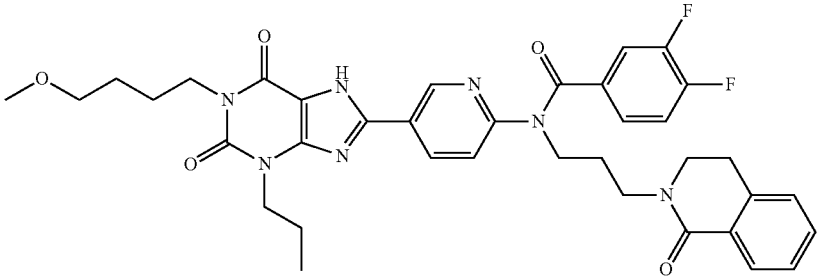 [SMILES: CCCn1c(=O)n(CCCCOC)c(=O)c2[nH]c(-c3ccc(N(CCCN4CCc5ccccc5C4=O)C(=O)c4ccc(F)c(F)c4)nc3)nc21] |
| 72 | 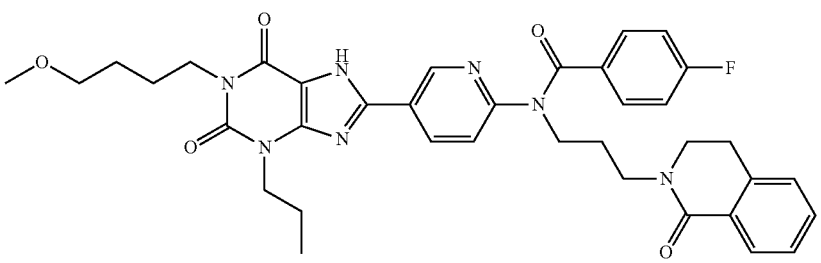 [SMILES: CCCn1c(=O)n(CCCCOC)c(=O)c2[nH]c(-c3ccc(N(CCCN4CCc5ccccc5C4=O)C(=O)c4ccc(F)cc4)nc3)nc21] |
| 73 | 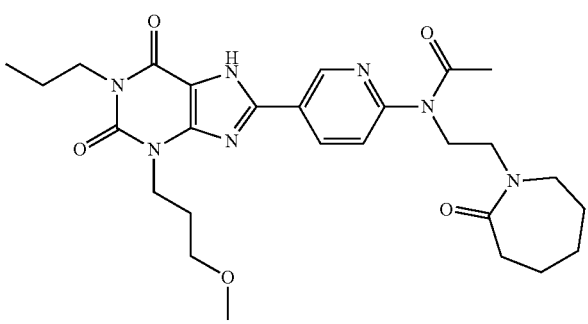 [SMILES: CCCn1c(=O)c2[nH]c(-c3ccc(N(CCN4CCCCCC4=O)C(C)=O)nc3)nc2n(CCCOC)c1=O] |
| 74 | 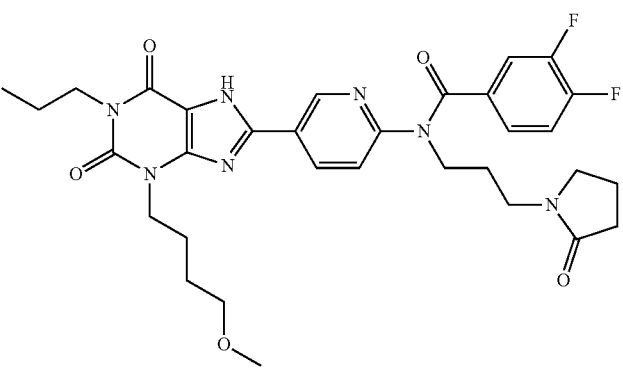 [SMILES: CCCn1c(=O)c2[nH]c(-c3ccc(N(CCCN4CCCC4=O)C(=O)c4ccc(F)c(F)c4)nc3)nc2n(CCCCOC)c1=O] |
| 75 | 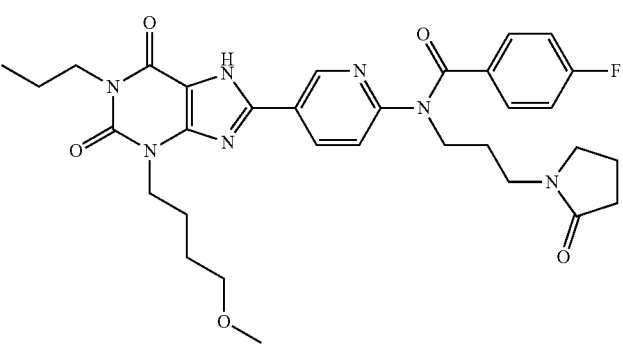 [SMILES: CCCn1c(=O)c2[nH]c(-c3ccc(N(CCCN4CCCC4=O)C(=O)c4ccc(F)cc4)nc3)nc2n(CCCCOC)c1=O] |

TABLE 2-continued

| Ex. # | Structure |
|---|---|
| 76 | 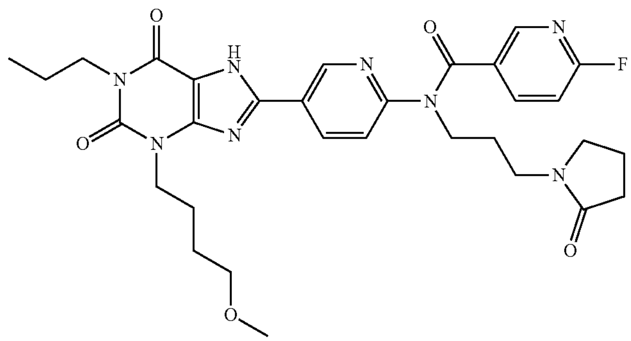 |
| 77 | 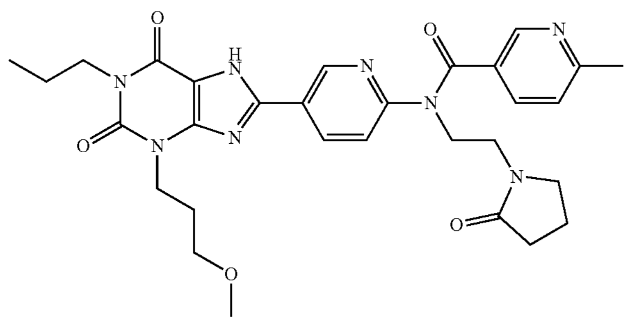 [SMILES: CCCn1c(=O)c2[nH]c(-c3ccc(N(CCN4CCCC4=O)C(=O)c4ccc(C)nc4)nc3)nc2n(CCCOC)c1=O] |
| 78 | 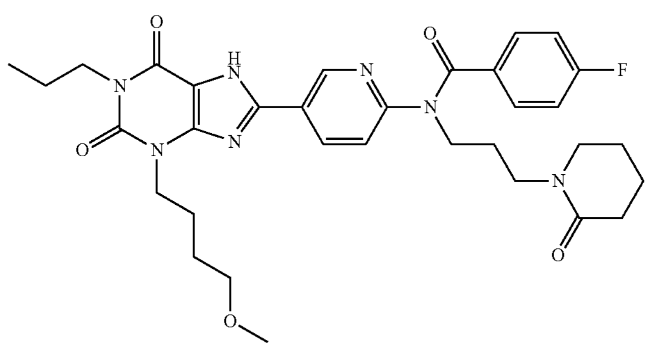 [SMILES: CCCn1c(=O)c2[nH]c(-c3ccc(N(CCCN4CCCCC4=O)C(=O)c4ccc(F)cc4)nc3)nc2n(CCCCOC)c1=O] |
| 79 | 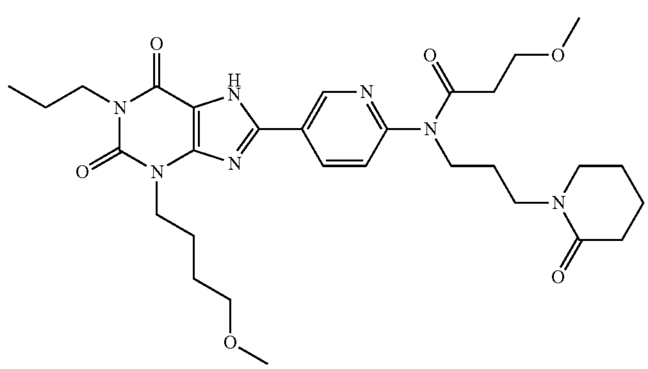 [SMILES: CCCn1c(=O)c2[nH]c(-c3ccc(N(CCCN4CCCCC4=O)C(=O)CCOC)nc3)nc2n(CCCCOC)c1=O] |

TABLE 2-continued
| Ex. # | Structure |
|---|---|
| 80 | 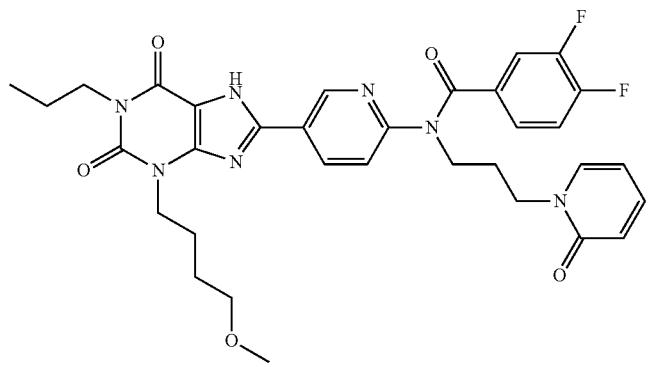 [SMILES: CCCn1c(=O)c2[nH]c(-c3ccc(N(CCCn4ccccc4=O)C(=O)c4ccc(F)c(F)c4)nc3)nc2n(CCCCOC)c1=O] |
| 81 | 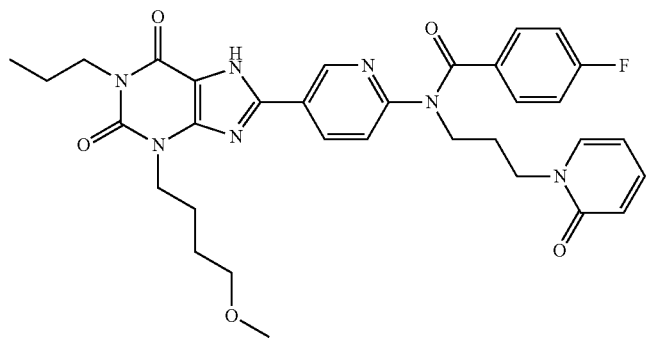 [SMILES: CCCn1c(=O)c2[nH]c(-c3ccc(N(CCCn4ccccc4=O)C(=O)c4ccc(F)cc4)nc3)nc2n(CCCCOC)c1=O] |
| 82 | 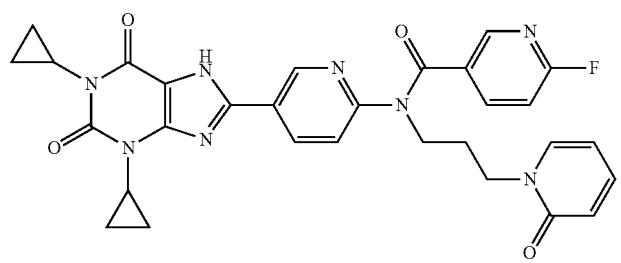 [SMILES: O=C(c1ccc(F)nc1)N(CCCn1ccccc1=O)c1ccc(-c2nc3c([nH]2)c(=O)n(C2CC2)c(=O)n3C2CC2)cn1] |
| 83 | 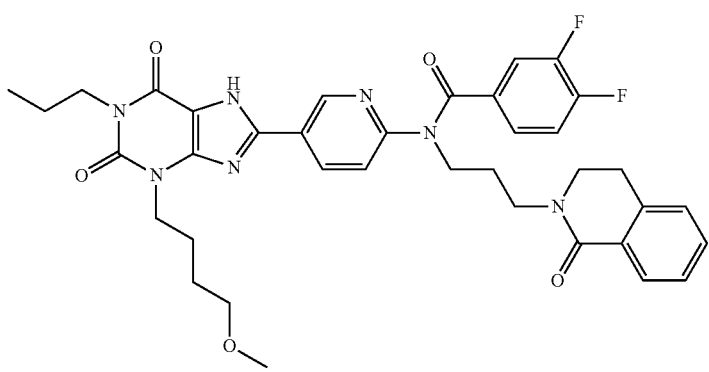 [SMILES: CCCn1c(=O)c2[nH]c(-c3ccc(N(CCCN4CCc5ccccc5C4=O)C(=O)c4ccc(F)c(F)c4)nc3)nc2n(CCCCOC)c1=O] |

TABLE 2-continued
| Ex. # | Structure |
|---|---|
| 84 | 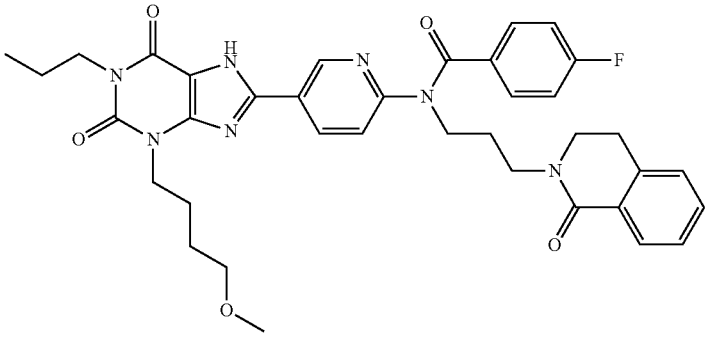 [SMILES: CCCn1c(=O)c2[nH]c(-c3ccc(N(CCCN4CCc5ccccc5C4=O)C(=O)c4ccc(F)cc4)nc3)nc2n(CCCCOC)c1=O] |
| 85 | 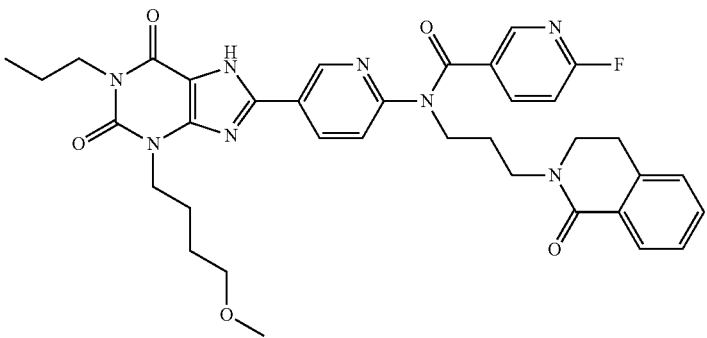 [SMILES: CCCn1c(=O)c2[nH]c(-c3ccc(N(CCCN4CCc5ccccc5C4=O)C(=O)c4ccc(F)nc4)nc3)nc2n(CCCCOC)c1=O] |
| 86 | 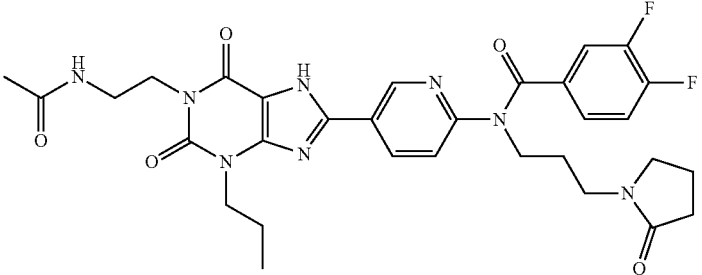 [SMILES: CCCn1c(=O)n(CCNC(C)=O)c(=O)c2[nH]c(-c3ccc(N(CCCN4CCCC4=O)C(=O)c4ccc(F)c(F)c4)nc3)nc21] |
| 87 | 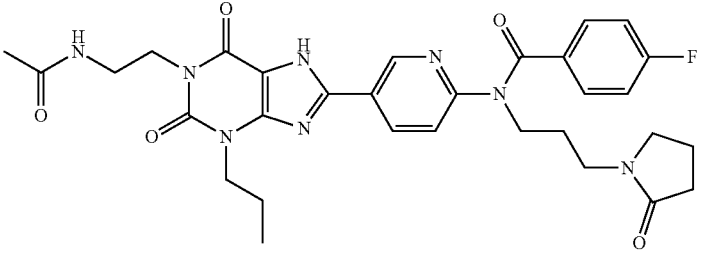 [SMILES: CCCn1c(=O)n(CCNC(C)=O)c(=O)c2[nH]c(-c3ccc(N(CCCN4CCCC4=O)C(=O)c4ccc(F)cc4)nc3)nc21] |
| 88 | 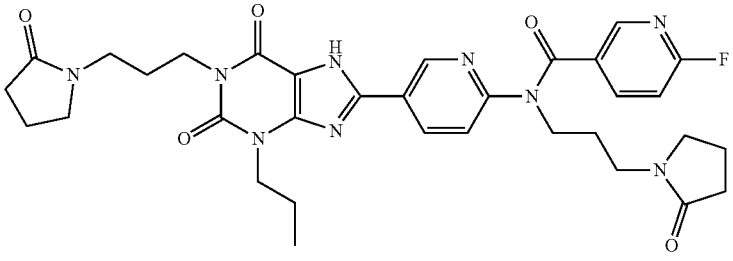 [SMILES: CCCn1c(=O)n(CCCN2CCCC2=O)c(=O)c2[nH]c(-c3ccc(N(CCCN4CCCC4=O)C(=O)c4ccc(F)nc4)nc3)nc21] |

TABLE 2-continued
| Ex. # | Structure |
|---|---|
| 89 | 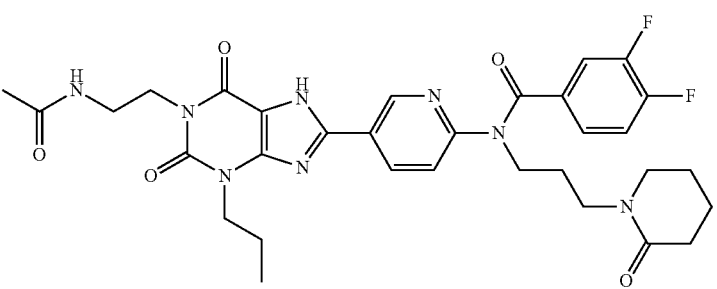 [SMILES: CCCn1c(=O)n(CCNC(C)=O)c(=O)c2[nH]c(-c3ccc(N(CCCN4CCCCC4=O)C(=O)c4ccc(F)c(F)c4)nc3)nc21] |
| 90 | 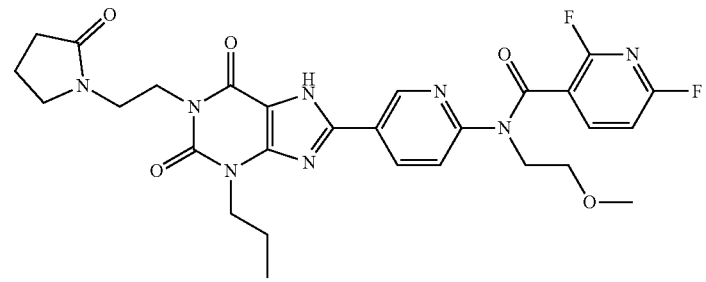 [SMILES: CCCn1c(=O)n(CCN2CCCC2=O)c(=O)c2[nH]c(-c3ccc(N(CCOC)C(=O)c4ccc(F)nc4F)nc3)nc21] |
| 91 | 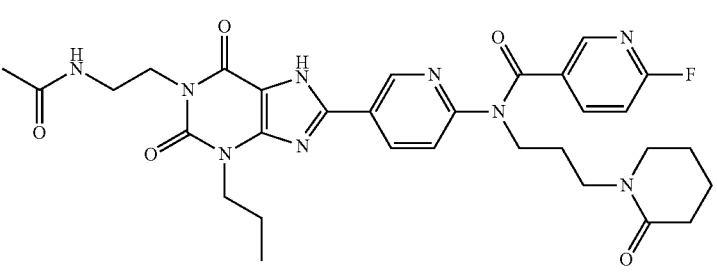 [SMILES: CCCn1c(=O)n(CCNC(C)=O)c(=O)c2[nH]c(-c3ccc(N(CCCN4CCCCC4=O)C(=O)c4ccc(F)nc4)nc3)nc21] |
| 92 | 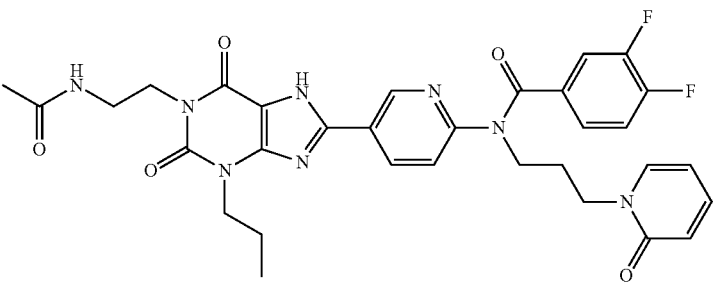 [SMILES: CCCn1c(=O)n(CCNC(C)=O)c(=O)c2[nH]c(-c3ccc(N(CCCn4ccccc4=O)C(=O)c4ccc(F)c(F)c4)nc3)nc21] |
| 93 | 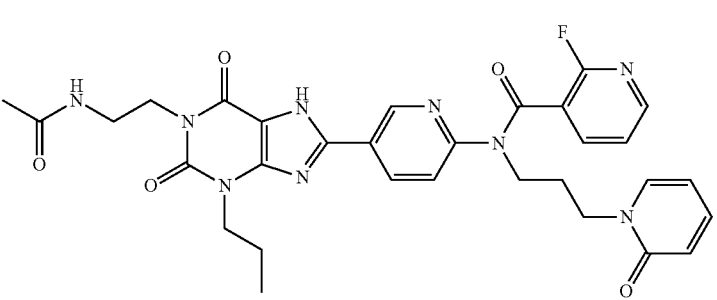 [SMILES: CCCn1c(=O)n(CCNC(C)=O)c(=O)c2[nH]c(-c3ccc(N(CCCn4ccccc4=O)C(=O)c4cccnc4F)nc3)nc21] |

TABLE 2-continued

| Ex. # | Structure |
|---|---|
| 94 | 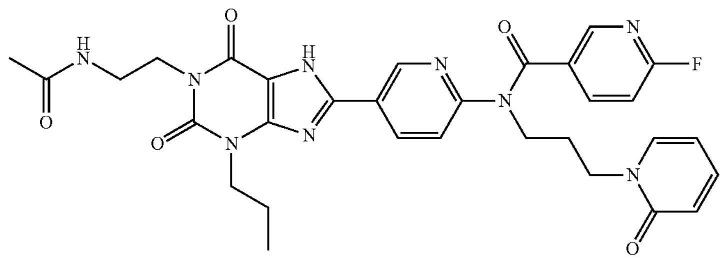 [SMILES: CCCn1c(=O)n(CCNC(C)=O)c(=O)c2[nH]c(-c3ccc(N(CCCn4ccccc4=O)C(=O)c4ccc(F)nc4)nc3)nc21] |
| 95 | 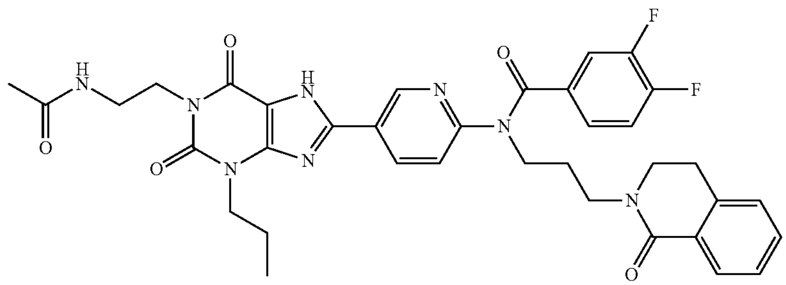 [SMILES: CCCn1c(=O)n(CCNC(C)=O)c(=O)c2[nH]c(-c3ccc(N(CCCN4CCc5ccccc5C4=O)C(=O)c4ccc(F)c(F)c4)nc3)nc21] |
| 96 | 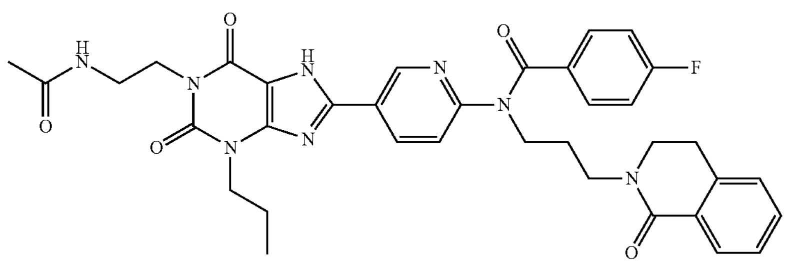 |
| 97 | 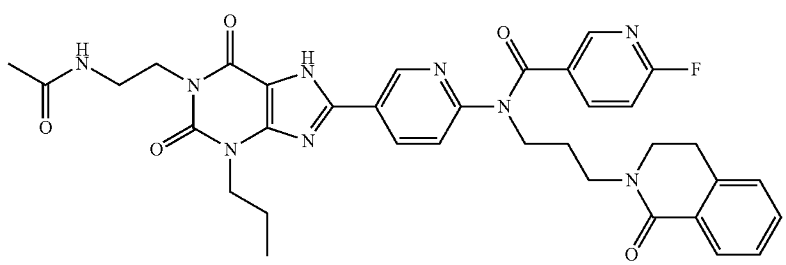 |
| 98 | 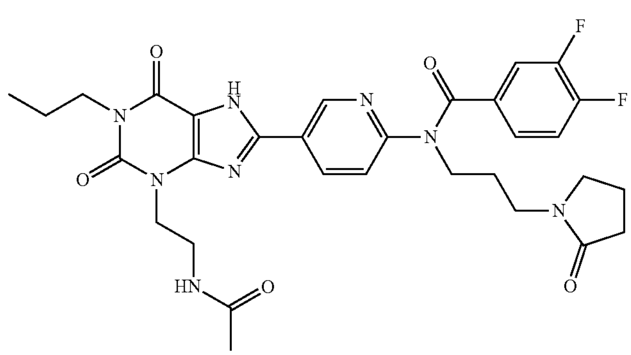 [SMILES: CCCn1c(=O)c2[nH]c(-c3ccc(N(CCCN4CCCC4=O)C(=O)c4ccc(F)c(F)c4)nc3)nc2n(CCNC(C)=O)c1=O] |

TABLE 2-continued
| Ex. # | Structure |
|---|---|
| 99 | 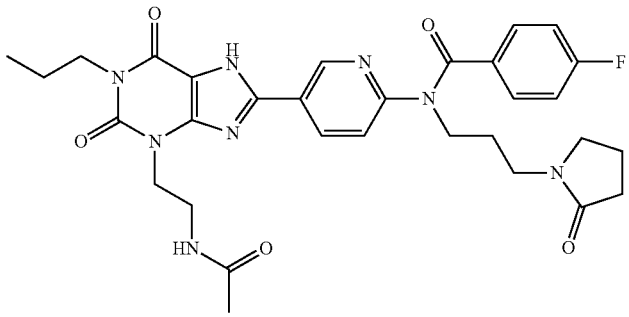 [SMILES: CCCn1c(=O)c2[nH]c(-c3ccc(N(CCCN4CCCC4=O)C(=O)c4ccc(F)cc4)nc3)nc2n(CCNC(C)=O)c1=O] |
| 100 | 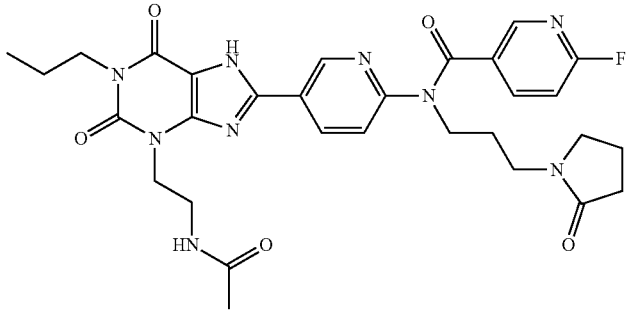 [SMILES: CCCn1c(=O)c2[nH]c(-c3ccc(N(CCCN4CCCC4=O)C(=O)c4ccc(F)nc4)nc3)nc2n(CCNC(C)=O)c1=O] |
| 101 | 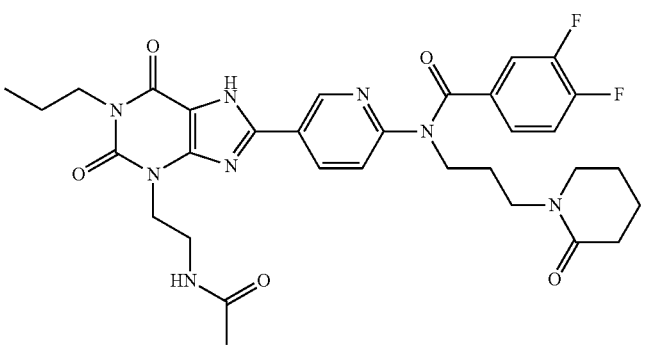 [SMILES: CCCn1c(=O)c2[nH]c(-c3ccc(N(CCCN4CCCCC4=O)C(=O)c4ccc(F)c(F)c4)nc3)nc2n(CCNC(C)=O)c1=O] |
| 102 | 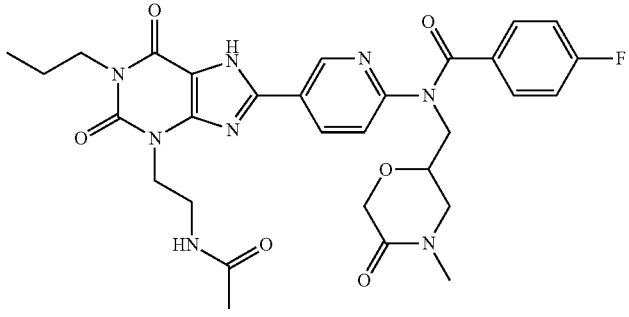 [SMILES: CCCn1c(=O)c2[nH]c(-c3ccc(N(CC4CN(C)C(=O)CO4)C(=O)c4ccc(F)cc4)nc3)nc2n(CCNC(C)=O)c1=O] |

TABLE 2-continued
| Ex. # | Structure |
|---|---|
| 103 | 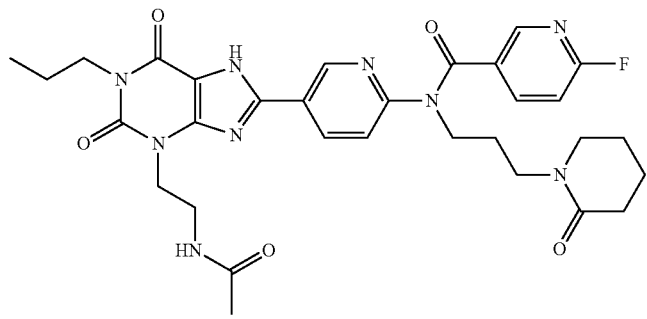 [SMILES: CCCn1c(=O)c2[nH]c(-c3ccc(N(CCCN4CCCCC4=O)C(=O)c4ccc(F)nc4)nc3)nc2n(CCNC(C)=O)c1=O] |
| 104 | 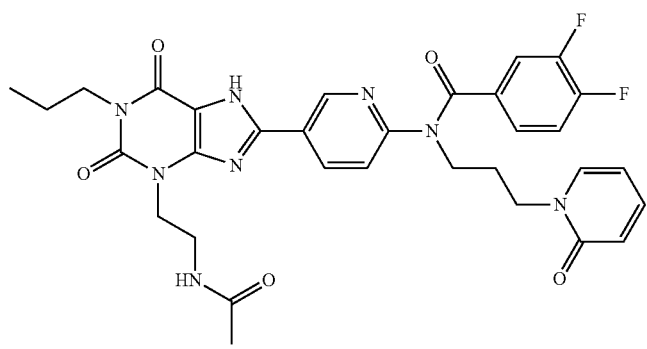 [SMILES: CCCn1c(=O)c2[nH]c(-c3ccc(N(CCCn4ccccc4=O)C(=O)c4ccc(F)c(F)c4)nc3)nc2n(CCNC(C)=O)c1=O] |
| 105 | 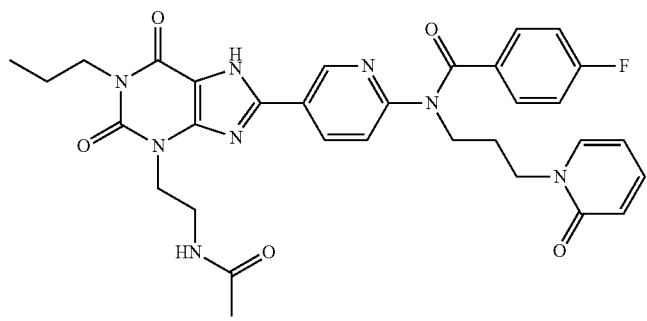 [SMILES: CCCn1c(=O)c2[nH]c(-c3ccc(N(CCCn4ccccc4=O)C(=O)c4ccc(F)cc4)nc3)nc2n(CCNC(C)=O)c1=O] |
| 106 | 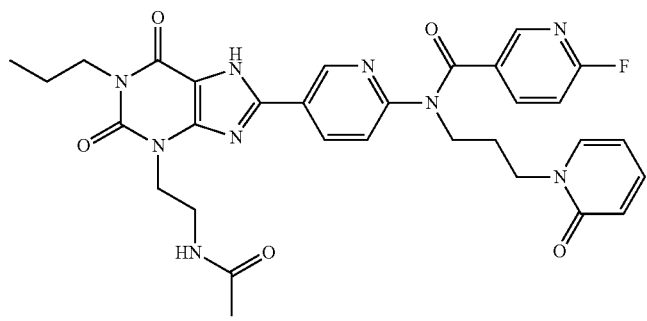 |

TABLE 2-continued
| Ex. # | Structure |
|---|---|
| 107 | 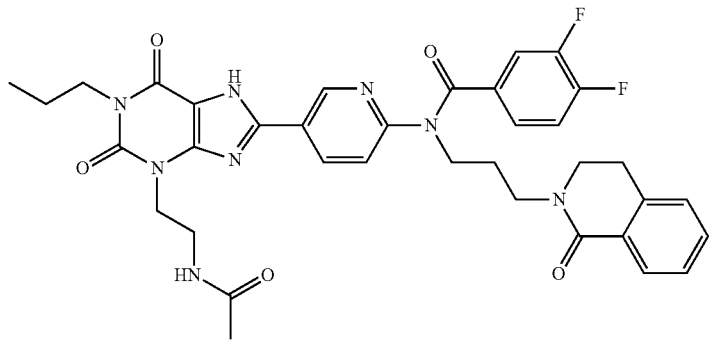 [SMILES: CCCn1c(=O)c2[nH]c(-c3ccc(N(CCCN4CCc5ccccc5C4=O)C(=O)c4ccc(F)c(F)c4)nc3)nc2n(CCNC(C)=O)c1=O] |
| 108 | 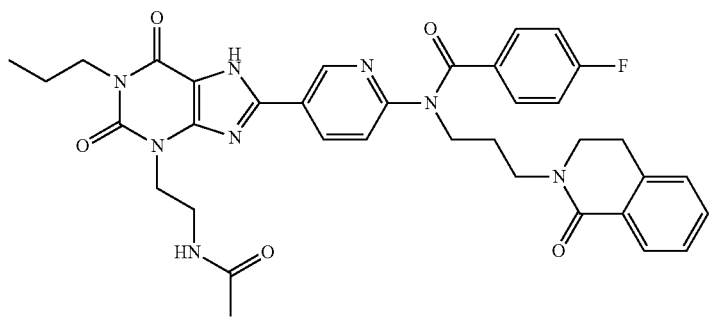 [SMILES: CCCn1c(=O)c2[nH]c(-c3ccc(N(CCCN4CCc5ccccc5C4=O)C(=O)c4ccc(F)cc4)nc3)nc2n(CCNC(C)=O)c1=O] |
| 109 | 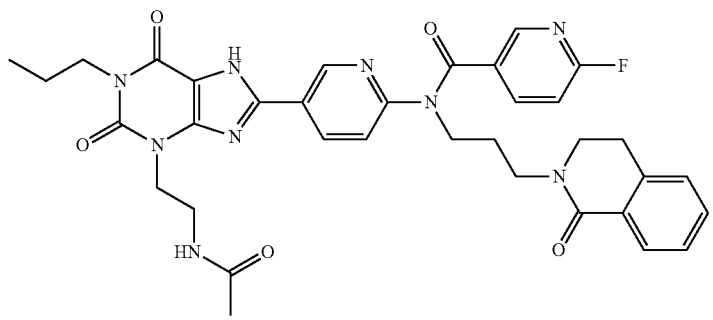 [SMILES: CCCn1c(=O)c2[nH]c(-c3ccc(N(CCCN4CCc5ccccc5C4=O)C(=O)c4ccc(F)nc4)nc3)nc2n(CCNC(C)=O)c1=O] |
| 110 | 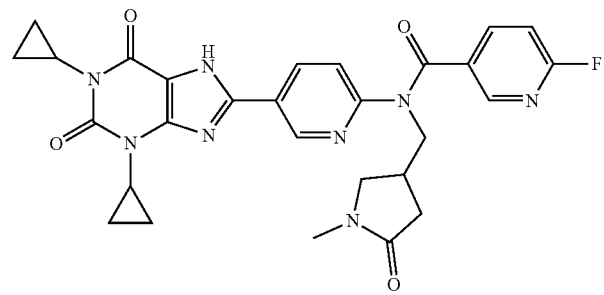 [SMILES: CN1CC(CN(C(=O)c2ccc(F)nc2)c2ccc(-c3nc4c([nH]3)c(=O)n(C3CC3)c(=O)n4C3CC3)cn2)CC1=O] |

All references listed herein are individually incorporated in their entirety by reference.

Numerous modifications and variations of the present invention are possible considering the above teachings. It is therefore to be understood that within the scope of the appended claims, the invention may be practiced otherwise than as specifically described herein.

What is claimed is:

1. A compound of formula I or a stereoisomer or pharmaceutically acceptable salt thereof:

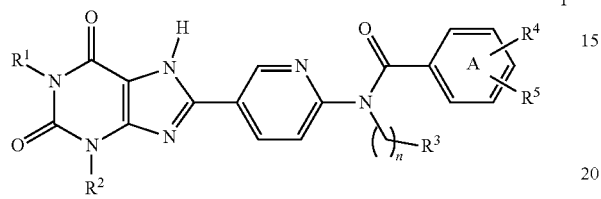

wherein:
n is selected from 1-10, wherein the $(CH_2)_n$ group is substituted with 0-1 groups selected from: $C_{1-6}$ alkyl, $C_{3-6}$ cycloalkyl, and —$C_{1-3}$ alkylene-$C_{3-6}$ cycloalkyl;
Ring A is selected from phenyl, naphthyl, and a 5-10 membered heteroaryl;
$R^1$ is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3$, and —$C_{1-6}$ alkylene-4-10 membered cyclic amide;
$R^2$ is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3$, and —$C_{1-6}$ alkylene-4-10 membered cyclic amide;
$R^3$ is a 4-10 membered cyclic amide;
$R^4$ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;
$R^5$ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;
$R^6$ is independently selected from: H, $C_{1-6}$ alkyl, $C_{3-6}$ cycloalkyl, and,
—$C_{1-3}$ alkylene-$C_{3-6}$ cycloalkyl;
$R^7$ is independently selected from: H, $C_{1-6}$ alkyl, $C_{3-6}$ cycloalkyl, and,
—$C_{1-3}$ alkylene-$C_{3-6}$ cycloalkyl; and,
p is independently selected from: 0, 1, and 2;
alternatively, $R^4$ and $R^5$ are absent, and Ring A is replaced by a group selected from: $C_{1-6}$ alkyl, $CF_3$, $C_{3-6}$ cycloalkyl, —$CH_2$—$OCH_3$, —$(CH_2)_2$—$OCH_3$, —$CH_2$—O-phenyl, and —$CH_2$—O-pyridyl;
alternatively, —$(CH_2)_n$—$R^3$ is selected from: $C_{1-6}$ alkyl, —$C_{1-3}$ alkylene-$C_{3-6}$ cycloalkyl,
—$(CH_2)_2$—$OCH_3$, —$(CH_2)_3$—$OCH_3$, and —$(CH_2)_4$—$OCH_3$, provided that at least one of $R^1$ and $R^2$ is an amide-containing group independently selected from: —$(CH_2)_2$—$NH(C(O)CH_3$ and —$C_{1-6}$ alkylene-4-10 membered cyclic amide.

2. A compound of claim 1 or a stereoisomer or pharmaceutically acceptable salt thereof, wherein:

n is selected from 2-10, wherein the $(CH_2)_n$ group is substituted with 0-1 groups selected from: $C_{1-2}$ alkyl, $C_{3-6}$ cycloalkyl, and —$C_{1-2}$ alkylene-$C_{3-6}$ cycloalkyl;
Ring A is selected from phenyl, naphthyl, and a 5-10 membered heteroaryl;
$R^1$ is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3$,

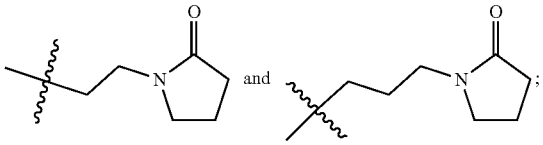 [SMILES: *CCN1CCCC1=O ; *CCCN1CCCC1=O]

$R^2$ is selected from: $C_{1-6}$ alkyl, $C_{3-6}$ cycloalkyl, —$(CH_2)_2$—$OCH_3$, —$(CH_2)_3$—$OCH_3$, —$(CH_2)_4$—$OCH_3$, —$(CH_2)_2$—$NH(C(O)CH_3$,

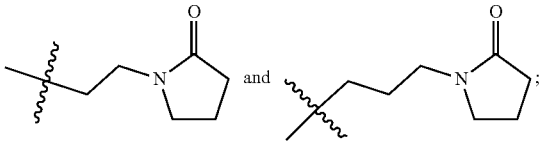

$R^3$ is selected from:

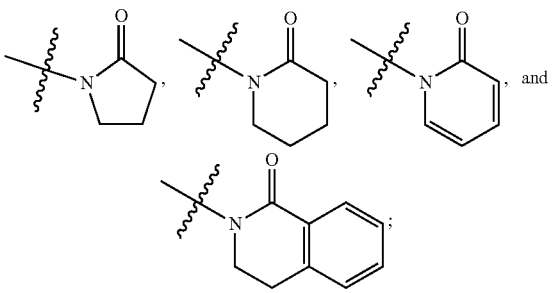

$R^4$ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;
$R^5$ is selected from: H, F, Cl, Br, I, $C_{1-6}$ alkyl, $C_{3-6}$ cycloalkyl, —$C_{1-3}$ alkylene-$C_{3-6}$ cycloalkyl, $OR^6$, $SR^6$, —CN, $NR^6R^7$, $CF_3$, $OCF_3$, $CO_2R^6$, $OC(O)R^6$, $OCO_2R^6$, $C(O)NR^6R^7$, $OC(O)NR^6R^7$, $NR^7COR^6$, $NR^7CO_2R^6$, $NR^7C(O)NR^6R^7$, and $S(O)_pNR^6R^7$;
$R^6$ is independently selected from: H, $C_{1-6}$ alkyl, $C_{3-6}$ cycloalkyl, and,
—$C_{1-3}$ alkylene-$C_{3-6}$ cycloalkyl;
$R^7$ is independently selected from: H, $C_{1-6}$ alkyl, $C_{3-6}$ cycloalkyl, and,
—$C_{1-3}$ alkylene-$C_{3-6}$ cycloalkyl; and,
p is independently selected from: 0, 1, and 2;
alternatively, —$(CH_2)_n$—$R^3$ is selected from: $C_{1-6}$ alkyl, —$C_{1-3}$ alkylene-$C_{3-6}$ cycloalkyl, —$(CH_2)_2$—$OCH_3$, —$(CH_2)_3$—$OCH_3$, and —$(CH_2)_4$—$OCH_3$, provided that at least one of $R^1$ and $R^2$ is a group independently selected from: —$(CH_2)_2$—$NH(C(O)CH_3$,

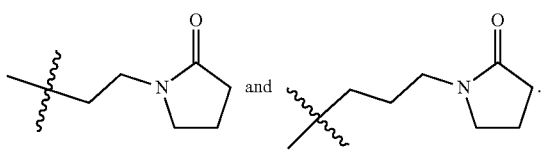 [SMILES: *CCN1CCCC1=O ; *CCCN1CCCC1=O] and .

3. A compound of claim 1 or a stereoisomer or pharmaceutically acceptable salt thereof, wherein:
n is selected from 2-4;
Ring A is selected from phenyl, pyridyl, and pyrimidyl;
$R^1$ is selected from: n-propyl, cyclopropyl, —(CH$_2$)$_2$—OCH$_3$, —(CH$_2$)$_3$—OCH$_3$, —(CH$_2$)$_4$—OCH$_3$, —(CH$_2$)$_2$—NH(C(O)CH$_3$,

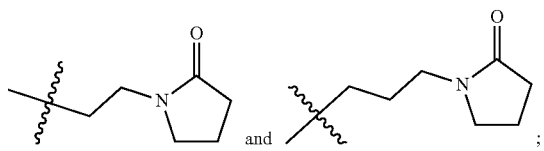 [SMILES: *CCN1CCCC1=O ; *CCCN1CCCC1=O] and ;

$R^2$ is selected from: n-propyl, cyclopropyl, —(CH$_2$)$_2$—OCH$_3$, —(CH$_2$)$_3$—OCH$_3$, —(CH$_2$)$_4$—OCH$_3$, —(CH$_2$)$_2$—NH(C(O)CH$_3$,

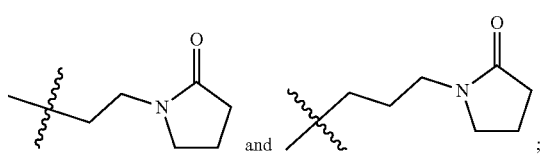 [SMILES: *CCN1CCCC1=O ; *CCCN1CCCC1=O] and ;

$R^3$ is selected from:

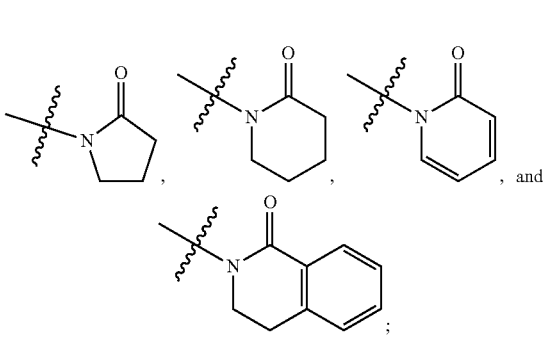, , and ;

$R^4$ is selected from: H, F, Cl, C$_{1-4}$ alkyl, C$_{3-6}$ cycloalkyl, —CH$_2$—C$_{3-6}$ cycloalkyl, OR$^6$, NR$^6$R$^7$, CF$_3$, and OCF$_3$;
$R^5$ is selected from: H, F, Cl, C$_{1-4}$ alkyl, C$_{3-6}$ cycloalkyl, —CH$_2$—C$_{3-6}$ cycloalkyl, OR$^6$, NR$^6$R$^7$, CF$_3$, and OCF$_3$;
$R^6$ is independently selected from: H, C$_{1-4}$ alkyl, C$_{3-6}$ cycloalkyl, and, —CH$_2$—C$_{3-6}$ cycloalkyl;
$R^7$ is independently selected from: H, C$_{1-4}$ alkyl, C$_{3-6}$ cycloalkyl, and, —CH$_2$—C$_{3-6}$ cycloalkyl;
alternatively, —(CH$_2$)$_n$—R$^3$ is selected from: C$_{1-4}$ alkyl, —CH$_2$—C$_{3-6}$ cycloalkyl, —(CH$_2$)$_2$—OCH$_3$, —(CH$_2$)$_3$—OCH$_3$, and —(CH$_2$)$_4$—OCH$_3$, provided that at least one of R$^1$ and R$^2$ is a group independently selected from: —(CH$_2$)$_2$—NH(C(O)CH$_3$.

4. A compound of claim 1 or a stereoisomer or pharmaceutically acceptable salt thereof, wherein:
n is selected from 2-4;
Ring A is selected from phenyl and pyridyl;
$R^1$ is selected from: n-propyl, cyclopropyl, —(CH$_2$)$_2$—OCH$_3$, —(CH$_2$)$_3$—OCH$_3$,

 and ;

$R^2$ is selected from: n-propyl, cyclopropyl, —(CH$_2$)$_2$—OCH$_3$, —(CH$_2$)$_3$—OCH$_3$,

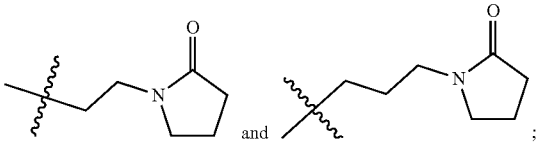 [SMILES: *CCN1CCCC1=O ; *CCCN1CCCC1=O]

$R^3$ is

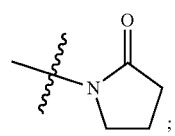;

$R^4$ is selected from: H, F, Cl, C$_{1-4}$ alkyl, C$_{3-6}$ cycloalkyl, —C$_1$ alkylene-C$_{3-6}$ cycloalkyl, and OR$^6$;
$R^5$ is selected from: H and F;
$R^6$ is independently selected from: H and C$_{1-4}$ alkyl;
alternatively, —(CH$_2$)$_n$—R$^3$ is selected from: —(CH$_2$)$_2$—OCH$_3$, and —(CH$_2$)$_3$—OCH$_3$, provided that at least one of R$^1$ and R$^2$ is a group independently selected from:

5. A compound of claim 1 or a stereoisomer or pharmaceutically acceptable salt thereof, wherein:
n is selected from 2-3;
Ring A is selected from phenyl and pyridyl;
$R^1$ is selected from: n-propyl, cyclopropyl, —(CH$_2$)$_2$—OCH$_3$, —(CH$_2$)$_3$—OCH$_3$,

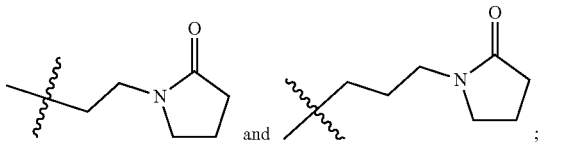 [SMILES: *CCN1CCCC1=O ; *CCCN1CCCC1=O] and ;

R² is selected from: n-propyl, cyclopropyl, —(CH₂)₂—OCH₃, and —(CH₂)₃—OCH₃;

R³ is

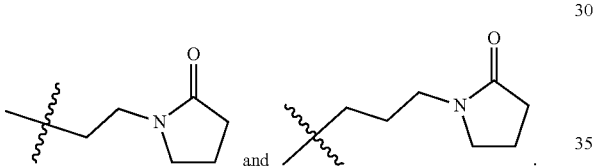 ;

R⁴ is selected from: H, F, Cl, CH₃, cyclopropyl, and OR⁶;
R⁵ is selected from: H and F;
R⁶ is independently selected from: H and CH₃;
alternatively, —(CH₂)ₙ—R³ is selected from: —(CH₂)₂—OCH₃, and —(CH₂)₃—OCH₃, provided that R¹ is selected from:

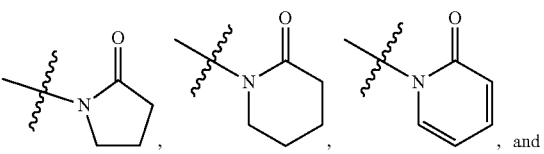 and .

6. A compound of claim 2 or a stereoisomer or pharmaceutically acceptable salt thereof, wherein:
R³ is selected from:

, , , and

7. A compound of claim 3 or a stereoisomer or pharmaceutically acceptable salt thereof, wherein:
R³ is selected from:

, , , and

.

8. A compound of claim 4 or a stereoisomer or pharmaceutically acceptable salt thereof, wherein:
R³ is

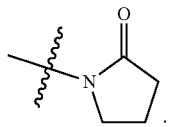 .

9. A compound of claim 5 or a stereoisomer or pharmaceutically acceptable salt thereof, wherein:
R³ is

.

10. A compound of claim 1, wherein the compound is selected from compounds of Table 1:

TABLE 1

1

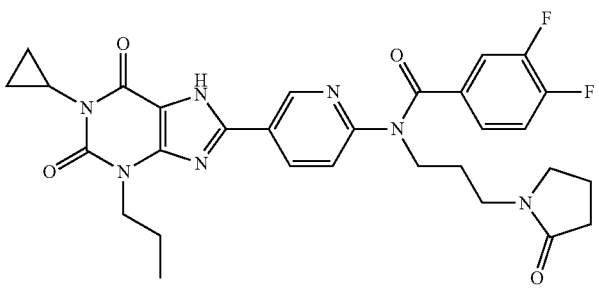 [SMILES: CCCn1c(=O)n(C2CC2)c(=O)c2[nH]c(-c3ccc(N(CCCN4CCCC4=O)C(=O)c4ccc(F)c(F)c4)nc3)nc21]

TABLE 1-continued
2 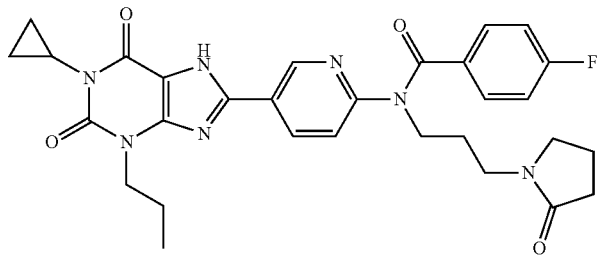
3 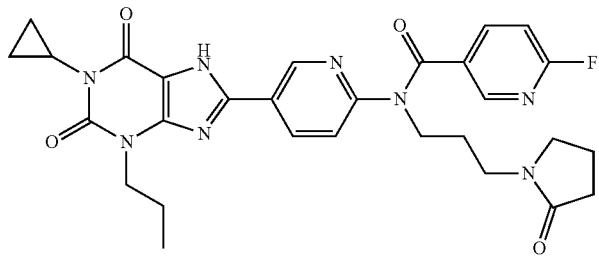
4 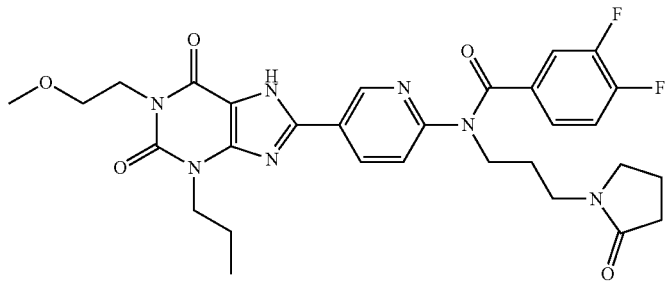 [SMILES: CCCn1c(=O)n(CCOC)c(=O)c2[nH]c(-c3ccc(N(CCCN4CCCC4=O)C(=O)c4ccc(F)c(F)c4)nc3)nc21]
5 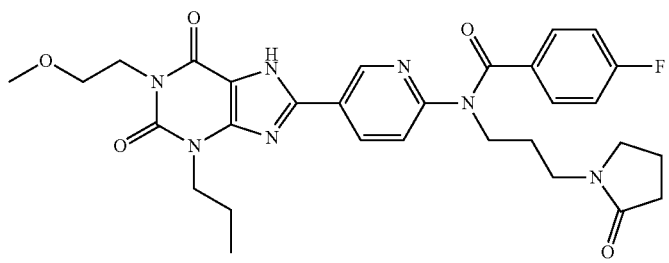
6 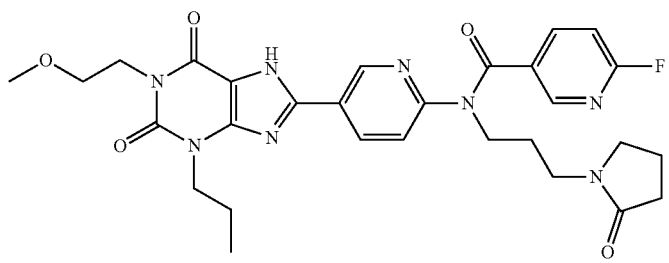
7 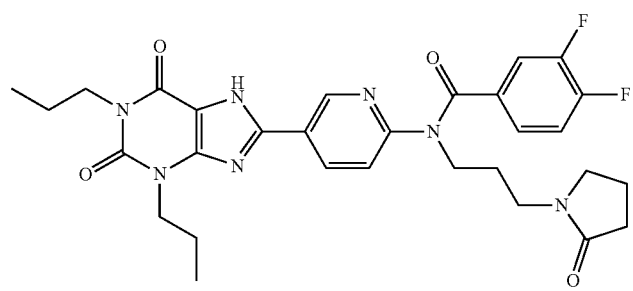 [SMILES: CCCn1c(=O)c2[nH]c(-c3ccc(N(CCCN4CCCC4=O)C(=O)c4ccc(F)c(F)c4)nc3)nc2n(CCC)c1=O]

TABLE 1-continued
8 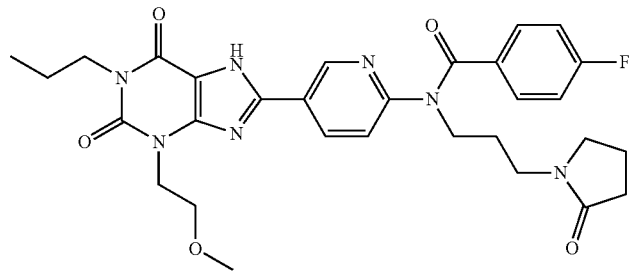
9 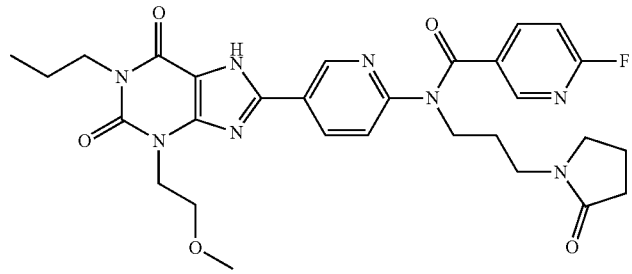
10 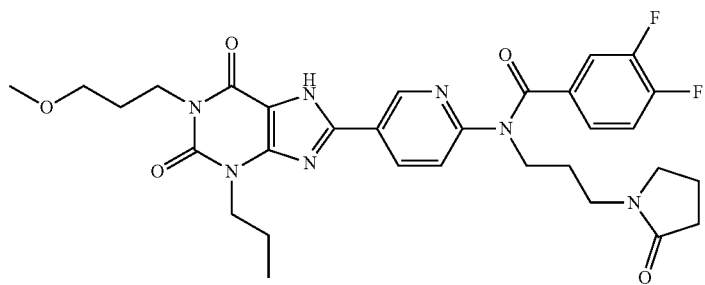 [SMILES: CCCn1c(=O)n(CCCOC)c(=O)c2[nH]c(-c3ccc(N(CCCN4CCCC4=O)C(=O)c4ccc(F)c(F)c4)nc3)nc21]
11 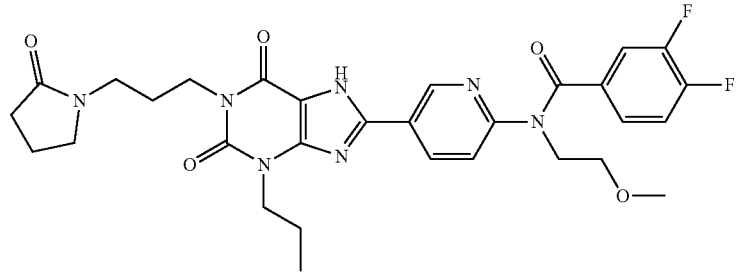 [SMILES: CCCn1c(=O)n(CCCN2CCCC2=O)c(=O)c2[nH]c(-c3ccc(N(CCOC)C(=O)c4ccc(F)c(F)c4)nc3)nc21]
12 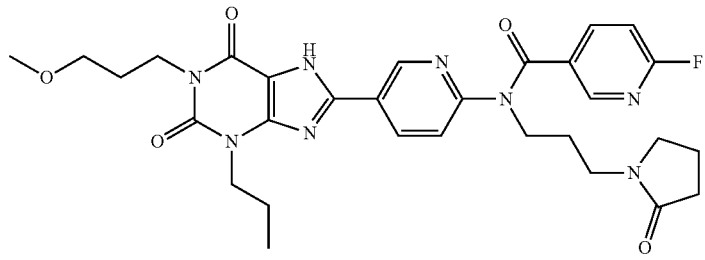 [SMILES: CCCn1c(=O)n(CCCOC)c(=O)c2[nH]c(-c3ccc(N(CCCN4CCCC4=O)C(=O)c4ccc(F)nc4)nc3)nc21]
13 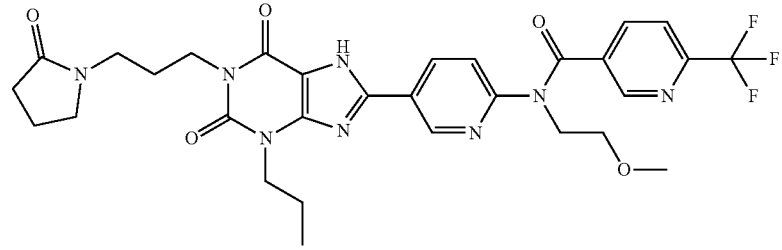 [SMILES: CCCn1c(=O)n(CCCN2CCCC2=O)c(=O)c2[nH]c(-c3ccc(N(CCOC)C(=O)c4ccc(C(F)(F)F)nc4)nc3)nc21]

TABLE 1-continued
14
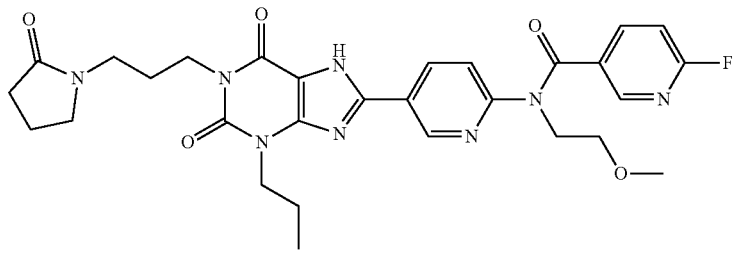
15
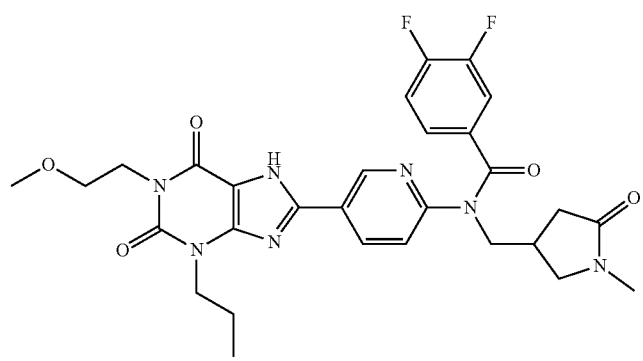
16
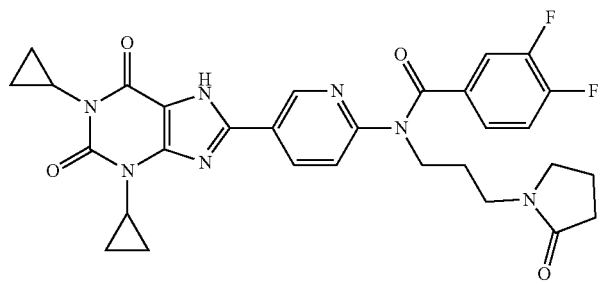 [SMILES: O=C1CCCN1CCCN(C(=O)c1ccc(F)c(F)c1)c1ccc(-c2nc3c([nH]2)c(=O)n(C2CC2)c(=O)n3C2CC2)cn1]
17
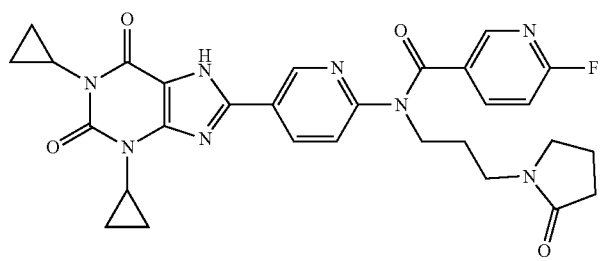 [SMILES: O=C1CCCN1CCCN(C(=O)c1ccc(F)nc1)c1ccc(-c2nc3c([nH]2)c(=O)n(C2CC2)c(=O)n3C2CC2)cn1]
18
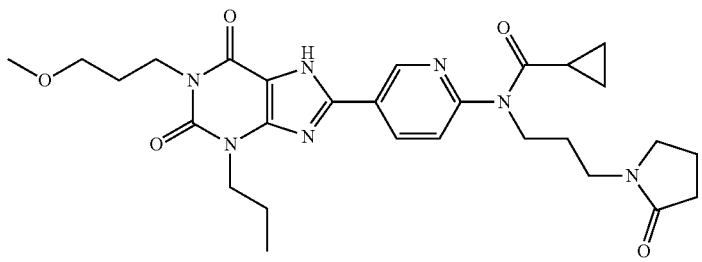 [SMILES: CCCn1c(=O)n(CCCOC)c(=O)c2[nH]c(-c3ccc(N(CCCN4CCCC4=O)C(=O)C4CC4)nc3)nc21]

TABLE 1-continued
19
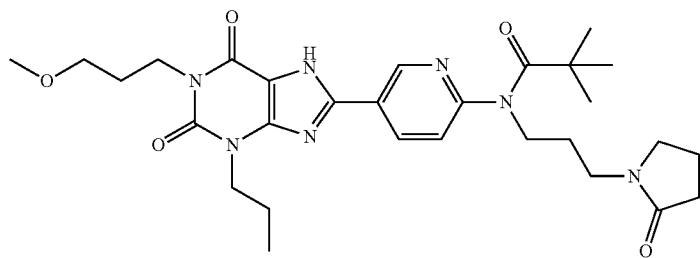 [SMILES: CCCn1c(=O)n(CCCOC)c(=O)c2[nH]c(-c3ccc(N(CCCN4CCCC4=O)C(=O)C(C)(C)C)nc3)nc21]
20
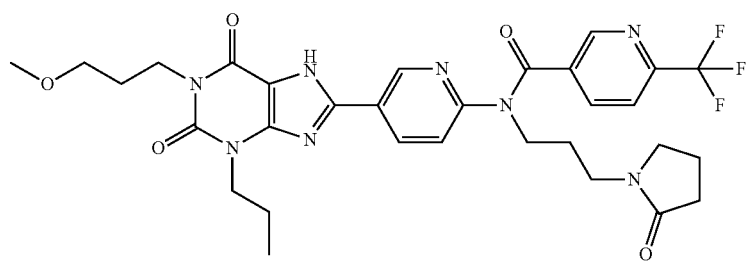 [SMILES: CCCn1c(=O)n(CCCOC)c(=O)c2[nH]c(-c3ccc(N(CCCN4CCCC4=O)C(=O)c4ccc(C(F)(F)F)nc4)nc3)nc21]
21
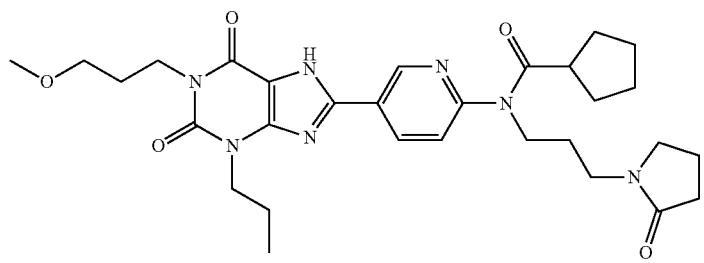 [SMILES: CCCn1c(=O)n(CCCOC)c(=O)c2[nH]c(-c3ccc(N(CCCN4CCCC4=O)C(=O)C4CCCC4)nc3)nc21]
22
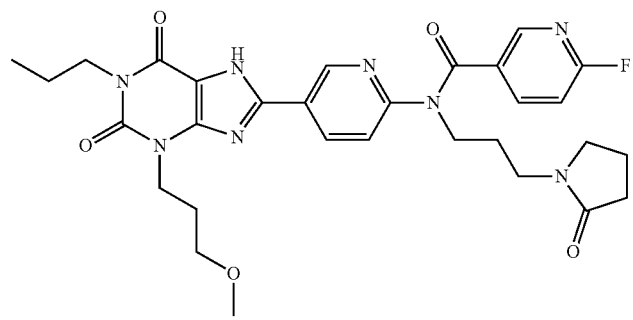 [SMILES: CCCn1c(=O)c2[nH]c(-c3ccc(N(CCCN4CCCC4=O)C(=O)c4ccc(F)nc4)nc3)nc2n(CCCOC)c1=O]
23
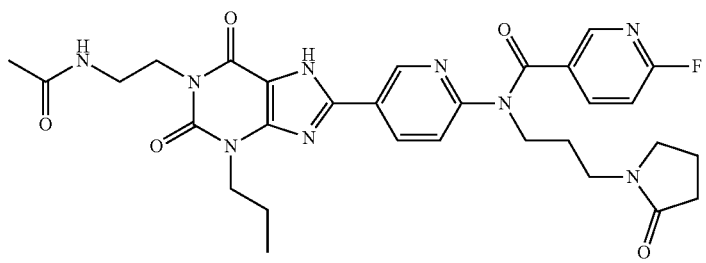

TABLE 1-continued
24
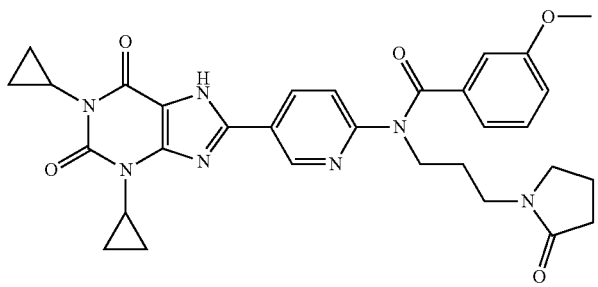 [SMILES: COc1cccc(C(=O)N(CCCN2CCCC2=O)c2ccc(-c3nc4c([nH]3)c(=O)n(C3CC3)c(=O)n4C3CC3)cn2)c1]
25
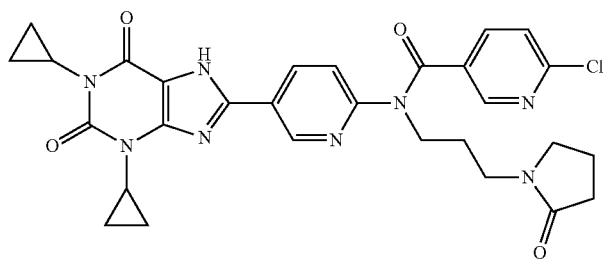 [SMILES: O=C1CCCN1CCCN(C(=O)c1ccc(Cl)nc1)c1ccc(-c2nc3c([nH]2)c(=O)n(C2CC2)c(=O)n3C2CC2)cn1]
26
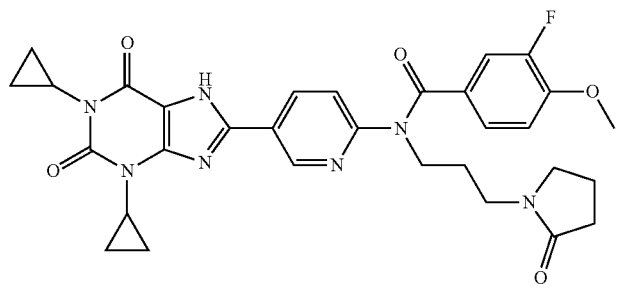 [SMILES: COc1ccc(C(=O)N(CCCN2CCCC2=O)c2ccc(-c3nc4c([nH]3)c(=O)n(C3CC3)c(=O)n4C3CC3)cn2)cc1F]
27
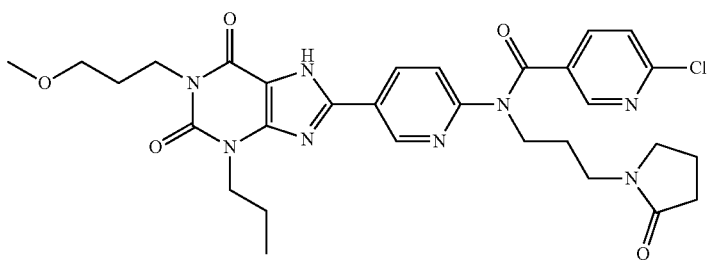 [SMILES: CCCn1c(=O)n(CCCOC)c(=O)c2[nH]c(-c3ccc(N(CCCN4CCCC4=O)C(=O)c4ccc(Cl)nc4)nc3)nc21]
28
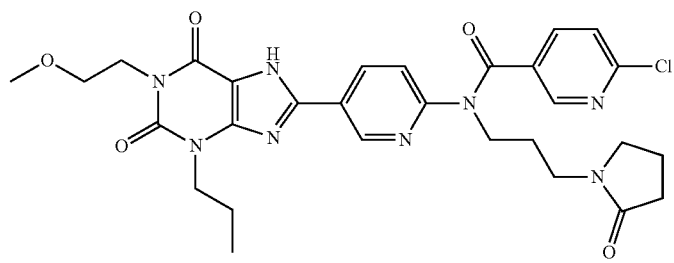 [SMILES: CCCn1c(=O)n(CCOC)c(=O)c2[nH]c(-c3ccc(N(CCCN4CCCC4=O)C(=O)c4ccc(Cl)nc4)nc3)nc21]

TABLE 1-continued
29
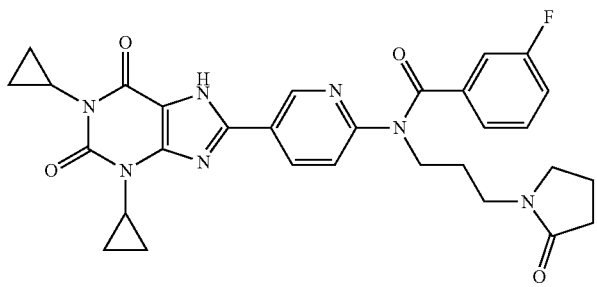 [SMILES: O=C1CCCN1CCCN(C(=O)c1cccc(F)c1)c1ccc(-c2nc3c([nH]2)c(=O)n(C2CC2)c(=O)n3C2CC2)cn1]
30
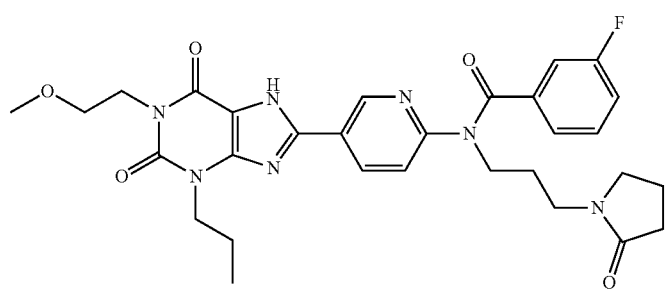 [SMILES: CCCn1c(=O)n(CCOC)c(=O)c2[nH]c(-c3ccc(N(CCCN4CCCC4=O)C(=O)c4cccc(F)c4)nc3)nc21]
31
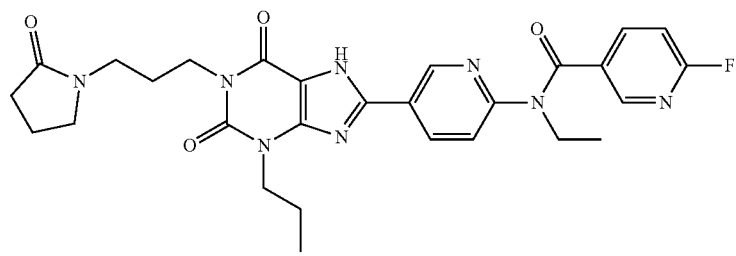 [SMILES: CCCn1c(=O)n(CCCN2CCCC2=O)c(=O)c2[nH]c(-c3ccc(N(CC)C(=O)c4ccc(F)nc4)nc3)nc21]
32
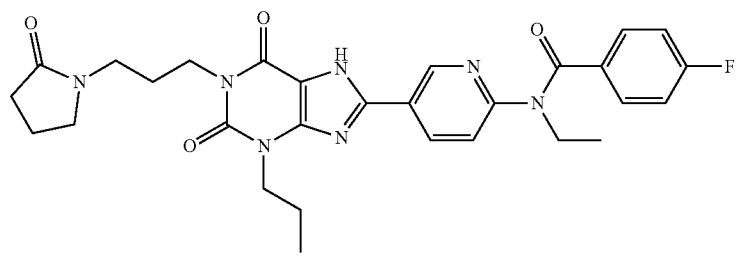 [SMILES: CCCn1c(=O)n(CCCN2CCCC2=O)c(=O)c2[nH]c(-c3ccc(N(CC)C(=O)c4ccc(F)cc4)nc3)nc21]
33
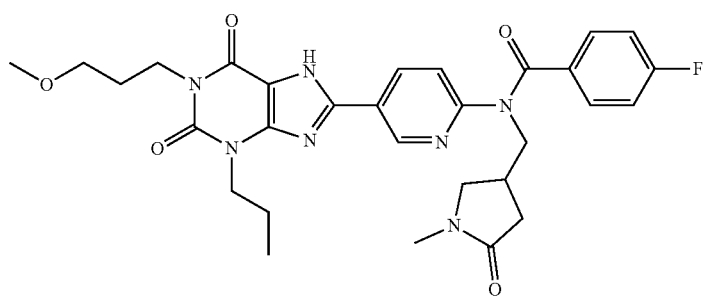 [SMILES: CCCn1c(=O)n(CCCOC)c(=O)c2[nH]c(-c3ccc(N(CC4CC(=O)N(C)C4)C(=O)c4ccc(F)cc4)nc3)nc21]

TABLE 1-continued
34 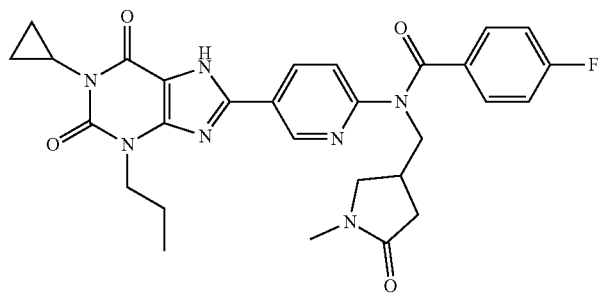 [SMILES: CCCn1c(=O)n(C2CC2)c(=O)c2[nH]c(-c3ccc(N(CC4CC(=O)N(C)C4)C(=O)c4ccc(F)cc4)nc3)nc21]
35 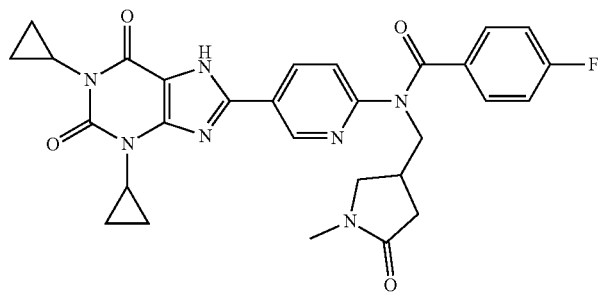
or a stereoisomer or pharmaceutically acceptable salt thereof.
11. A compound of claim 1, wherein the compound is selected from compounds of Table 2;
TABLE 2
1 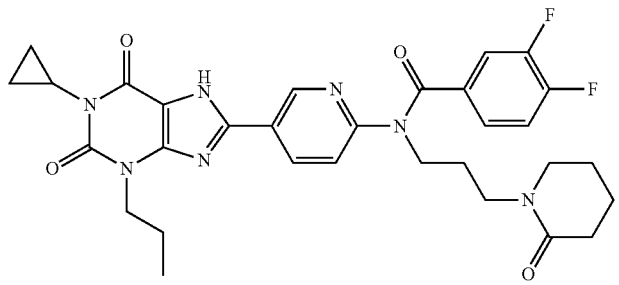 [SMILES: CCCn1c(=O)n(C2CC2)c(=O)c2[nH]c(-c3ccc(N(CCCN4CCCCC4=O)C(=O)c4ccc(F)c(F)c4)nc3)nc21]
2 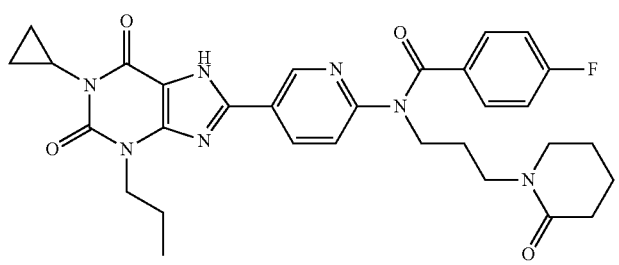 [SMILES: CCCn1c(=O)n(C2CC2)c(=O)c2[nH]c(-c3ccc(N(CCCN4CCCCC4=O)C(=O)c4ccc(F)cc4)nc3)nc21]
3 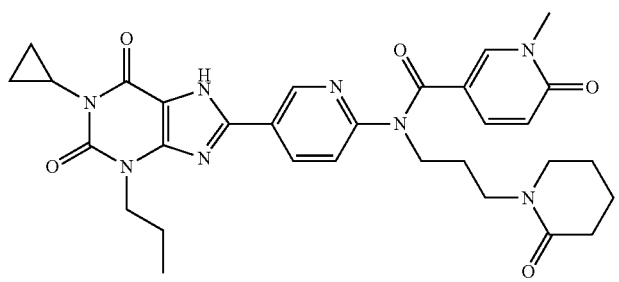 [SMILES: CCCn1c(=O)n(C2CC2)c(=O)c2[nH]c(-c3ccc(N(CCCN4CCCCC4=O)C(=O)c4ccc(=O)n(C)c4)nc3)nc21]

TABLE 2-continued
4
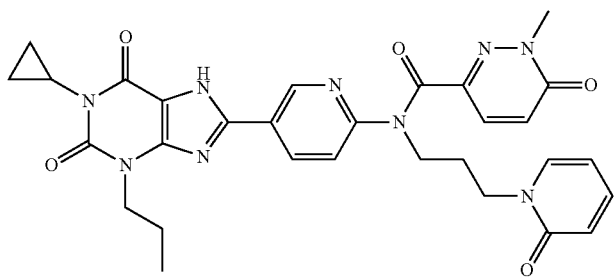 [SMILES: CCCn1c(=O)n(C2CC2)c(=O)c2[nH]c(-c3ccc(N(CCCn4ccccc4=O)C(=O)c4ccc(=O)n(C)n4)nc3)nc21]
5
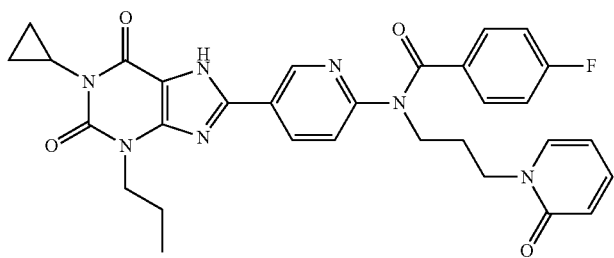 [SMILES: CCCn1c(=O)n(C2CC2)c(=O)c2[nH]c(-c3ccc(N(CCCn4ccccc4=O)C(=O)c4ccc(F)cc4)nc3)nc21]
6
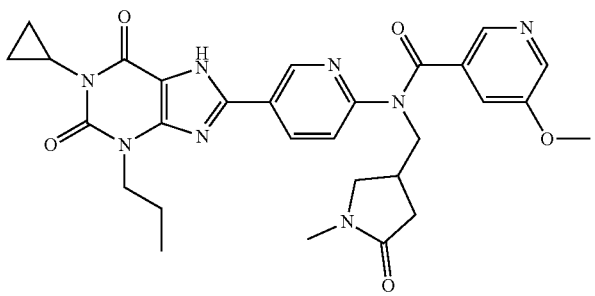 [SMILES: CCCn1c(=O)n(C2CC2)c(=O)c2[nH]c(-c3ccc(N(CC4CC(=O)N(C)C4)C(=O)c4cncc(OC)c4)nc3)nc21]
7
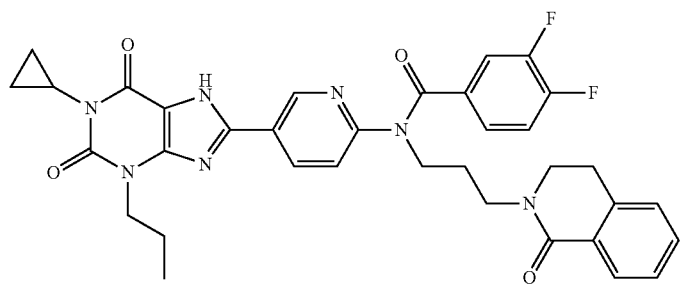 [SMILES: CCCn1c(=O)n(C2CC2)c(=O)c2[nH]c(-c3ccc(N(CCCN4CCc5ccccc5C4=O)C(=O)c4ccc(F)c(F)c4)nc3)nc21]
8
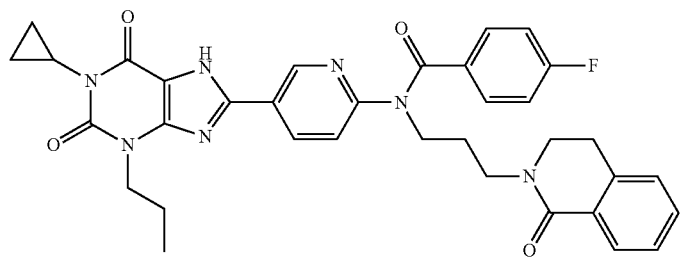 [SMILES: CCCn1c(=O)n(C2CC2)c(=O)c2[nH]c(-c3ccc(N(CCCN4CCc5ccccc5C4=O)C(=O)c4ccc(F)cc4)nc3)nc21]

TABLE 2-continued
9
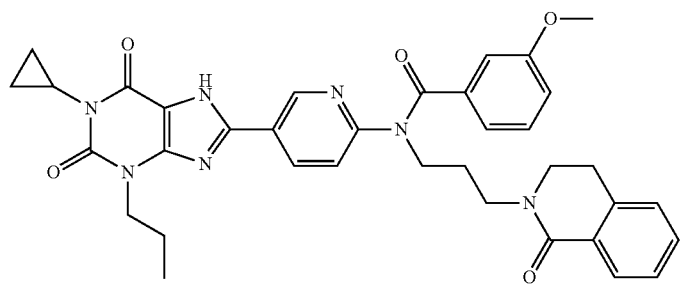 [SMILES: CCCn1c(=O)n(C2CC2)c(=O)c2[nH]c(-c3ccc(N(CCCN4CCc5ccccc5C4=O)C(=O)c4cccc(OC)c4)nc3)nc21]
10
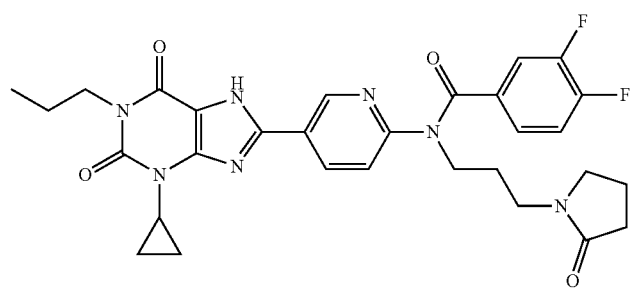 [SMILES: CCCn1c(=O)c2[nH]c(-c3ccc(N(CCCN4CCCC4=O)C(=O)c4ccc(F)c(F)c4)nc3)nc2n(C2CC2)c1=O]
11
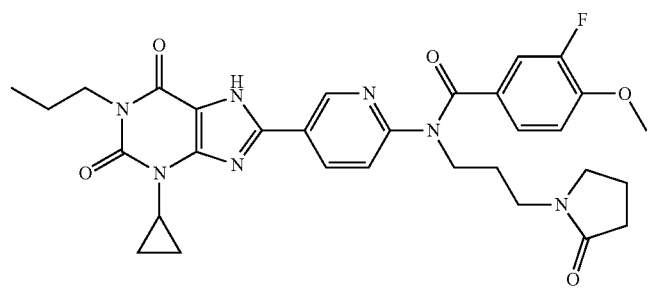 [SMILES: CCCn1c(=O)c2[nH]c(-c3ccc(N(CCCN4CCCC4=O)C(=O)c4ccc(OC)c(F)c4)nc3)nc2n(C2CC2)c1=O]
12
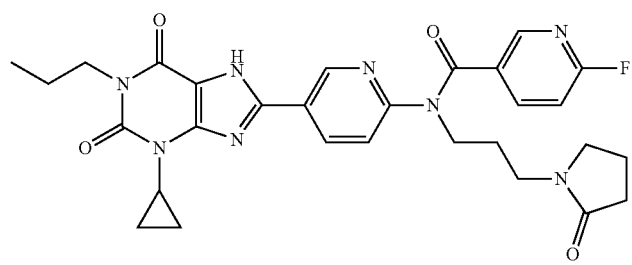 [SMILES: CCCn1c(=O)c2[nH]c(-c3ccc(N(CCCN4CCCC4=O)C(=O)c4ccc(F)nc4)nc3)nc2n(C2CC2)c1=O]
13
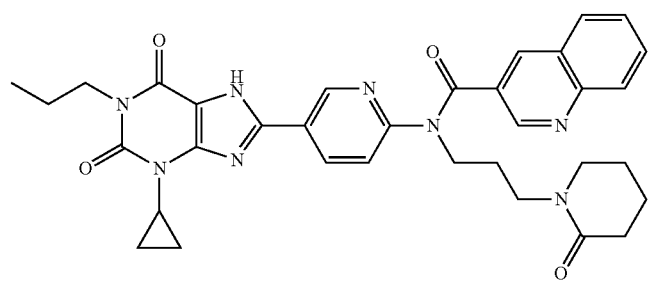 [SMILES: CCCn1c(=O)c2[nH]c(-c3ccc(N(CCCN4CCCCC4=O)C(=O)c4cnc5ccccc5c4)nc3)nc2n(C2CC2)c1=O]

TABLE 2-continued
14
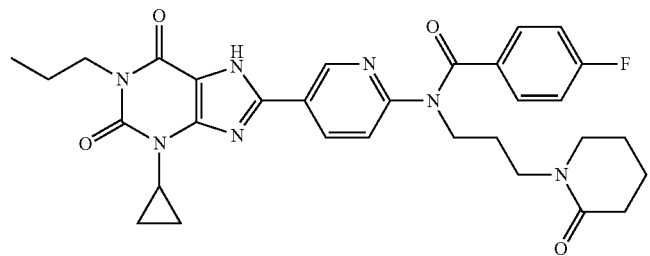 [SMILES: CCCn1c(=O)c2[nH]c(-c3ccc(N(CCCN4CCCCC4=O)C(=O)c4ccc(F)cc4)nc3)nc2n(C2CC2)c1=O]
15
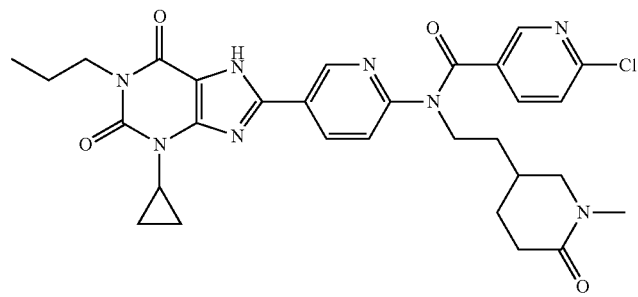 [SMILES: CCCn1c(=O)c2[nH]c(-c3ccc(N(CCC4CCC(=O)N(C)C4)C(=O)c4ccc(Cl)nc4)nc3)nc2n(C2CC2)c1=O]
16
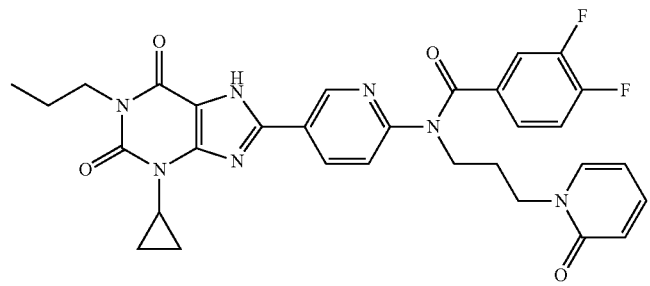 [SMILES: CCCn1c(=O)c2[nH]c(-c3ccc(N(CCCn4ccccc4=O)C(=O)c4ccc(F)c(F)c4)nc3)nc2n(C2CC2)c1=O]
17
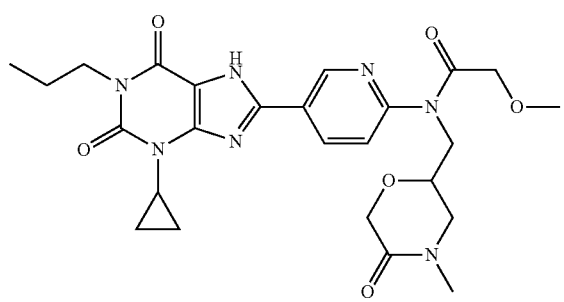 [SMILES: CCCn1c(=O)c2[nH]c(-c3ccc(N(CC4CN(C)C(=O)CO4)C(=O)COC)nc3)nc2n(C2CC2)c1=O]
18
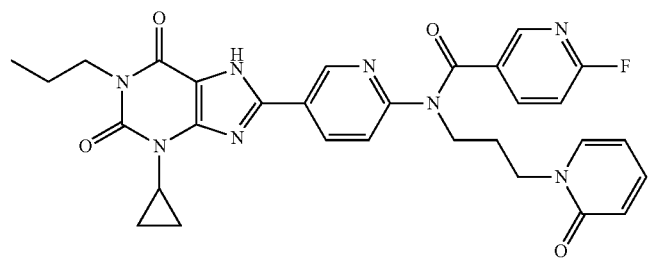 [SMILES: CCCn1c(=O)c2[nH]c(-c3ccc(N(CCCn4ccccc4=O)C(=O)c4ccc(F)nc4)nc3)nc2n(C2CC2)c1=O]

TABLE 2-continued
19 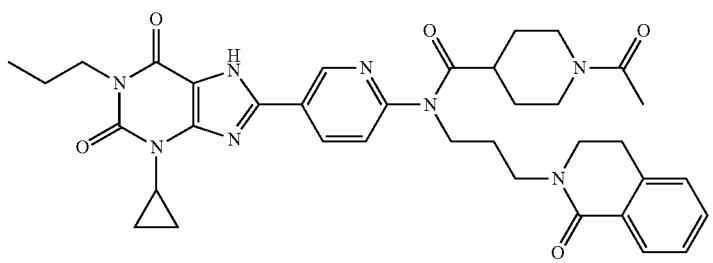 [SMILES: CCCn1c(=O)c2[nH]c(-c3ccc(N(CCCN4CCc5ccccc5C4=O)C(=O)C4CCN(C(C)=O)CC4)nc3)nc2n(C2CC2)c1=O]
20 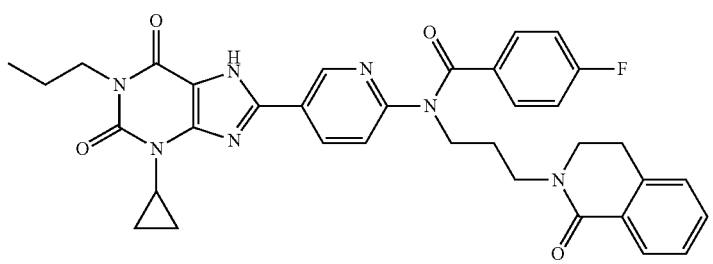 [SMILES: CCCn1c(=O)c2[nH]c(-c3ccc(N(CCCN4CCc5ccccc5C4=O)C(=O)c4ccc(F)cc4)nc3)nc2n(C2CC2)c1=O]
21 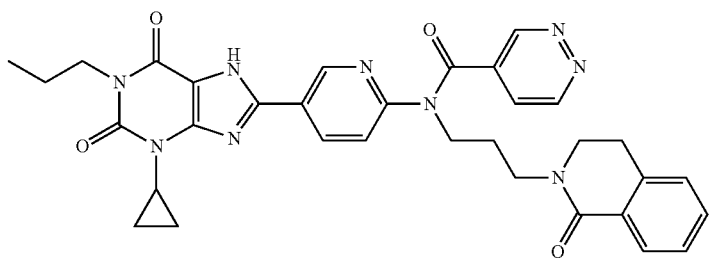 [SMILES: CCCn1c(=O)c2[nH]c(-c3ccc(N(CCCN4CCc5ccccc5C4=O)C(=O)c4ccnnc4)nc3)nc2n(C2CC2)c1=O]
22 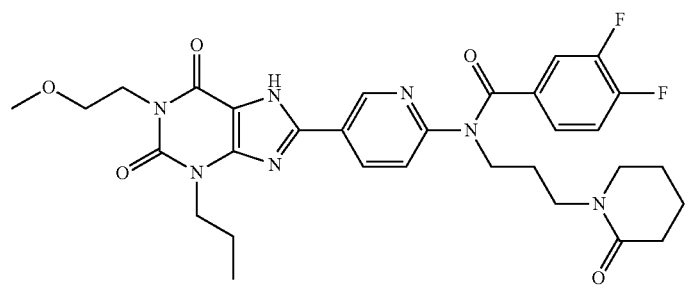 [SMILES: CCCn1c(=O)n(CCOC)c(=O)c2[nH]c(-c3ccc(N(CCCN4CCCCC4=O)C(=O)c4ccc(F)c(F)c4)nc3)nc21]
23 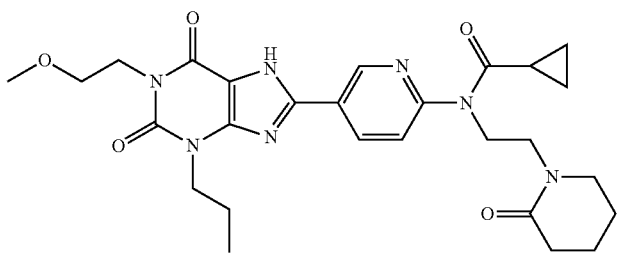 [SMILES: CCCn1c(=O)n(CCOC)c(=O)c2[nH]c(-c3ccc(N(CCN4CCCCC4=O)C(=O)C4CC4)nc3)nc21]
24 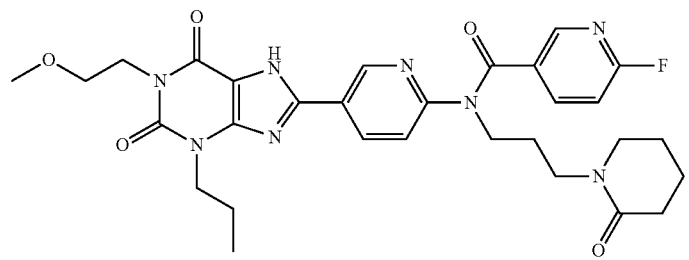

TABLE 2-continued
| 25 | 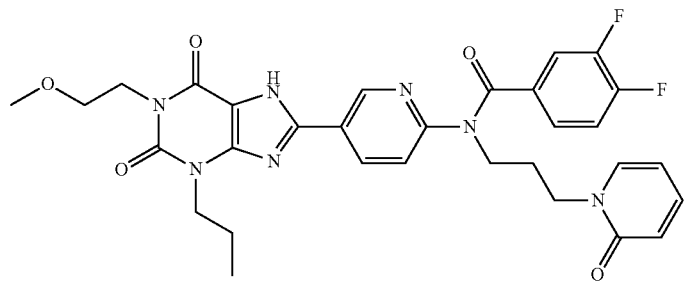 [SMILES: CCCn1c(=O)n(CCOC)c(=O)c2[nH]c(-c3ccc(N(CCCn4ccccc4=O)C(=O)c4ccc(F)c(F)c4)nc3)nc21] |
| 26 | 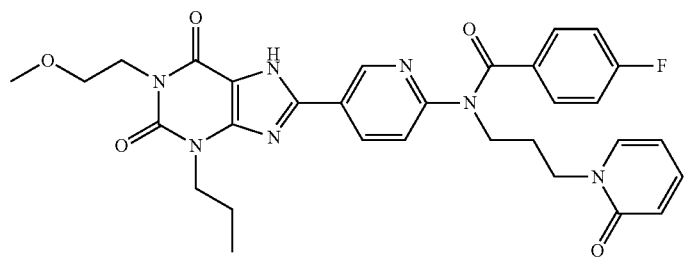 |
| 27 | 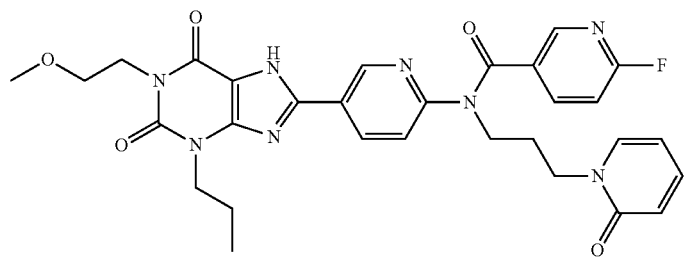 |
| 28 | 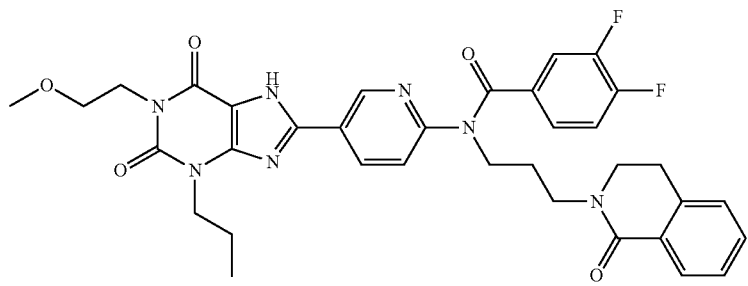 [SMILES: CCCn1c(=O)n(CCOC)c(=O)c2[nH]c(-c3ccc(N(CCCN4CCc5ccccc5C4=O)C(=O)c4ccc(F)c(F)c4)nc3)nc21] |
| 29 | 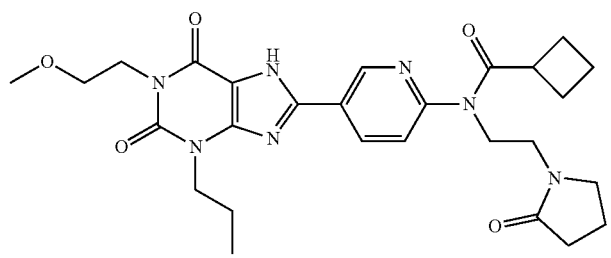 [SMILES: CCCn1c(=O)n(CCOC)c(=O)c2[nH]c(-c3ccc(N(CCN4CCCC4=O)C(=O)C4CCC4)nc3)nc21] |
| 30 | 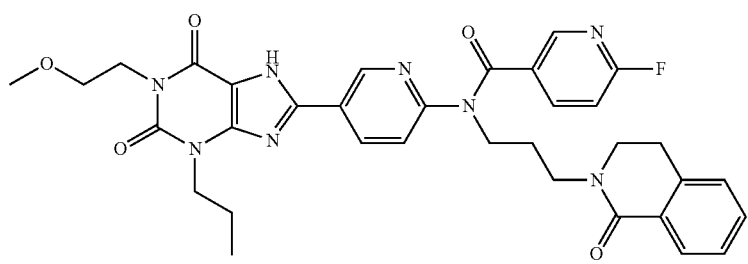 [SMILES: CCCn1c(=O)n(CCOC)c(=O)c2[nH]c(-c3ccc(N(CCCN4CCc5ccccc5C4=O)C(=O)c4ccc(F)nc4)nc3)nc21] |

TABLE 2-continued
31
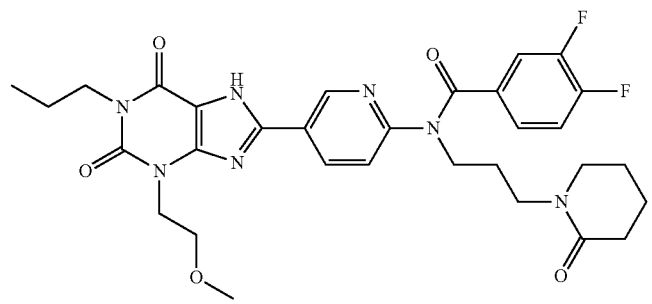 [SMILES: CCCn1c(=O)c2[nH]c(-c3ccc(N(CCCN4CCCCC4=O)C(=O)c4ccc(F)c(F)c4)nc3)nc2n(CCOC)c1=O]
32
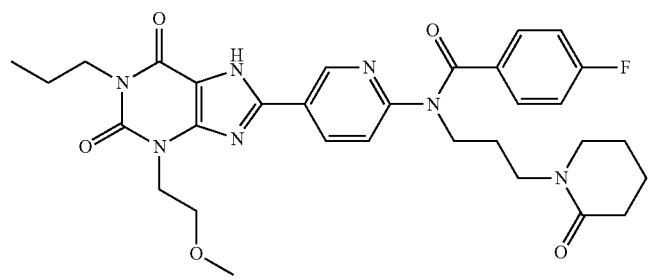 [SMILES: CCCn1c(=O)c2[nH]c(-c3ccc(N(CCCN4CCCCC4=O)C(=O)c4ccc(F)cc4)nc3)nc2n(CCOC)c1=O]
33
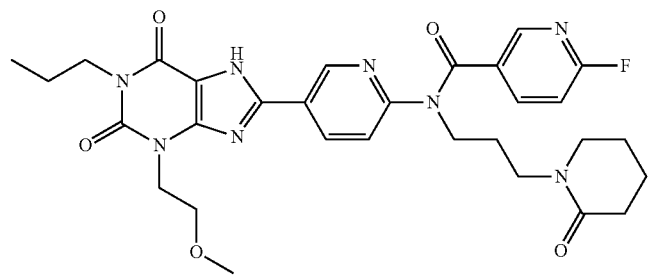
34
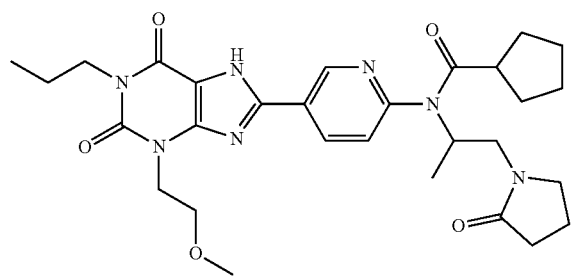 [SMILES: CCCn1c(=O)c2[nH]c(-c3ccc(N(C(=O)C4CCCC4)C(C)CN4CCCC4=O)nc3)nc2n(CCOC)c1=O]
35
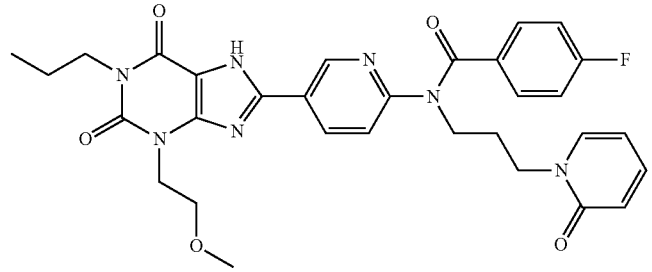

TABLE 2-continued
36
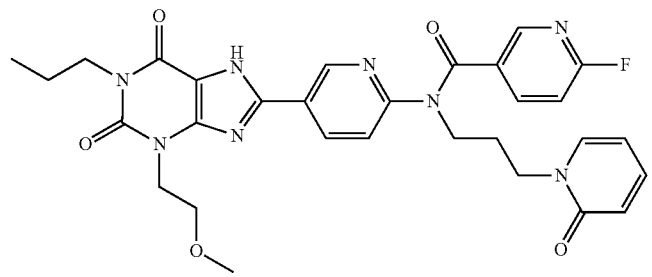
37
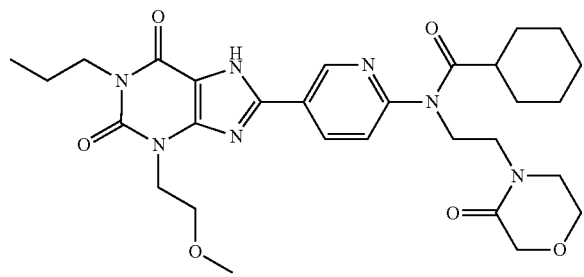 [SMILES: CCCn1c(=O)c2[nH]c(-c3ccc(N(CCN4CCOCC4=O)C(=O)C4CCCCC4)nc3)nc2n(CCOC)c1=O]
38
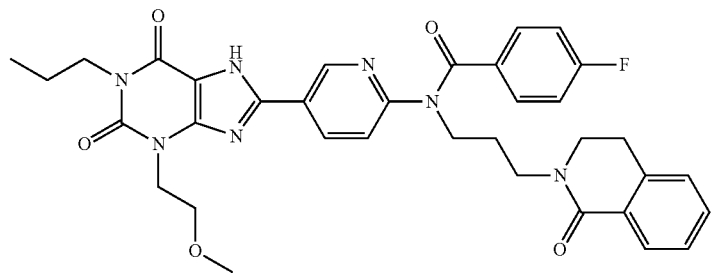
39
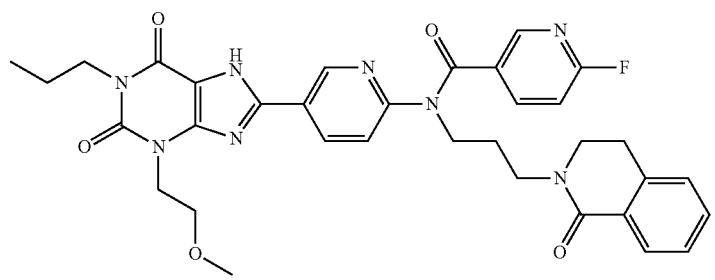
40
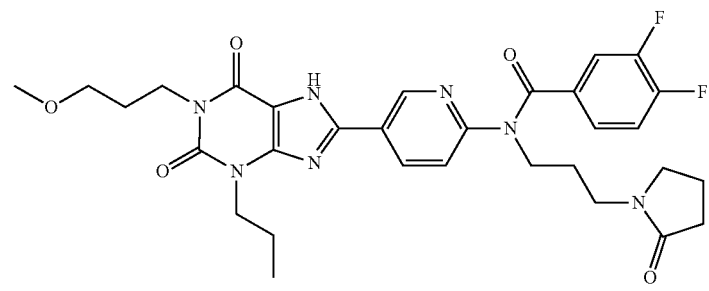 [SMILES: CCCn1c(=O)n(CCCOC)c(=O)c2[nH]c(-c3ccc(N(CCCN4CCCC4=O)C(=O)c4ccc(F)c(F)c4)nc3)nc21]

TABLE 2-continued
41 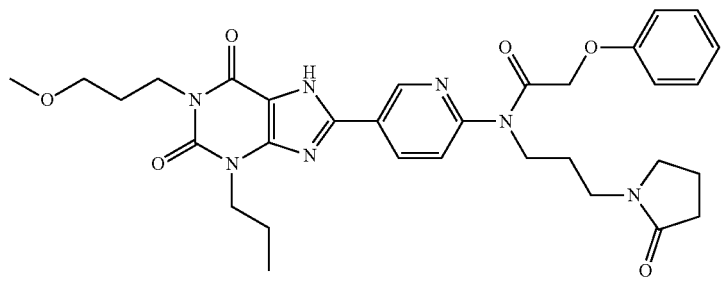 [SMILES: CCCn1c(=O)n(CCCOC)c(=O)c2[nH]c(-c3ccc(N(CCCN4CCCC4=O)C(=O)COc4ccccc4)nc3)nc21]
42 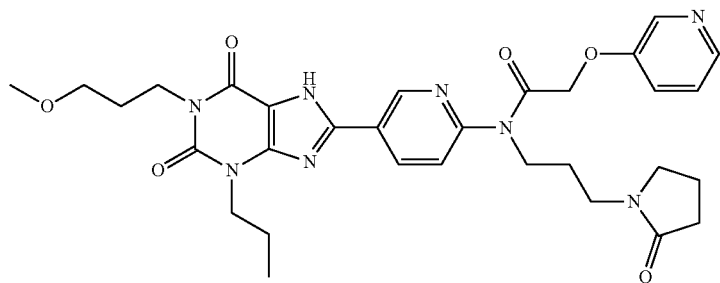 [SMILES: CCCn1c(=O)n(CCCOC)c(=O)c2[nH]c(-c3ccc(N(CCCN4CCCC4=O)C(=O)COc4cccnc4)nc3)nc21]
43 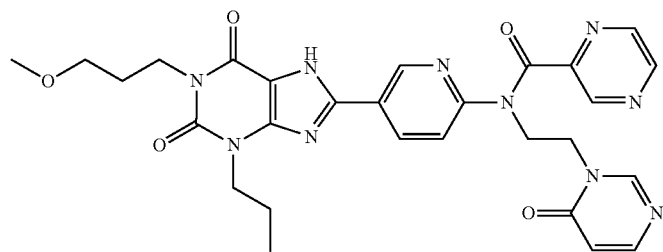 [SMILES: CCCn1c(=O)n(CCCOC)c(=O)c2[nH]c(-c3ccc(N(CCn4cnccc4=O)C(=O)c4cnccn4)nc3)nc21]
44 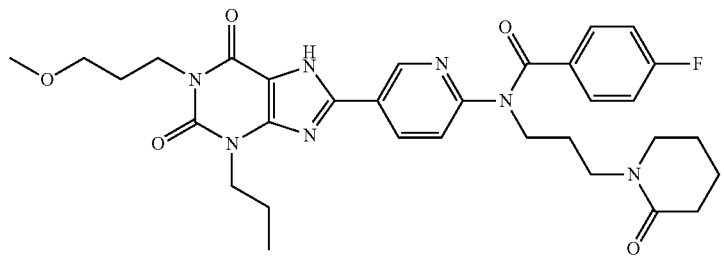 [SMILES: CCCn1c(=O)n(CCCOC)c(=O)c2[nH]c(-c3ccc(N(CCCN4CCCCC4=O)C(=O)c4ccc(F)cc4)nc3)nc21]
45 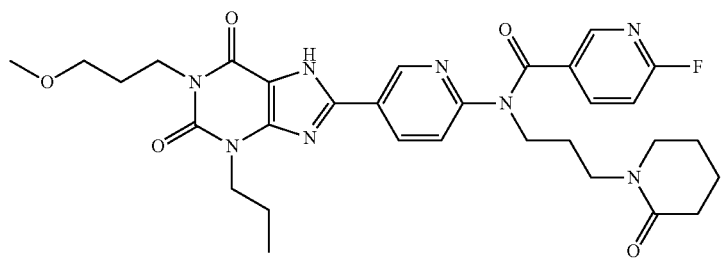
46 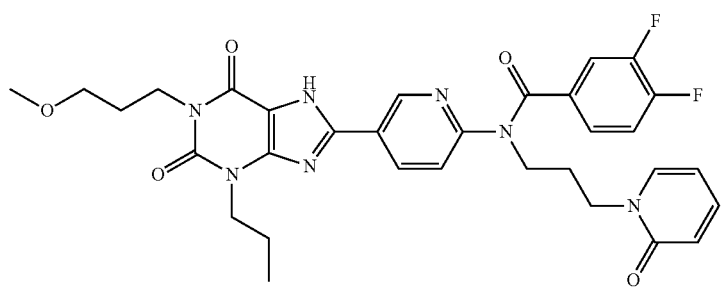 [SMILES: CCCn1c(=O)n(CCCOC)c(=O)c2[nH]c(-c3ccc(N(CCCn4ccccc4=O)C(=O)c4ccc(F)c(F)c4)nc3)nc21]

TABLE 2-continued
47
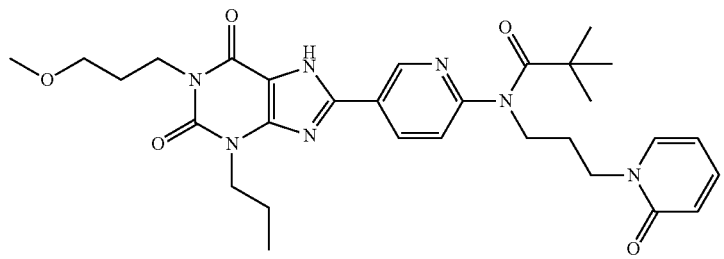 [SMILES: CCCn1c(=O)n(CCCOC)c(=O)c2[nH]c(-c3ccc(N(CCCn4ccccc4=O)C(=O)C(C)(C)C)nc3)nc21]
48
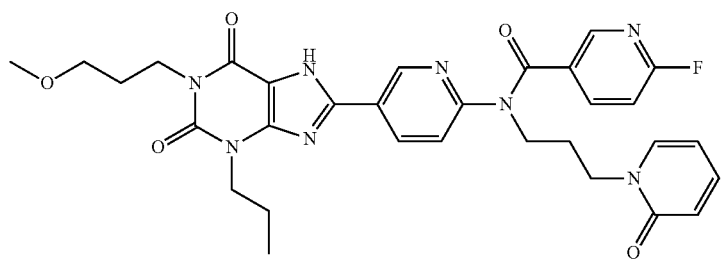 [SMILES: CCCn1c(=O)n(CCCOC)c(=O)c2[nH]c(-c3ccc(N(CCCn4ccccc4=O)C(=O)c4ccc(F)nc4)nc3)nc21]
49
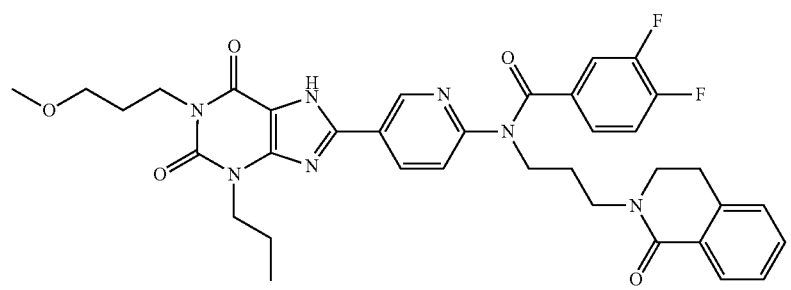 [SMILES: CCCn1c(=O)n(CCCOC)c(=O)c2[nH]c(-c3ccc(N(CCCN4CCc5ccccc5C4=O)C(=O)c4ccc(F)c(F)c4)nc3)nc21]
50
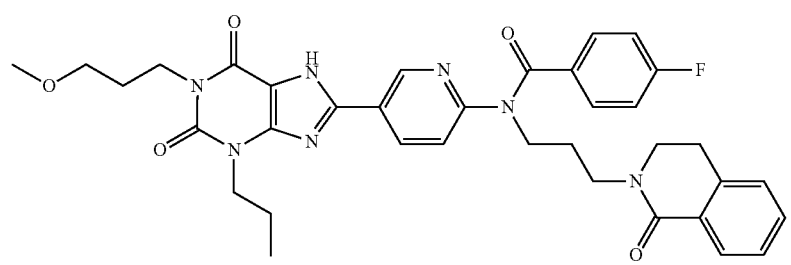 [SMILES: CCCn1c(=O)n(CCCOC)c(=O)c2[nH]c(-c3ccc(N(CCCN4CCc5ccccc5C4=O)C(=O)c4ccc(F)cc4)nc3)nc21]
51
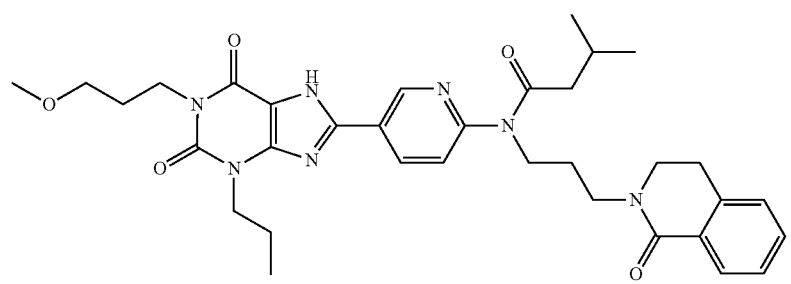 [SMILES: CCCn1c(=O)n(CCCOC)c(=O)c2[nH]c(-c3ccc(N(CCCN4CCc5ccccc5C4=O)C(=O)CC(C)C)nc3)nc21]

TABLE 2-continued
52 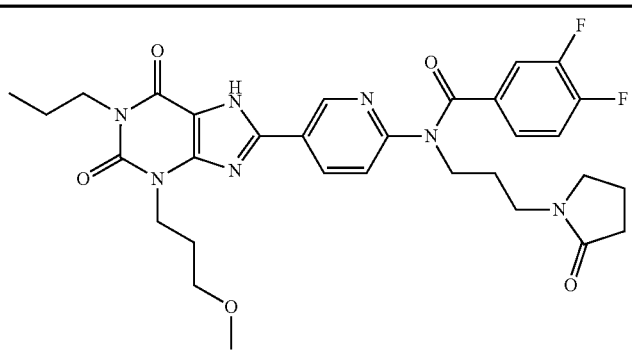
53 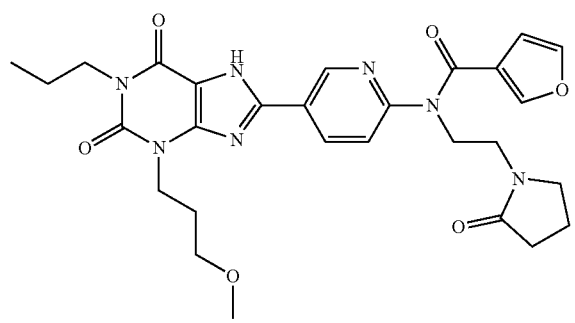 [SMILES: CCCn1c(=O)c2[nH]c(-c3ccc(N(CCN4CCCC4=O)C(=O)c4ccoc4)nc3)nc2n(CCCOC)c1=O]
54 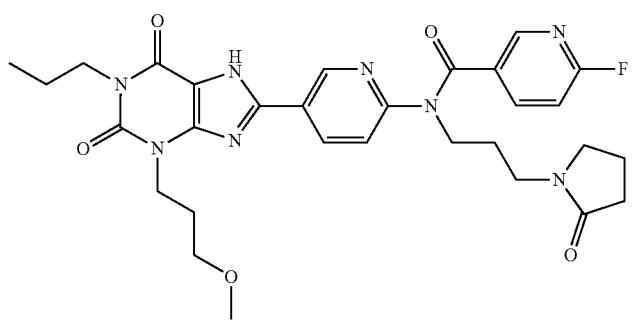 [SMILES: CCCn1c(=O)c2[nH]c(-c3ccc(N(CCCN4CCCC4=O)C(=O)c4ccc(F)nc4)nc3)nc2n(CCCOC)c1=O]
55 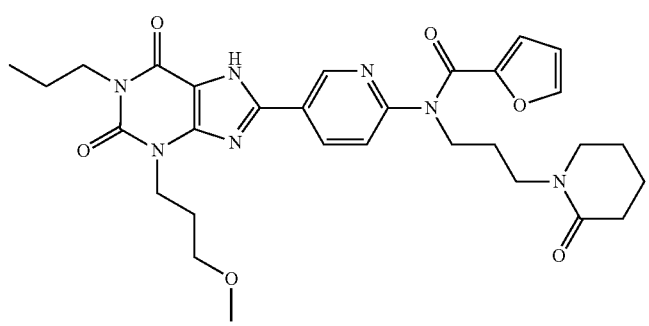 [SMILES: CCCn1c(=O)c2[nH]c(-c3ccc(N(CCCN4CCCCC4=O)C(=O)c4ccco4)nc3)nc2n(CCCOC)c1=O]
56 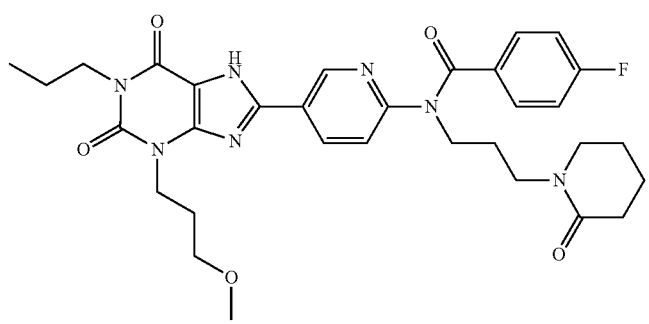

TABLE 2-continued
| 57 | 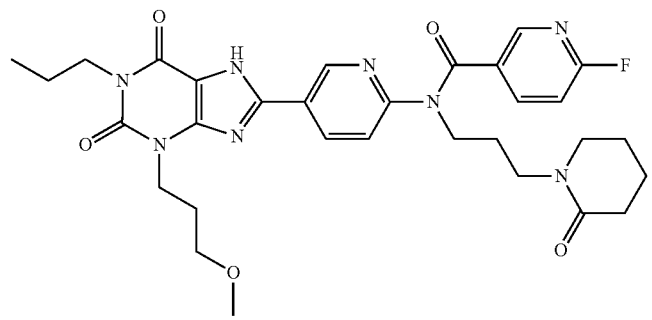 [SMILES: CCCn1c(=O)c2[nH]c(-c3ccc(N(CCCN4CCCCC4=O)C(=O)c4ccc(F)nc4)nc3)nc2n(CCCOC)c1=O] |
| 58 | 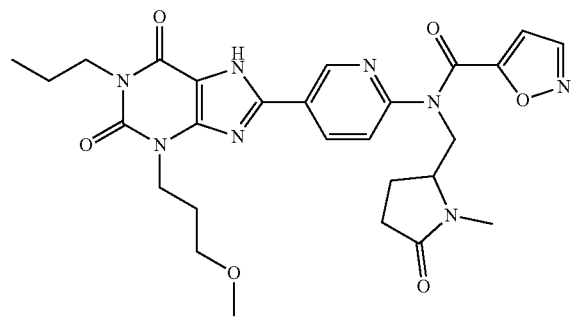 [SMILES: CCCn1c(=O)c2[nH]c(-c3ccc(N(CC4CCC(=O)N4C)C(=O)c4ccno4)nc3)nc2n(CCCOC)c1=O] |
| 59 | 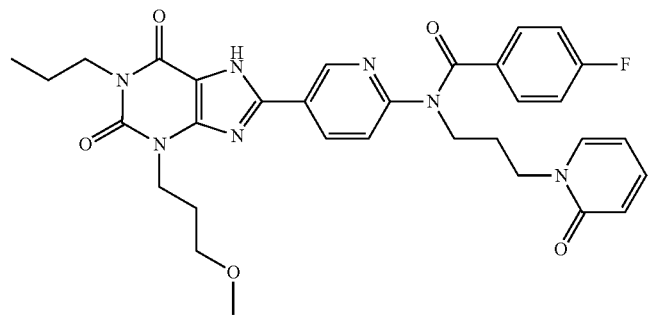 [SMILES: CCCn1c(=O)c2[nH]c(-c3ccc(N(CCCn4ccccc4=O)C(=O)c4ccc(F)cc4)nc3)nc2n(CCCOC)c1=O] |
| 60 | 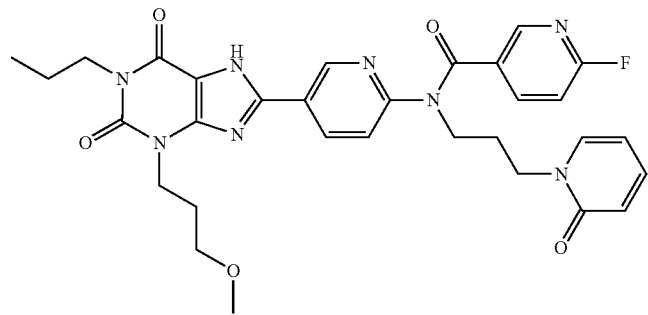 [SMILES: CCCn1c(=O)c2[nH]c(-c3ccc(N(CCCn4ccccc4=O)C(=O)c4ccc(F)nc4)nc3)nc2n(CCCOC)c1=O] |
| 61 | 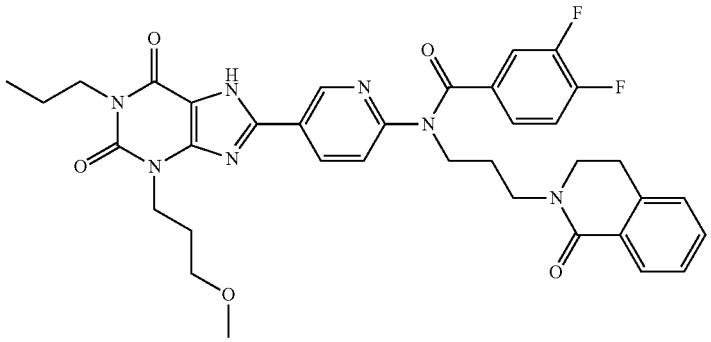 [SMILES: CCCn1c(=O)c2[nH]c(-c3ccc(N(CCCN4CCc5ccccc5C4=O)C(=O)c4ccc(F)c(F)c4)nc3)nc2n(CCCOC)c1=O] |

TABLE 2-continued
62
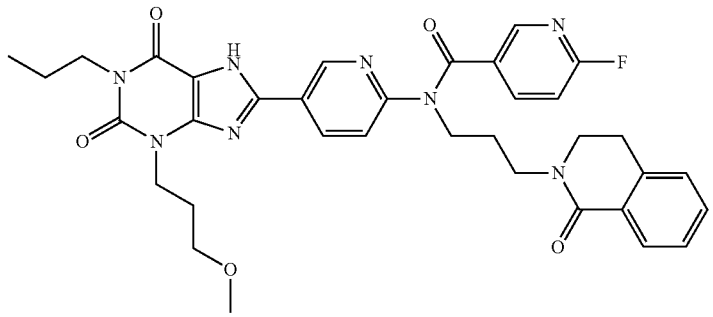 [SMILES: CCCn1c(=O)c2[nH]c(-c3ccc(N(CCCN4CCc5ccccc5C4=O)C(=O)c4ccc(F)nc4)nc3)nc2n(CCCOC)c1=O]
63
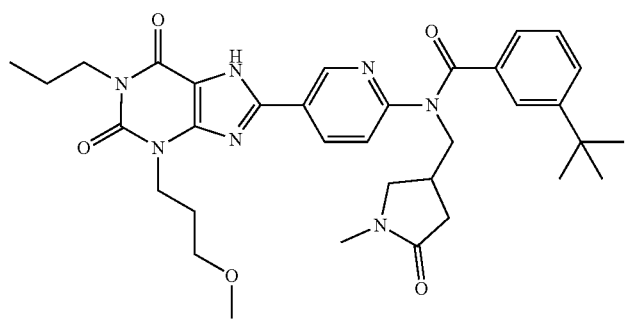 [SMILES: CCCn1c(=O)c2[nH]c(-c3ccc(N(CC4CC(=O)N(C)C4)C(=O)c4cccc(C(C)(C)C)c4)nc3)nc2n(CCCOC)c1=O]
64
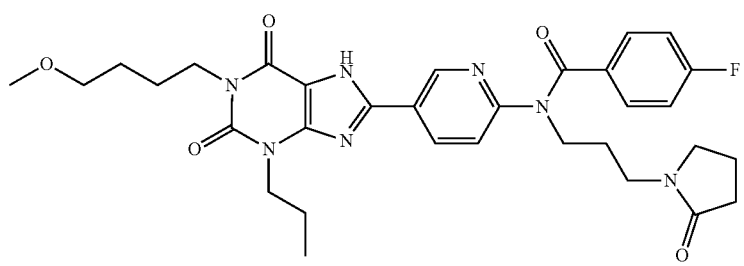 [SMILES: CCCn1c(=O)n(CCCCOC)c(=O)c2[nH]c(-c3ccc(N(CCCN4CCCC4=O)C(=O)c4ccc(F)cc4)nc3)nc21]
65
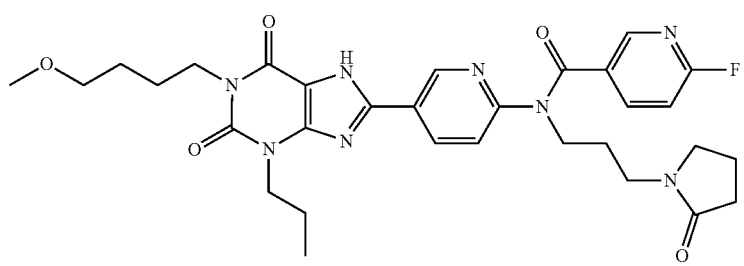 [SMILES: CCCn1c(=O)n(CCCCOC)c(=O)c2[nH]c(-c3ccc(N(CCCN4CCCC4=O)C(=O)c4ccc(F)nc4)nc3)nc21]
66
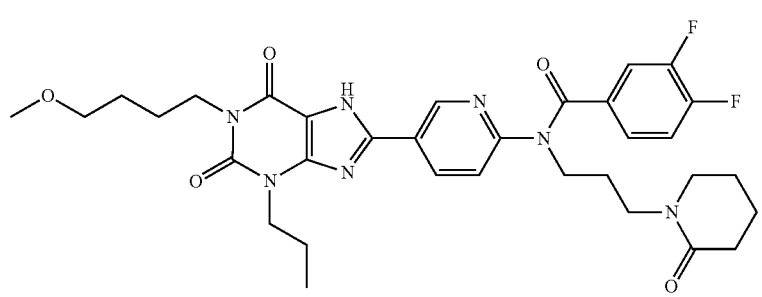 [SMILES: CCCn1c(=O)n(CCCCOC)c(=O)c2[nH]c(-c3ccc(N(CCCN4CCCCC4=O)C(=O)c4ccc(F)c(F)c4)nc3)nc21]

TABLE 2-continued
67
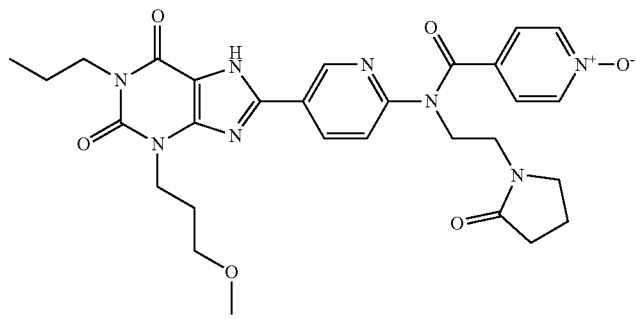 [SMILES: CCCn1c(=O)c2[nH]c(-c3ccc(N(CCN4CCCC4=O)C(=O)c4cc[n+]([O-])cc4)nc3)nc2n(CCCOC)c1=O]
68
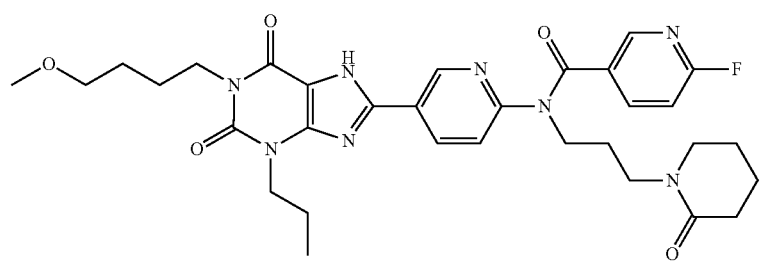
69
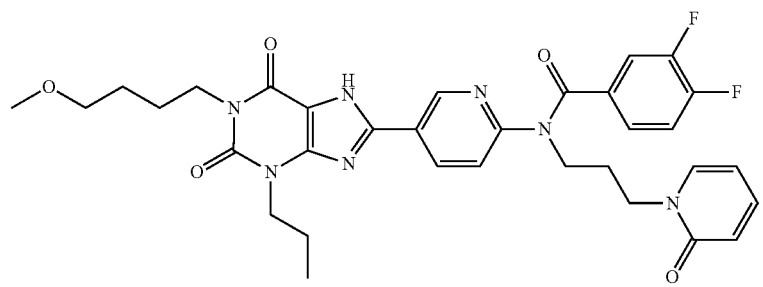
70
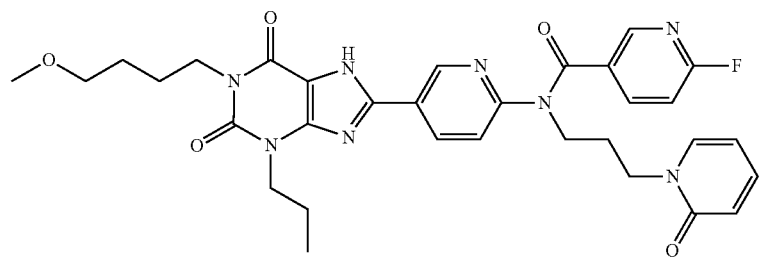
71
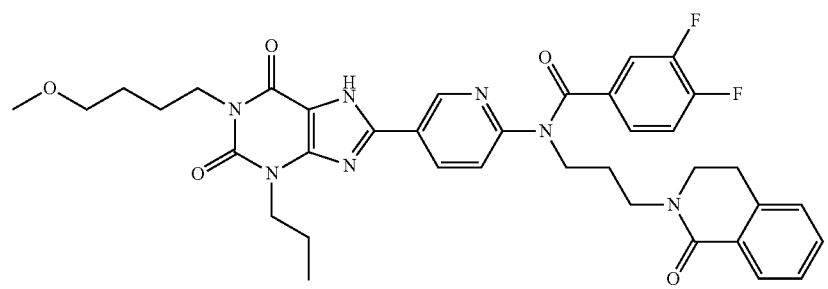 [SMILES: CCCn1c(=O)n(CCCCOC)c(=O)c2[nH]c(-c3ccc(N(CCCN4CCc5ccccc5C4=O)C(=O)c4ccc(F)c(F)c4)nc3)nc21]

TABLE 2-continued
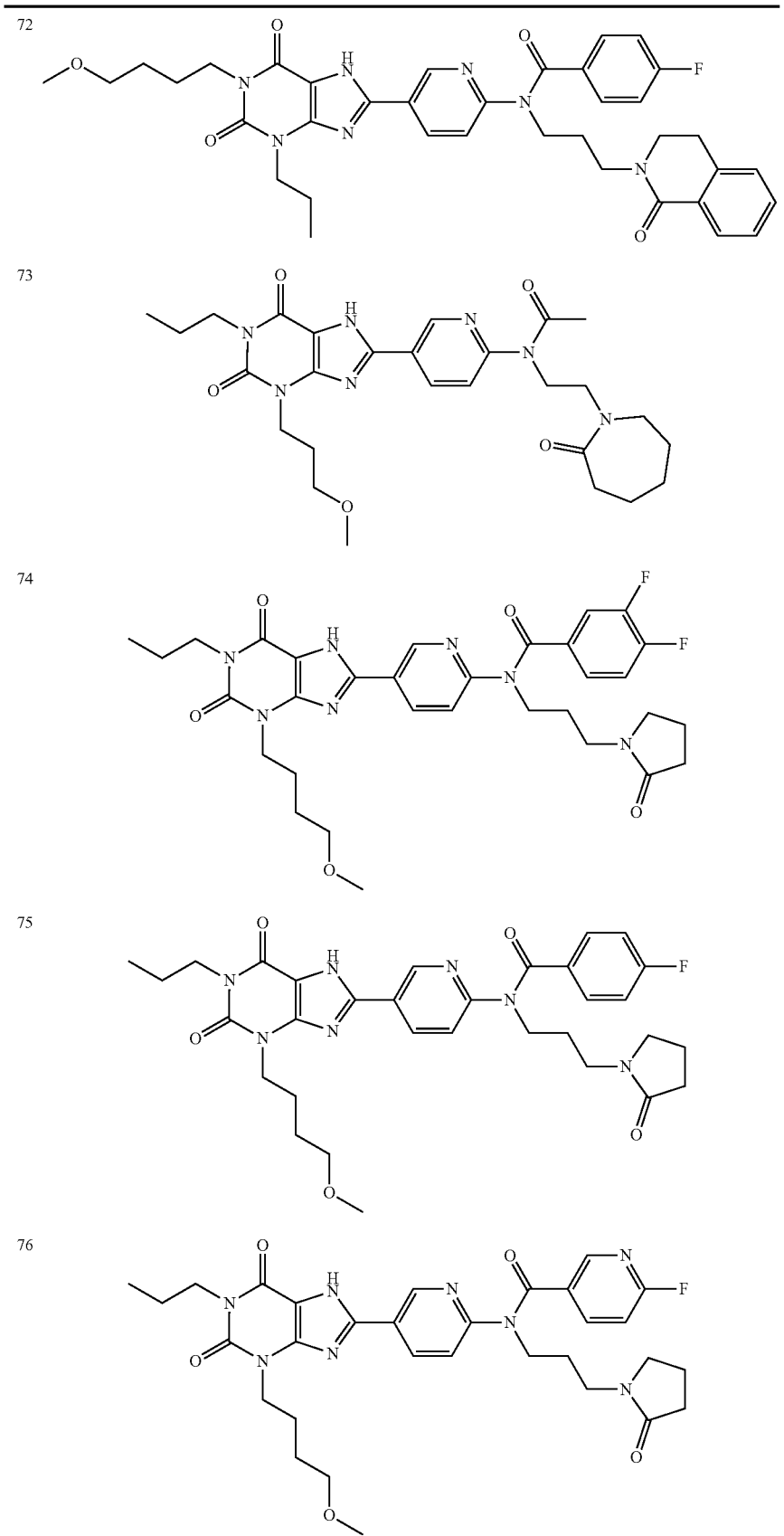

TABLE 2-continued
77
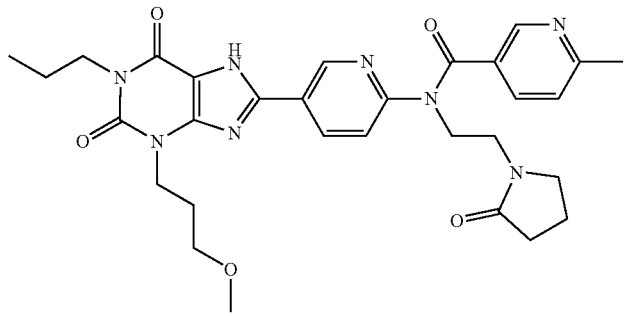 [SMILES: CCCn1c(=O)c2[nH]c(-c3ccc(N(CCN4CCCC4=O)C(=O)c4ccc(C)nc4)nc3)nc2n(CCCOC)c1=O]
78
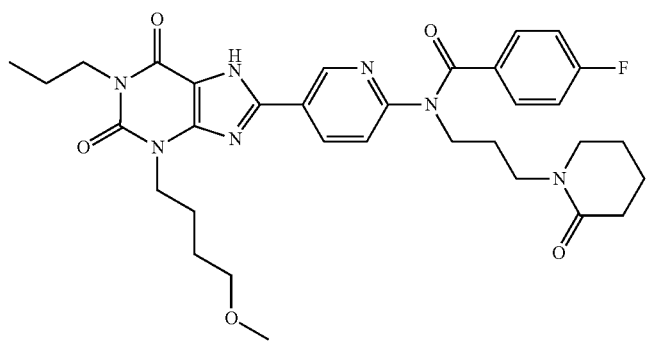 [SMILES: CCCn1c(=O)c2[nH]c(-c3ccc(N(CCCN4CCCCC4=O)C(=O)c4ccc(F)cc4)nc3)nc2n(CCCCOC)c1=O]
79
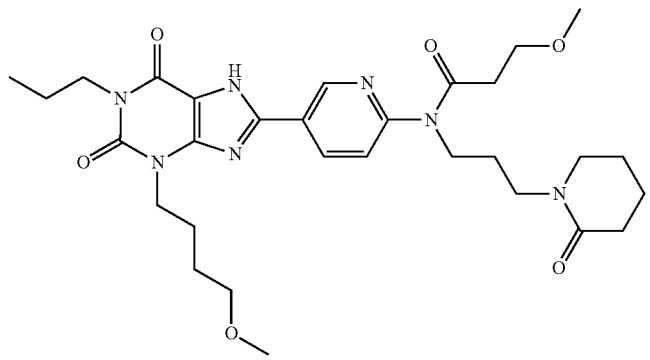 [SMILES: CCCn1c(=O)c2[nH]c(-c3ccc(N(CCCN4CCCCC4=O)C(=O)CCOC)nc3)nc2n(CCCCOC)c1=O]
80
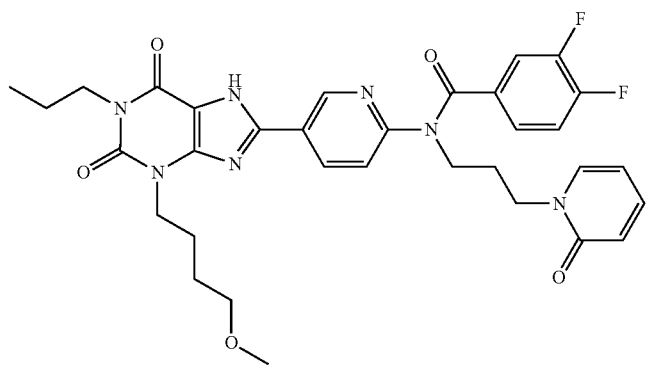 [SMILES: CCCn1c(=O)c2[nH]c(-c3ccc(N(CCCn4ccccc4=O)C(=O)c4ccc(F)c(F)c4)nc3)nc2n(CCCCOC)c1=O]

TABLE 2-continued
81 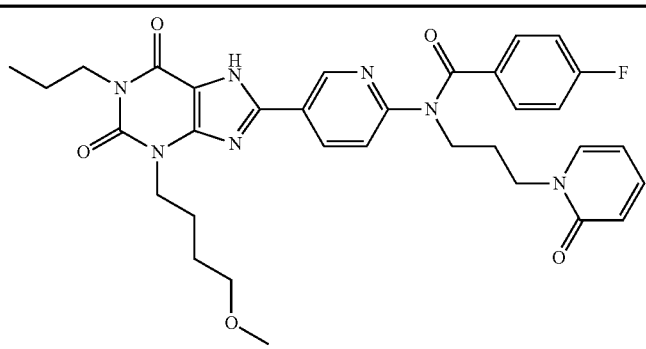
82 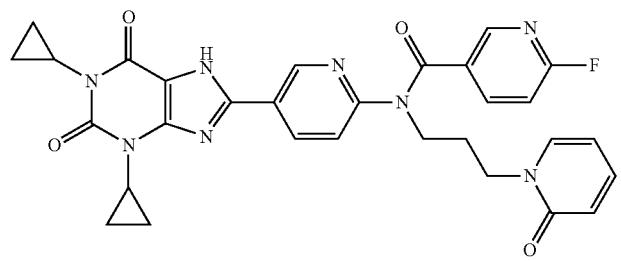 [SMILES: O=C(c1ccc(F)nc1)N(CCCn1ccccc1=O)c1ccc(-c2nc3c([nH]2)c(=O)n(C2CC2)c(=O)n3C2CC2)cn1]
83 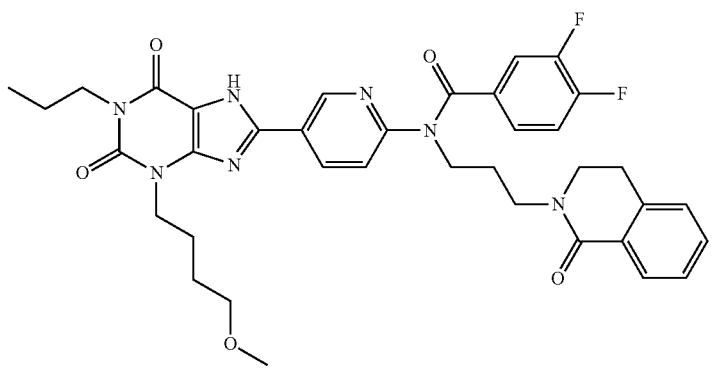 [SMILES: CCCn1c(=O)c2[nH]c(-c3ccc(N(CCCN4CCc5ccccc5C4=O)C(=O)c4ccc(F)c(F)c4)nc3)nc2n(CCCCOC)c1=O]
84 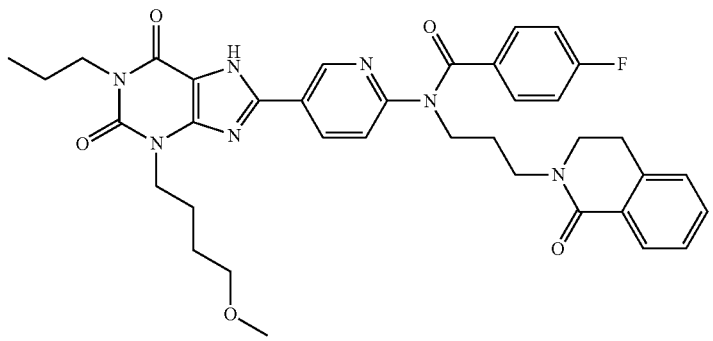 [SMILES: CCCn1c(=O)c2[nH]c(-c3ccc(N(CCCN4CCc5ccccc5C4=O)C(=O)c4ccc(F)cc4)nc3)nc2n(CCCCOC)c1=O]
85 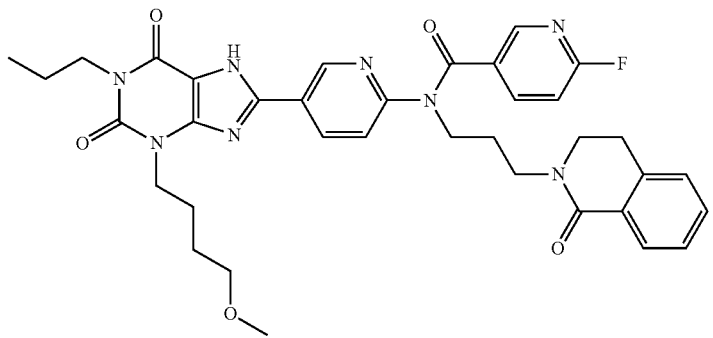 [SMILES: CCCn1c(=O)c2[nH]c(-c3ccc(N(CCCN4CCc5ccccc5C4=O)C(=O)c4ccc(F)nc4)nc3)nc2n(CCCCOC)c1=O]

TABLE 2-continued
86
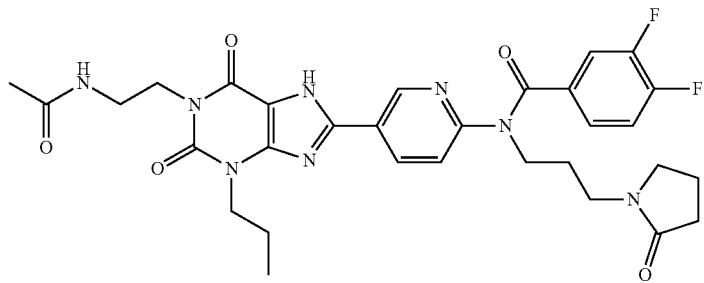 [SMILES: CCCn1c(=O)n(CCNC(C)=O)c(=O)c2[nH]c(-c3ccc(N(CCCN4CCCC4=O)C(=O)c4ccc(F)c(F)c4)nc3)nc21]
87
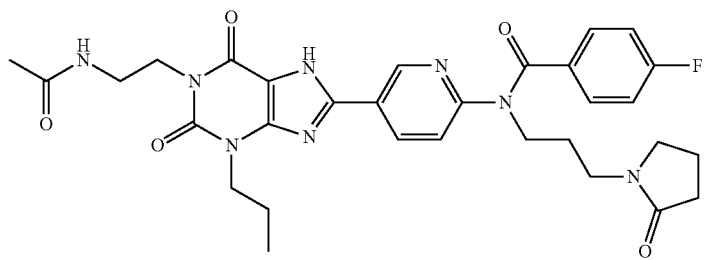 [SMILES: CCCn1c(=O)n(CCNC(C)=O)c(=O)c2[nH]c(-c3ccc(N(CCCN4CCCC4=O)C(=O)c4ccc(F)cc4)nc3)nc21]
88
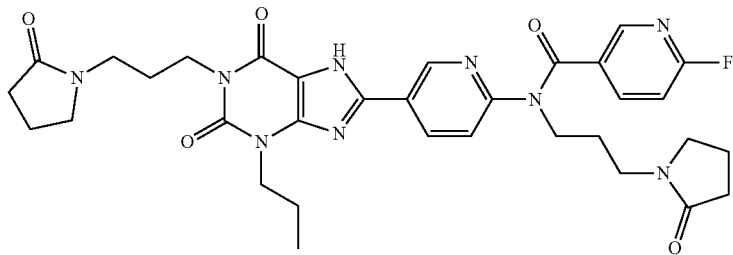 [SMILES: CCCn1c(=O)n(CCCN2CCCC2=O)c(=O)c2[nH]c(-c3ccc(N(CCCN4CCCC4=O)C(=O)c4ccc(F)nc4)nc3)nc21]
89
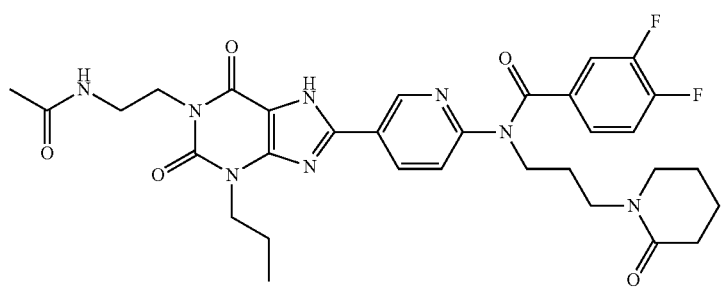
90
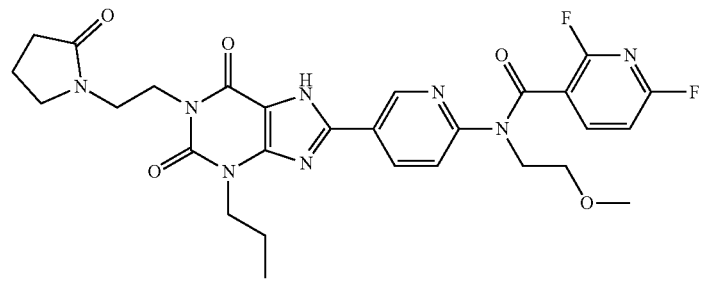 [SMILES: CCCn1c(=O)n(CCN2CCCC2=O)c(=O)c2[nH]c(-c3ccc(N(CCOC)C(=O)c4ccc(F)nc4F)nc3)nc21]

TABLE 2-continued
91
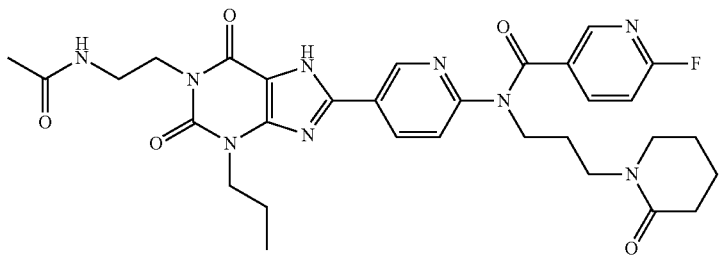 [SMILES: CCCn1c(=O)n(CCNC(C)=O)c(=O)c2[nH]c(-c3ccc(N(CCCN4CCCCC4=O)C(=O)c4ccc(F)nc4)nc3)nc21]
92
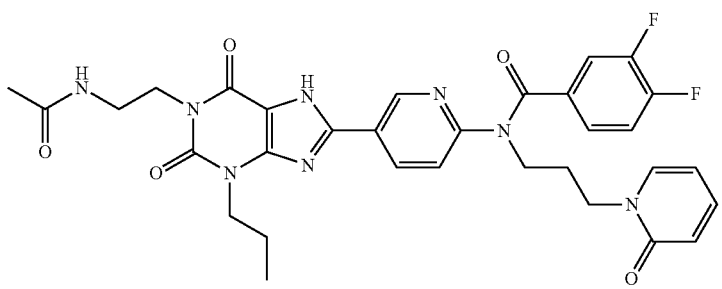 [SMILES: CCCn1c(=O)n(CCNC(C)=O)c(=O)c2[nH]c(-c3ccc(N(CCCn4ccccc4=O)C(=O)c4ccc(F)c(F)c4)nc3)nc21]
93
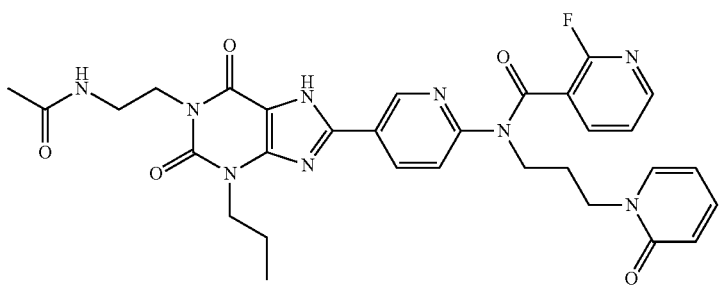 [SMILES: CCCn1c(=O)n(CCNC(C)=O)c(=O)c2[nH]c(-c3ccc(N(CCCn4ccccc4=O)C(=O)c4cccnc4F)nc3)nc21]
94
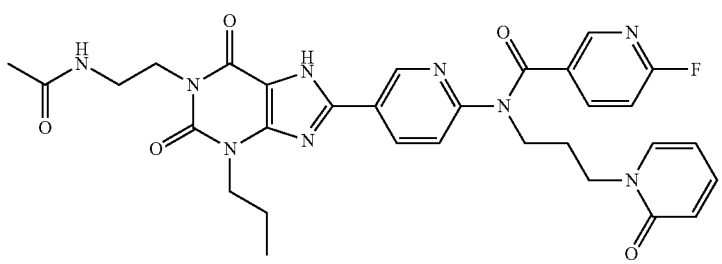 [SMILES: CCCn1c(=O)n(CCNC(C)=O)c(=O)c2[nH]c(-c3ccc(N(CCCn4ccccc4=O)C(=O)c4ccc(F)nc4)nc3)nc21]
95
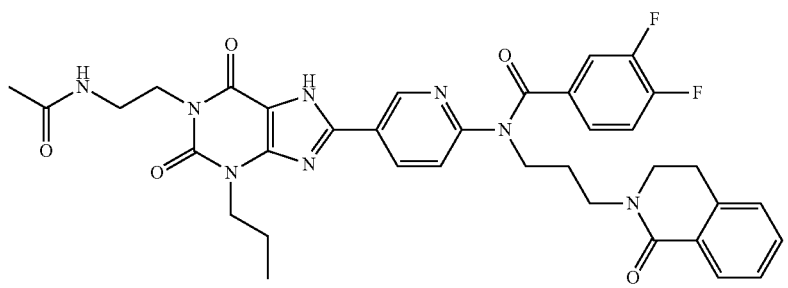 [SMILES: CCCn1c(=O)n(CCNC(C)=O)c(=O)c2[nH]c(-c3ccc(N(CCCN4CCc5ccccc5C4=O)C(=O)c4ccc(F)c(F)c4)nc3)nc21]

TABLE 2-continued
96 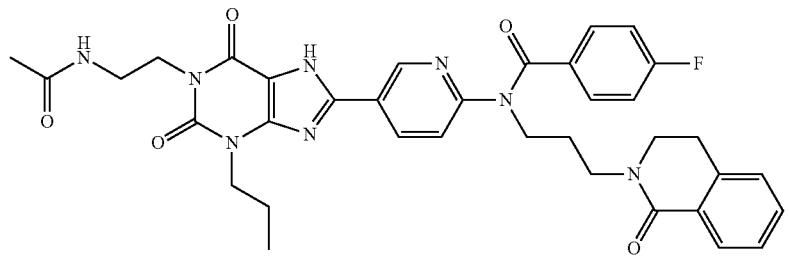 [SMILES: CCCn1c(=O)n(CCNC(C)=O)c(=O)c2[nH]c(-c3ccc(N(CCCN4CCc5ccccc5C4=O)C(=O)c4ccc(F)cc4)nc3)nc21]
97 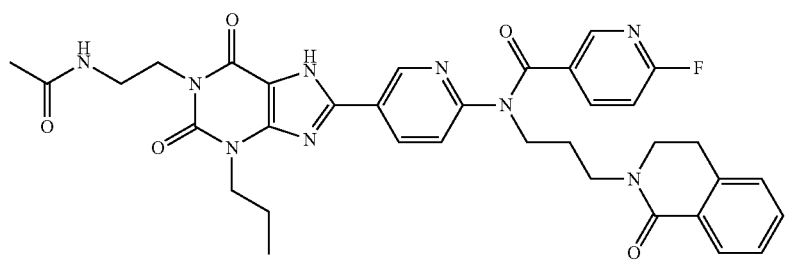 [SMILES: CCCn1c(=O)n(CCNC(C)=O)c(=O)c2[nH]c(-c3ccc(N(CCCN4CCc5ccccc5C4=O)C(=O)c4ccc(F)nc4)nc3)nc21]
98 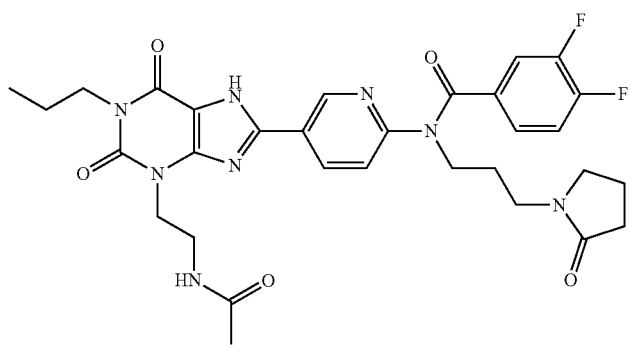 [SMILES: CCCn1c(=O)c2[nH]c(-c3ccc(N(CCCN4CCCC4=O)C(=O)c4ccc(F)c(F)c4)nc3)nc2n(CCNC(C)=O)c1=O]
99 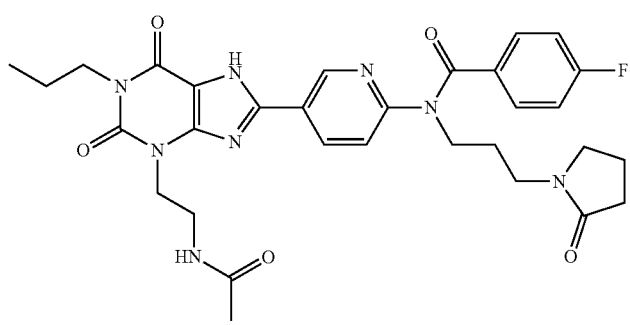
100 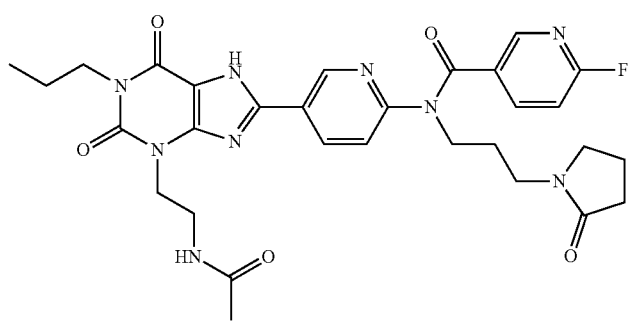

TABLE 2-continued
101 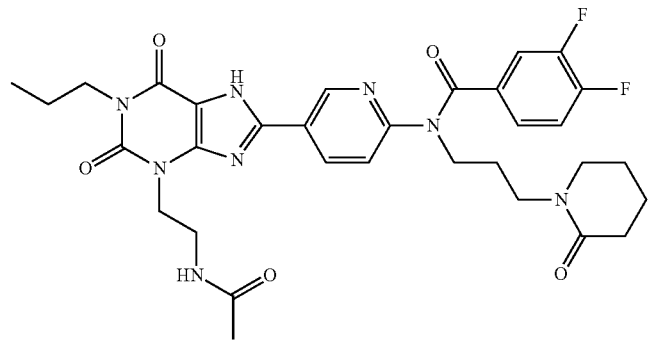 [SMILES: CCCn1c(=O)c2[nH]c(-c3ccc(N(CCCN4CCCCC4=O)C(=O)c4ccc(F)c(F)c4)nc3)nc2n(CCNC(C)=O)c1=O]
102 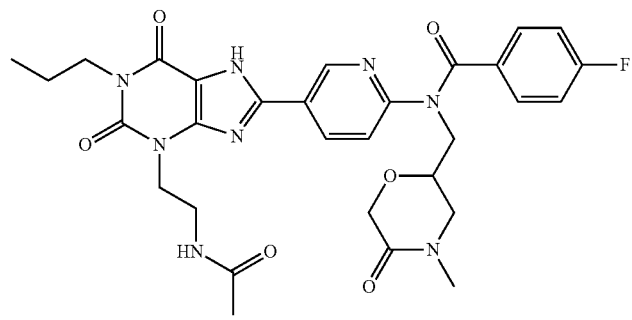 [SMILES: CCCn1c(=O)c2[nH]c(-c3ccc(N(CC4CN(C)C(=O)CO4)C(=O)c4ccc(F)cc4)nc3)nc2n(CCNC(C)=O)c1=O]
103 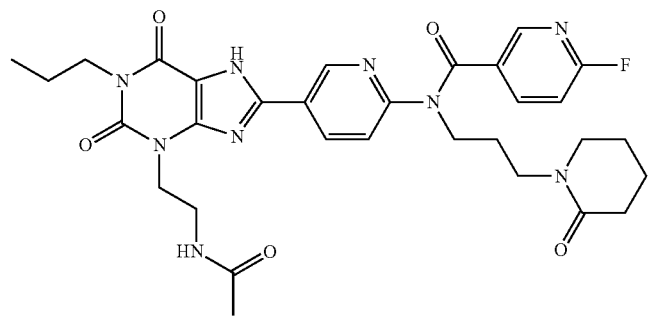 [SMILES: CCCn1c(=O)c2[nH]c(-c3ccc(N(CCCN4CCCCC4=O)C(=O)c4ccc(F)nc4)nc3)nc2n(CCNC(C)=O)c1=O]
104 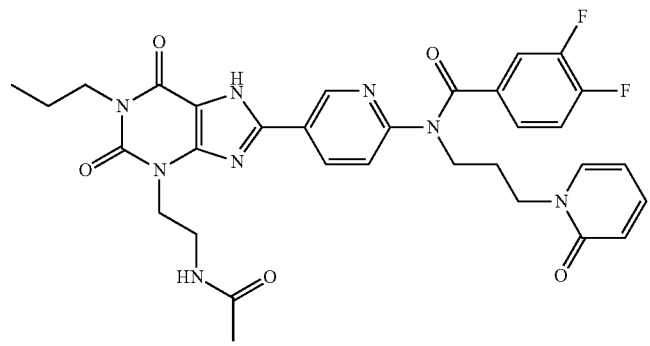 [SMILES: CCCn1c(=O)c2[nH]c(-c3ccc(N(CCCn4ccccc4=O)C(=O)c4ccc(F)c(F)c4)nc3)nc2n(CCNC(C)=O)c1=O]
105 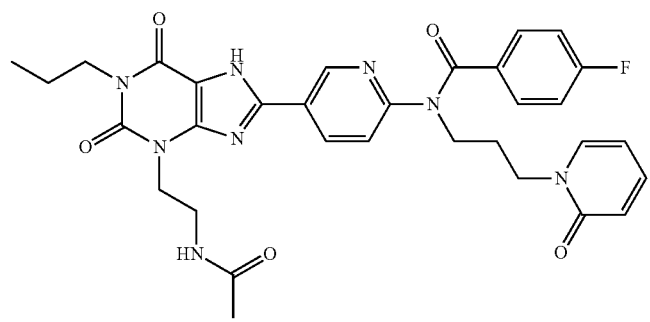 [SMILES: CCCn1c(=O)c2[nH]c(-c3ccc(N(CCCn4ccccc4=O)C(=O)c4ccc(F)cc4)nc3)nc2n(CCNC(C)=O)c1=O]

TABLE 2-continued
106 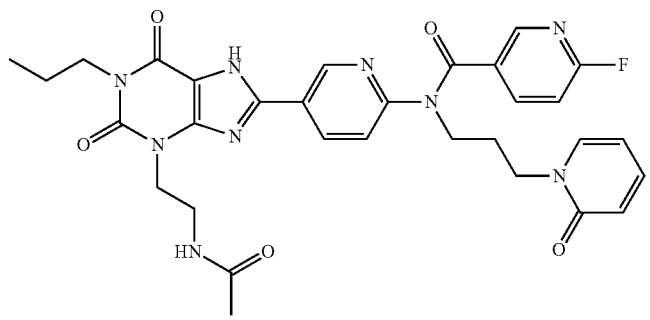
107 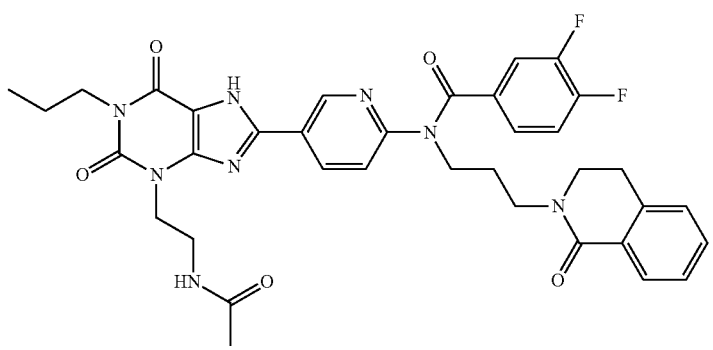 [SMILES: CCCn1c(=O)c2[nH]c(-c3ccc(N(CCCN4CCc5ccccc5C4=O)C(=O)c4ccc(F)c(F)c4)nc3)nc2n(CCNC(C)=O)c1=O]
108 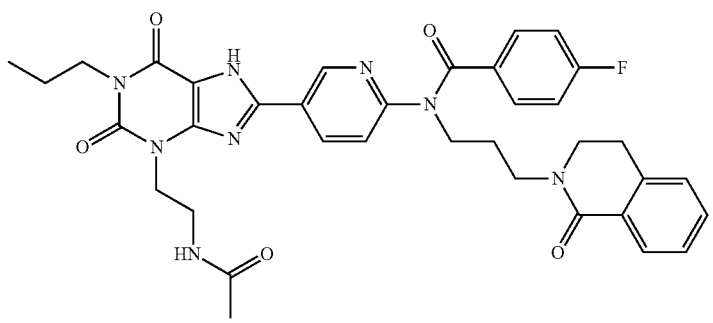 [SMILES: CCCn1c(=O)c2[nH]c(-c3ccc(N(CCCN4CCc5ccccc5C4=O)C(=O)c4ccc(F)cc4)nc3)nc2n(CCNC(C)=O)c1=O]
109 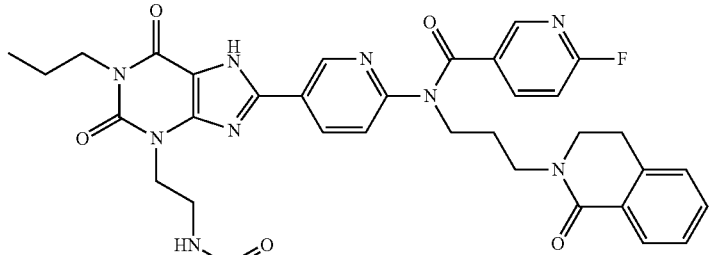
110 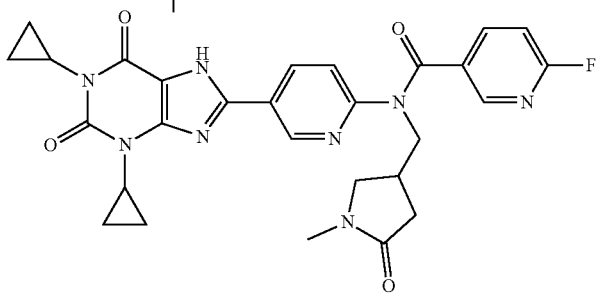
or a stereoisomer or pharmaceutically acceptable salt thereof.

12. A compound of claim 1, wherein the compound is selected from the compounds of Table 3 or a stereoisomer or pharmaceutically acceptable salt thereof;
TABLE 3
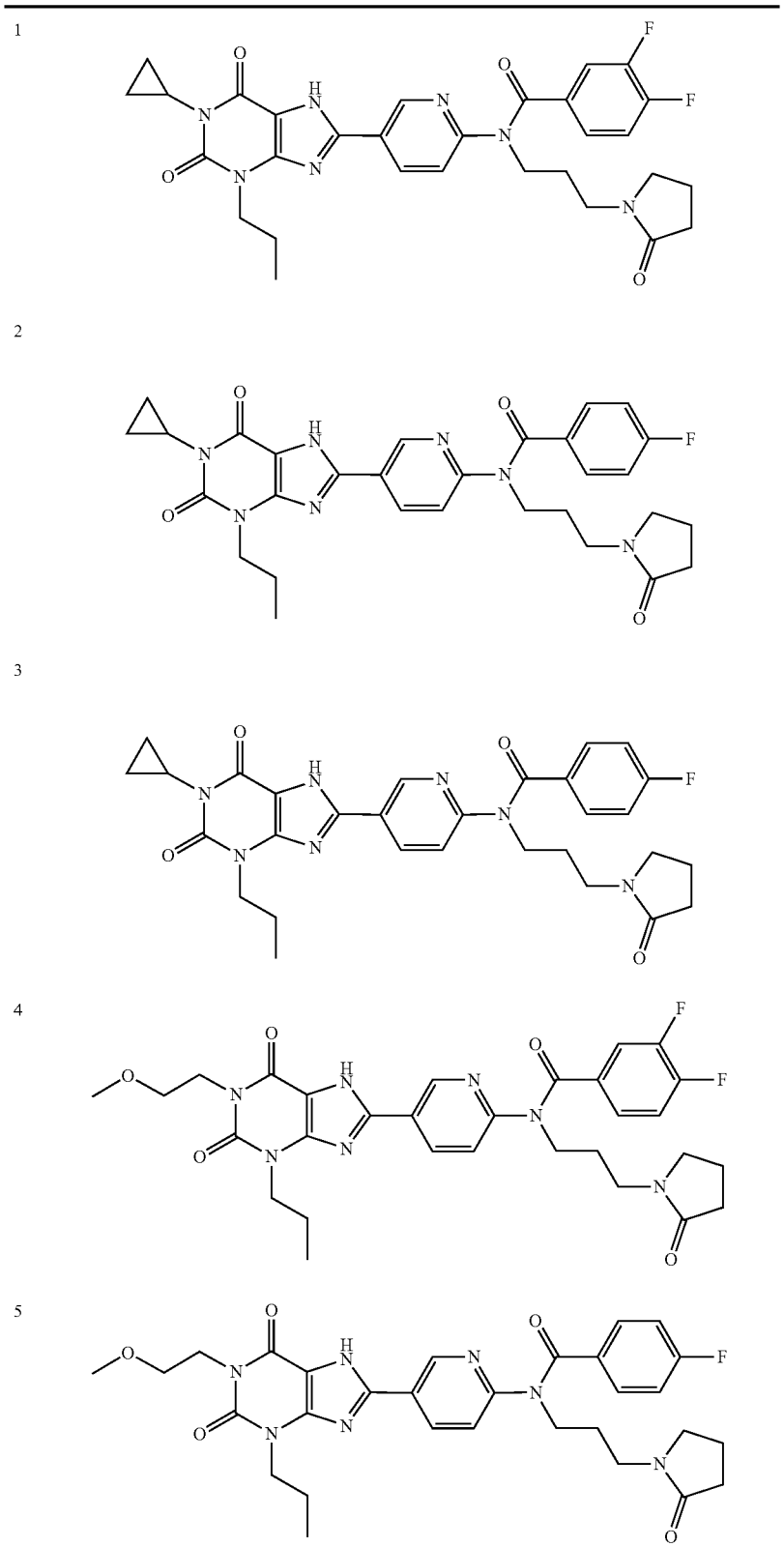

TABLE 3-continued
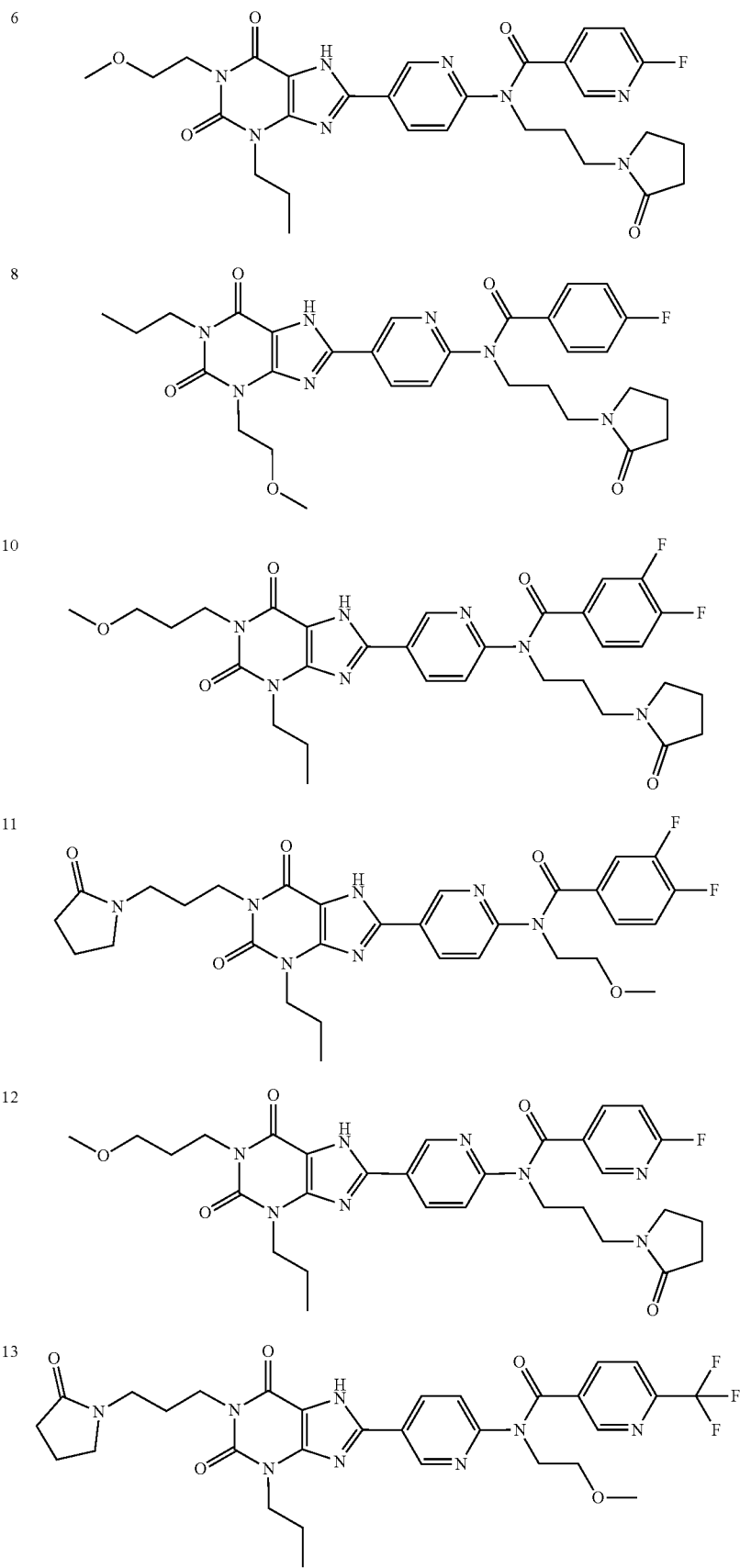

TABLE 3-continued
15 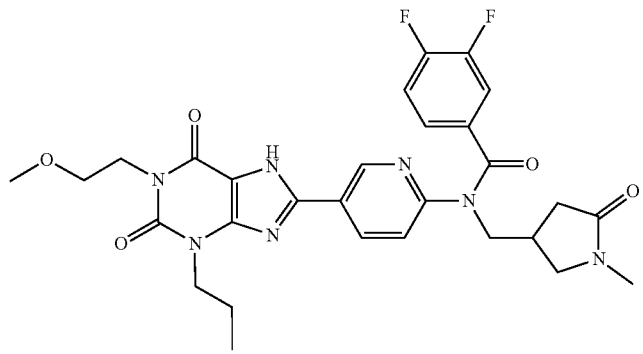
16 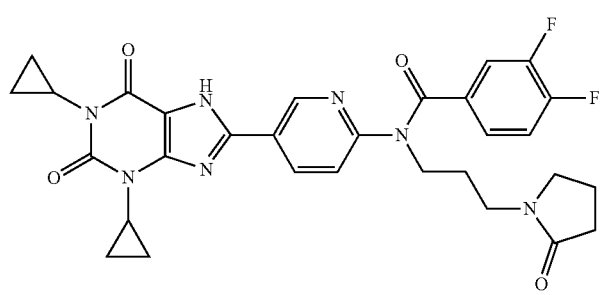 [SMILES: O=C1CCCN1CCCN(C(=O)c1ccc(F)c(F)c1)c1ccc(-c2nc3c([nH]2)c(=O)n(C2CC2)c(=O)n3C2CC2)cn1]
20 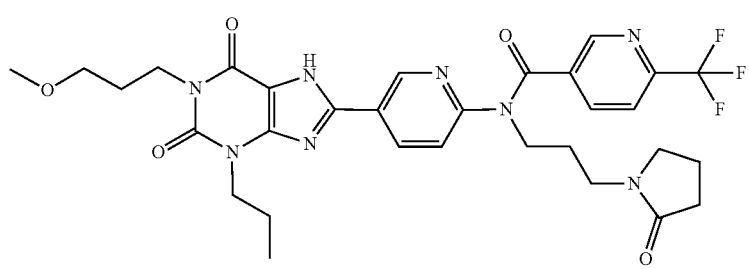 [SMILES: CCCn1c(=O)n(CCCOC)c(=O)c2[nH]c(-c3ccc(N(CCCN4CCCC4=O)C(=O)c4ccc(C(F)(F)F)nc4)nc3)nc21]
24 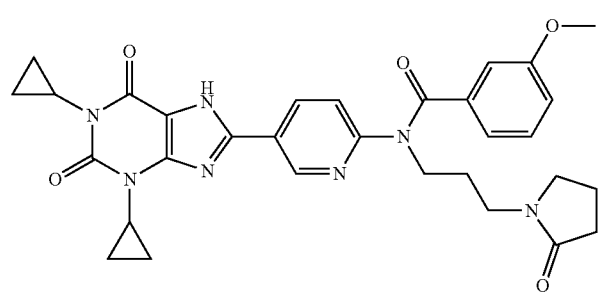 [SMILES: COc1cccc(C(=O)N(CCCN2CCCC2=O)c2ccc(-c3nc4c([nH]3)c(=O)n(C3CC3)c(=O)n4C3CC3)cn2)c1]
25 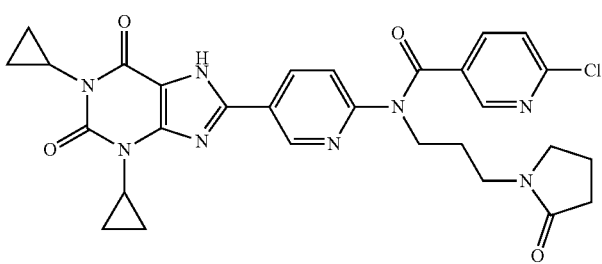 [SMILES: O=C1CCCN1CCCN(C(=O)c1ccc(Cl)nc1)c1ccc(-c2nc3c([nH]2)c(=O)n(C2CC2)c(=O)n3C2CC2)cn1]

TABLE 3-continued
26
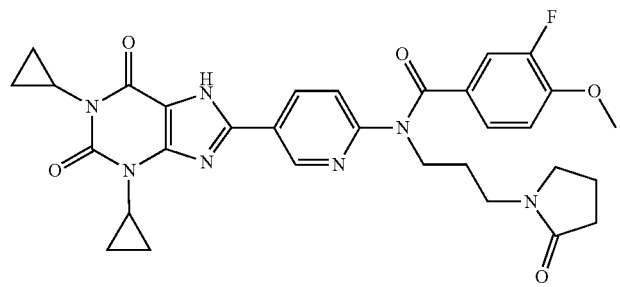 [SMILES: COc1ccc(C(=O)N(CCCN2CCCC2=O)c2ccc(-c3nc4c([nH]3)c(=O)n(C3CC3)c(=O)n4C3CC3)cn2)cc1F]
27
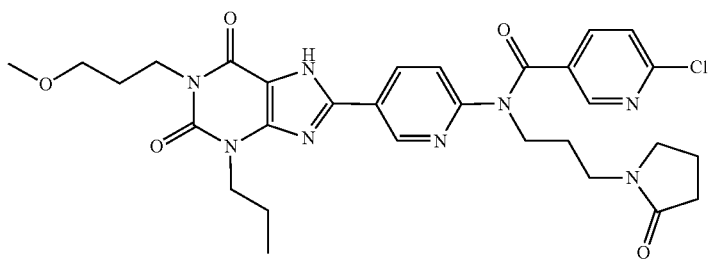 [SMILES: CCCn1c(=O)n(CCCOC)c(=O)c2[nH]c(-c3ccc(N(CCCN4CCCC4=O)C(=O)c4ccc(Cl)nc4)nc3)nc21]
28
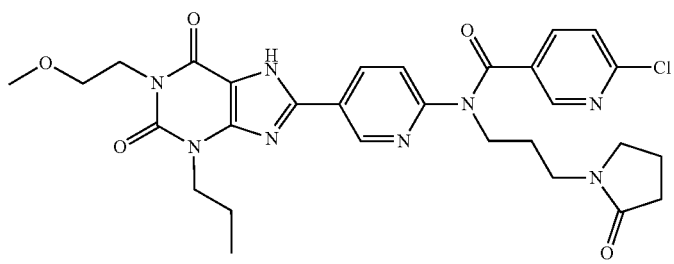 [SMILES: CCCn1c(=O)n(CCOC)c(=O)c2[nH]c(-c3ccc(N(CCCN4CCCC4=O)C(=O)c4ccc(Cl)nc4)nc3)nc21]
30
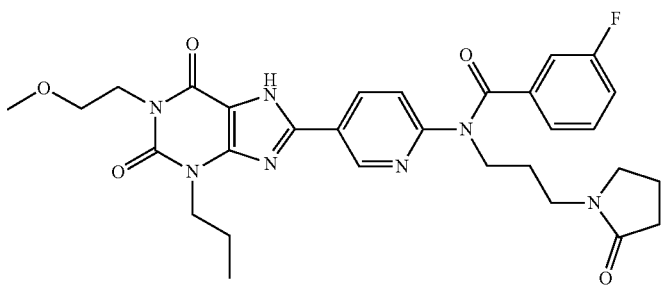 [SMILES: CCCn1c(=O)n(CCOC)c(=O)c2[nH]c(-c3ccc(N(CCCN4CCCC4=O)C(=O)c4cccc(F)c4)nc3)nc21]
13. A compound of claim 1, wherein the compound is selected from the compounds of Table 4 or a stereoisomer or pharmaceutically acceptable salt thereof;
TABLE 4
1
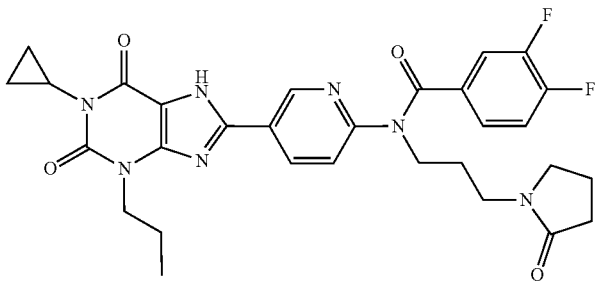 [SMILES: CCCn1c(=O)n(C2CC2)c(=O)c2[nH]c(-c3ccc(N(CCCN4CCCC4=O)C(=O)c4ccc(F)c(F)c4)nc3)nc21]

TABLE 4-continued
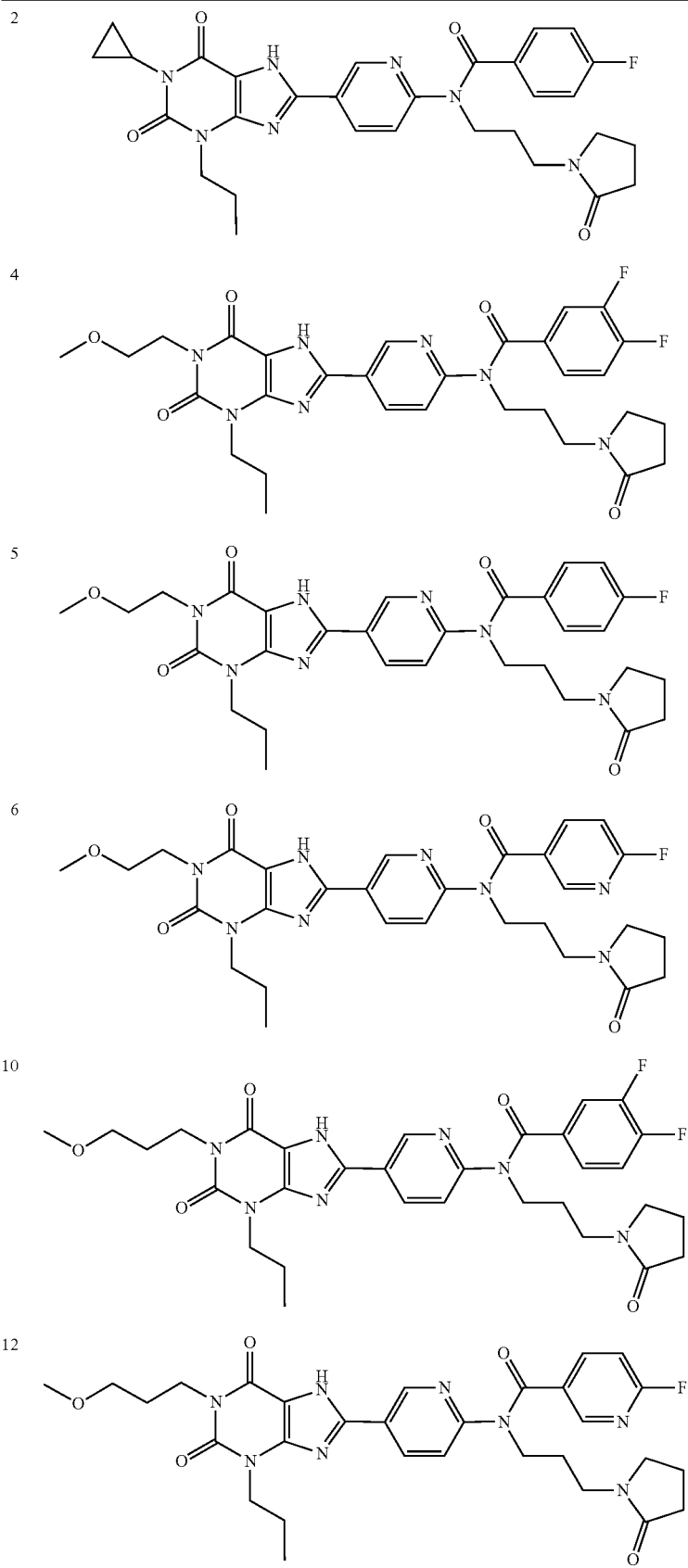

TABLE 4-continued
24
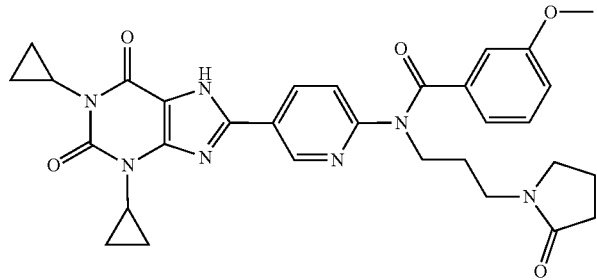 [SMILES: COc1cccc(C(=O)N(CCCN2CCCC2=O)c2ccc(-c3nc4c([nH]3)c(=O)n(C3CC3)c(=O)n4C3CC3)cn2)c1]
25
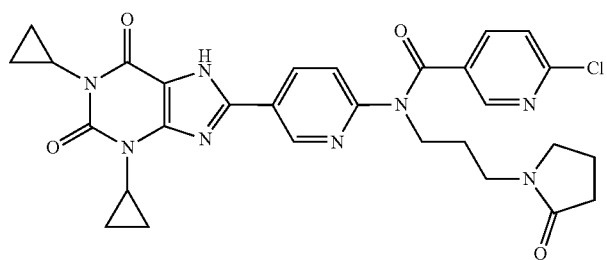 [SMILES: O=C1CCCN1CCCN(C(=O)c1ccc(Cl)nc1)c1ccc(-c2nc3c([nH]2)c(=O)n(C2CC2)c(=O)n3C2CC2)cn1]
26
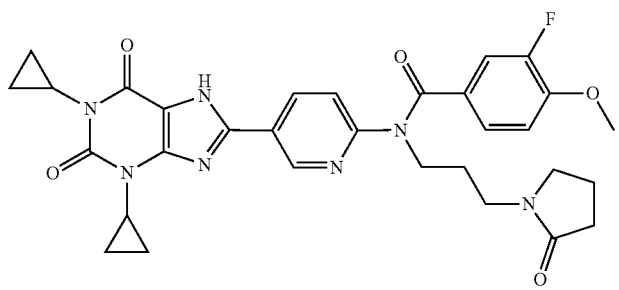 [SMILES: COc1ccc(C(=O)N(CCCN2CCCC2=O)c2ccc(-c3nc4c([nH]3)c(=O)n(C3CC3)c(=O)n4C3CC3)cn2)cc1F]
27
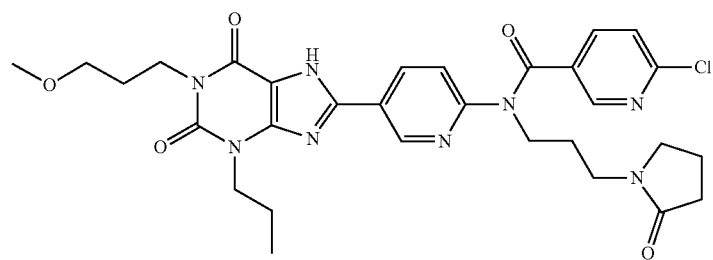 [SMILES: CCCn1c(=O)n(CCCOC)c(=O)c2[nH]c(-c3ccc(N(CCCN4CCCC4=O)C(=O)c4ccc(Cl)nc4)nc3)nc21]
28
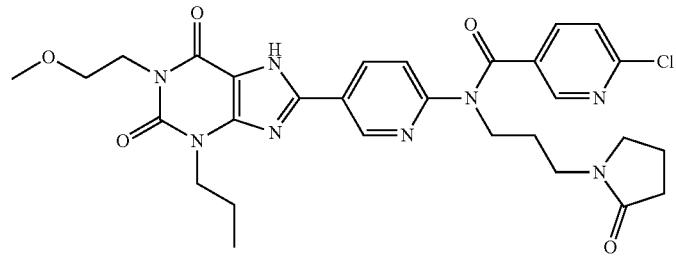 [SMILES: CCCn1c(=O)n(CCOC)c(=O)c2[nH]c(-c3ccc(N(CCCN4CCCC4=O)C(=O)c4ccc(Cl)nc4)nc3)nc21]

TABLE 4-continued

30

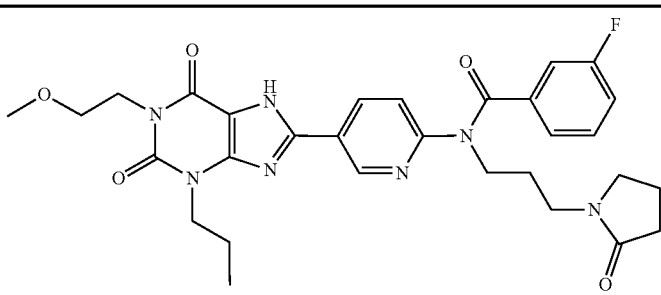

14. A pharmaceutical composition, comprising: a compound of claim 1 or a stereoisomer or pharmaceutically acceptable salt thereof and a pharmaceutically acceptable carrier.

15. A pharmaceutical composition, comprising: a compound of claim 2 or a stereoisomer or pharmaceutically acceptable salt thereof and a pharmaceutically acceptable carrier.

16. A pharmaceutical composition, comprising: a compound of claim 3 or a stereoisomer or pharmaceutically acceptable salt thereof and a pharmaceutically acceptable carrier.

17. A pharmaceutical composition, comprising: a compound of claim 4 or a stereoisomer or pharmaceutically acceptable salt thereof and a pharmaceutically acceptable carrier.

18. A pharmaceutical composition, comprising: a compound of claim 5 or a stereoisomer or pharmaceutically acceptable salt thereof and a pharmaceutically acceptable carrier.

19. A pharmaceutical composition, comprising: a compound of claim 6 or a stereoisomer or pharmaceutically acceptable salt thereof and a pharmaceutically acceptable carrier.

20. A pharmaceutical composition, comprising: a compound of claim 7 or a stereoisomer or pharmaceutically acceptable salt thereof and a pharmaceutically acceptable carrier.

21. A pharmaceutical composition, comprising: a compound of claim 8 or a stereoisomer or pharmaceutically acceptable salt thereof and a pharmaceutically acceptable carrier.

22. A pharmaceutical composition, comprising: a compound of claim 9 or a stereoisomer or pharmaceutically acceptable salt thereof and a pharmaceutically acceptable carrier.

23. A pharmaceutical composition, comprising: a compound of claim 10 or a stereoisomer or pharmaceutically acceptable salt thereof and a pharmaceutically acceptable carrier.

24. A pharmaceutical composition, comprising: a compound of claim 11 or a stereoisomer or pharmaceutically acceptable salt thereof and a pharmaceutically acceptable carrier.

25. A pharmaceutical composition, comprising: a compound of claim 12 or a stereoisomer or pharmaceutically acceptable salt thereof and a pharmaceutically acceptable carrier.

26. A pharmaceutical composition, comprising: a compound of claim 13 or a stereoisomer or pharmaceutically acceptable salt thereof and a pharmaceutically acceptable carrier.

27. A pharmaceutical composition, comprising: a compound of claim 14 or a stereoisomer or pharmaceutically acceptable salt thereof and a pharmaceutically acceptable carrier.

\* \* \* \* \*